(12) United States Patent
Harper et al.

(10) Patent No.: US 6,573,094 B1
(45) Date of Patent: *Jun. 3, 2003

(54) F-BOX GENES AND PROTEINS

(75) Inventors: Jeffrey Wade Harper, Sugarland, TX (US); Stephen J. Elledge, Houston, TX (US)

(73) Assignee: Baylor College of Medicine, Houston, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/951,621

(22) Filed: Oct. 16, 1997

(51) Int. Cl.⁷ .............................. C12N 5/00; C12N 1/20; C12N 15/00; C07H 21/04
(52) U.S. Cl. .................... 435/325; 536/23.1; 536/23.5; 435/252.3; 435/320.1
(58) Field of Search ............................... 536/23.1, 23.5; 435/69.1, 252.3, 320.1, 325

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,946,778 A | 8/1990 | Ladner et al. |
| 4,965,188 A | 10/1990 | Mullis et al. |
| 5,384,255 A | 1/1995 | Ciechanover et al. |
| 5,519,003 A | 5/1996 | Mochly-Rosen et al. |

FOREIGN PATENT DOCUMENTS

| | | |
|---|---|---|
| WO | WO 90/13678 | 11/1990 |
| WO | WO 95/04064 | 2/1995 |
| WO | WO 96/33286 | 10/1996 |

OTHER PUBLICATIONS

Hillier, L. et al. GenBank Accession No. AA478504.*
Auffrey, C. et al. GenBank Accession No. F12916, Mar. 1995.*
White, R. et al. Analysis of cloned factors. In: Transcription Factors: A Practical Approach, IRL Press, New York, pp. 143–179, 1993.*
Darnell, J., et al., Molecular Cell Biology. Scientific American Books, New York, pp. 248, 249, 254–260, 1995.*
Hillier, L. et al. The Wash U–Merck EST Project, Human Clone 23052, Mar. 1995.*
Hillier, L. et al. The Wash U–Merck EST Project, Human Clone 45203, Jun. 1995.*
Adams, M. D. et al. Nature Genet. 4: 256–267, Jul. 1993.*
Anderson and Young, "Quantitative Filter Hybridization," in Nucleic Acid Hybridization [1985].
Ausubel et al., Short Protocols in Molecular Biology, pp. 13.29–13.30, John Wiley & Sons, New York [1992].

Bai et al., "SKP1 Connects Cell Cycle Regulators to the Ubiquitin Proteolysis Machinery through a Novel Motif, the F–Box," Cell 86: 263–274 [1996].
Bai et al., "Human cyclin F," EMBO J. 15: 3611–3620 [1994].
Barral et al., "$G_1$ cyclin turnover and nutrient uptake are controlled by a common pathway in yeast," Genes & Dev. 9: 399–409 [1995].
Blondel and Mann, "G2 cyclins are required for the degradation of G1 cyclins in yeast," Nature 384: 279–382 [1996].
Boshart et al., "A Very Strong Enhancer is Located Upstream of an Immediate Early Gene of Human Cytomegalovirus," Cell 41:521–530 [1985].
Breeden and Nasmyth, Cold Spring Harbor Symp. Quant. Biol. 50: 643–650 [1985].
Chamberlin et al., "New RNA Polymerase from Escherichia coli infected with Bacteriophage T7," Nature 228:227–231 [1970].
Chau et al., "A Multiubiquitin Chain is Confined to Specific Lysine in a Targeted Short–Lived Protein," Science 243: 1576–1583 [1989].
Clurman et al., "Turnover of cyclin E by the ubiquitin–proteasome pathway is regulated by cdk2 binding and cyclin phosphorylation," Genes & Dev. 10: 1979–1990 [1996].
Cole et al., "The EBV–Hybridoma Technique And Its Application to Human Lung Cancer," in Monoclonal Antibodies and Cancer Therapy, pp. 77–96, Alan R. Liss, Inc. [1985].
Connell–Crowley et al., "Cyclin D1/Cdk4 Regulates Retinoblastoma Protein–mediated Cell Cycle Arrest by Site–specific Phosphorylation," Mol. Biol. Cell. 8: 287–301 [1997].
Connelly and Hieter, "Budding Yeast SKP1 Encodes an Evolutionarily Conserved Kinetochore Protein Required for Cell Cycle Progression," Cell 86: 275–285 [1996].
Cote et al., "Generation of human monoclonal antibodies reactive with cellular antigens," Proc. Natl. Acad. Sci. USA 80: 2026–2030 [1983].
Deshaies et al., "Ubiquitination of the $G_1$ cyclin Cln2p by a Cdc34p–dependent pathway," EMBO J. 14: 303–312 [1995].
Diehl et al., "Inhibition of cyclin D1 phosphorylation on threonine–286 prevents its rapid degradation via the ubiquitin–proteasome pathway," Genes & Dev. 11: 957–972 [1997].

(List continued on next page.)

Primary Examiner—Christina Chan
Assistant Examiner—Maher Haddad
(74) Attorney, Agent, or Firm—Gardere Wynne Sewell LLP

(57) ABSTRACT

The present invention provides compositions and methods for gene identification, as well as drug discovery and assessment. In particular, the present invention provides components of an E3 complex involved in ubiquitination of cell cycle regulators and other proteins, as well as members of a class of proteins that directly function in recognition of ubiquitination targets. The present invention also provides sequences of multiple F-box proteins.

23 Claims, 18 Drawing Sheets

OTHER PUBLICATIONS

Dijkema et al., "Cloning and expression of the chromosomal immune interferon gene of the rat," *EMBO J.* 4:761–767 [1985];.

Erlich (ed.), *PCR Technology,* Stockton Press [1989].

Flick and Johnston, "GRRI of *Saccharomyces cerevisiae* Is Required for Glucose Repression and Encodes a Protein with Leucine–Rich Repeats," *Mol. Cell. Biol.* 11: 5101–5112 [1991].

Gorman et al., "The Rous sarcoma virus long terminal repeat is a strong promoter when introduced into a variety of eukaryotic cells by DNA–mediated transfection," *Proc. Natl. Acad. Sci. USA* 79:6777–6781 [1992].

Harlow and Lane, *Antibodies: A Laboratory Manual,* Cold Spring Harbor Press, New York [1988].

Harper et al., "The p21 Cdk–Interacting Protein Cip1 is a Potent Inhibitor of G1 Cyclin–Dependent Kinases," *Cell* 75: 805–816 [1993].

Hodgins et al., "Expression of a Ubiquitin Derivative That Conjugates to Protein Irreversibily Produces Phenotypes Consistent with a Ubiquitin Deficiency," *J. Biol. Chem.* 267: 8807–8812 [1992].

Huibregtse et al., "A family of proteins structurally and functionally related to the E6–AP ubiquitin–protein ligase," *Proc. Natl. Acad. Sci. USA* 92: 2563–2567 [1995].

Huse et al., "Generation of a Large Combinatorial Library of the Immunoglobulin Repertoire in Phage Lambda," *Science* 246: 1275–1281 [1989].

Kacian et al., "A Replicating RNA Molecule Suitable for a Detailed Analysis of Extracellular Evolution and Replication," *Proc. Natl. Acad. Sci. USA* 69:3038–3042 [1972].

Kim et al., "Use of the human elongation factor 1α promoter as a versatile and efficient expression system," *Gene* 91:217–223 [1990].

King et al., "How Proteolysis Drives the Cell Cycle," *Science* 274: 1652–1659 [1996].

Kipreos et al., "cul–1 Is Required for Cell Cycle Exit in *C. elegans* and Identifies a Novel Gene Family," *Cell* 85: 829–839 [1996].

Kohler and Milstein, "Continuous cultures of fused cells secreting antibody of predefined specificity," *Nature* 256: 495–497 [1975].

Kominami and Toda, "Fission yeast WD–repeat protein Pop1 regulates genome ploidy through ubiquitin–proteasome–mediated degradation of the CDK inhibitor Rum1 and the S–phase Cdc18," *Genes & Dev.* 11:1548–1560 [1997].

Kornitzer et al., "Regulated degradation of the transcription factor Gcn4," *EMBO J.* 13: 6021–6030 [1994].

Lanker et al., "Rapid Degradation of the $G_1$ Cyclin Cln2 Induced by CDK–Dependent Phosphorylation," *Science* 271: 1597–1601 [1996].

Maniatis et al., "Regulation of Inducible and Tissue–Specific Gene Expression," *Science* 236:1237–1244 [1987].

Mathias et al., "Cdc53p Acts in Concert with Cdc4p and Dcd34p To Control the G1–to–S–Phase Transition and Identifies a Conserved Family of Proteins," *Mol. Cell Biol.* 16: 6634–6643 [1996].

McKinney et al., "Negative regulation of FAR1 at the Start of the yeast cell cycle," *Genes & Dev.* 7: 833–843 [1993].

Mendenhall, "An Inhibitor of $p34^{CDC28}$ Protein Kinase Activity from *Saccharomyces cerevisiae,*" *Science* 259: 216–219 [1993].

Mizushima and S. Nagata, "pEF–BOS, a powerful mammalian expression vector," *Nuc. Acids Res.* 18:5322 [1990].

Nasmyth, "Control of the yeast cell cycle by the Cdc28 protein kinase," *Curr. Opin. Cell Biol.* 5: 166–179 [1993].

Nielsen et al., "Peptide nucleic acids (PNAs): Potential anti–sense and anti–gene agents," *Anticancer Drug Des.* 8:53–63 [1993].

Piatti et al., "Activation of S–phase–promoting CDKs in late $G_1$ defines a "point of o return" after which Dcd6 synthesis cannot promote DNA replication in yeast," *Genes & Dev.* 10: 1516–1531 [1996].

Rogers et al., "Amino Acid Sequences Common to Rapidly Degraded Proteins: The PEST Hypothesis," *Science* 234: 364–368 [1986].

Rolfe et al., "Reconstitution of p53–ubiquitinylation reactions from purified components: The role of human ubiquitin–conjugating enzyme UBC4 and E6–associated protein (E6AP)," *Proc. Natl. Acad. Sci. USA* 92: 3264–3268 [1995].

Sambrook et al., *Molecular Cloning: A Laboratory Manual,* 2nd ed., Cold Spring Harbor Laboratory Press, New York [1989], pp.7.39–7.52, 9.31–9.58, 16.6–16.15.

Scheffner et al., "The HPV–16 E6 and E6–AP Complex Functions as a Ubiquitin–Protein Ligase in the Ubiquitination of p53," *Cell* 75: 495–505 [1993].

Scheffner et al., "Protein ubiquitination involving an E1–E2–E3 enzyme ubiquitin thioester cascade," *Nature* 373: 81–83 [1995].

Scheaff et al., "Cyclin E–CDK2 is a regulator of $p27^{Kip1}$," *Genes & Dev.* 11: 1464–1478 [1997].

Schneider et al., "Linkage of Replication to Start by the Cdk Inhibitor Sic 1," *Science* 272: 560–562 [1996].

Schwob et al., "The B–Type Cyclin Kinase Inhibitor $p40^{SIc1}$ Controls the G1 to S Transition in *S. Cerevisiae,*" *Cell* 79: 233–244 [1994].

Stemmann and Lechner, "The *Saccharomyces cerevisiae* kinetochore contains a cyclin–CDK complexing homologue, as identified by in vitro reconstitution," *EMBO J.* 15: 3611–3620 [1996].

Thomas et al., "Met30p, a Yeast Transcriptional Inhibitor That Responds to S–Adenosylmethionine, Is an Essential Protein with WD40 Repeats," *Mol. Cell. Biol.* 15: 6526–6534 [1995].

Tyers et al., "The Cln3–Cdc28 kinase complex of *S. cerevisiae* is regulated by proteolysis and phosphorylation," *EMBO J.* 11: 1773–1184 [1992].

Tyers, "The cyclin–dependent kinase inhibitor $p40^{SIC1}$ imposes the requirement for Cln G1 cyclin function at Start," *Proc. Natl. Acad. Sci. USA* 93: 7772–7776 [1996].

Uetsuki et al., "Isolation and Characterization of the Human Chromosomal Gene for Polypeptide Chain Elongation Factor–1α," *J. Biol. Chem.* 264:5791 [1989].

Voss et al., "The role of enhancers in the regulation of cell–type–specific transcriptional control," *Trends Biochem. Sci.* 11:287–289 [1986].

Willems et al., "Cdc53 Targets Phosphorylated G1 Cyclins for Degradation by the Ubiquitin Proteolytic Pathway," *Cell* 86: 453–463 [1996].

Won and Reed, "Activation of cyclin E/CDK2 is coupled to site–specific autophosphorylation and ubiquitin–dependent degradation of cyclin E," *EMBO J.* 15: 4182–4193 [1996].

Wu and Wallace, "The Ligation Amplification Reaction (LAR)—Amplification of Specific DNA Sequences Using Sequential Rounds of Template–Dependent Ligation," *Genomics* 4:560–569 [1989].

Yochem and Byers, "Structural Comparison of the Yeast Cell Division Cycle Gene CDC4 and a Related Pseudogene," *J. Mol. Biol.* 195: 233–245 [1987].

Zhang et al., "p19$^{Skp1}$ and p45$^{Skp2}$ Are Essential Elements of the Cyclin A–CKD2 S Phase Kinase," *Cell* 82: 915–925 [1995].

Rolfe et al., "The Ubiquitin–mediated proteolytic pathway as a therapeutic area," *J. Mol. Med.* 75: 5–17 (1997).

Hasselgren and Fischer, "The Ubiquitin–Proteaseome Pathway, Review of a Novel Intracellular Mechanism of Muscle Protein Breakdown During Sepsis and Other Catabolic Conditions," *Annals of Surgery,* 225: 307–316 (1997).

Stancovski et al., "Degradation of the Proto–Oncogene Product c–Fos by the Ubiquitin Proteolytic System In Vivo and In Vitro: Identification and Characterization of the Conjugating Enzymes," *Mol. Cell. Biol.* 15: 7106–7116 (1995).

Huang et al., "Control of Cell Fate by a Deubiquitinating Enzyme Encoded by the fat facets Gene," *Science* 270: 1828–1831 (1995).

Tamura et al., "Improved method for preparation of ubiquitin–ligated lysozyme as substrate of ATP–dependent proteolysis," *FEBS Lett.* 292: 154–158 (1991).

Blumenfeld et al., "Purification and Characterization of a Novel Species of Ubiquitin–Carrier Protein, E2, That is Involved in Degradation of Non–"N–end Rule" Protein Substrates," *J. Biol. Chem.* 269: 9574–9581 (1994).

Wing et al., "A Rabbit Reticulocyte Ubiquitin Carrier Protein That Supports Ubiquitin–dependent Proteolysis (E2$_{14k}$) is Homologous to the Yeast DNA Repair Gene RAD6," *J. Biol. Chem.* 267: 6495–6501 (1992).

Baboshina and Haas, "Novel Multiubiquitin Chain Linkages Catalyzed by the Conjugating Enzymes E2$_{EPF}$ and RAD6 are Recognized by 26S Proteasome Subunit 5," *J. Biol. Chem.* 271: 2823–2831 (1996).

Pickart and Rose, "Functional Heterogeneity of Ubiquitin Carrier Proteins," *J. Biol. Chem.* 260: 1573–1581 (1985).

Yu et al., "Identification of a novel ubiquitin–conjugating enzyme involved in mitotic cyclin degradation," *Curr. Biol.* 6:455–466 (1996).

McDonough et al., "Characterization of Novel Yeast RAD6 (UBC2) Ubiquitin–Conjugating Enzyme Mutants Constructed by Charge–to–Alanine Scanning Mutagenesis," *J. Bacteriol.* 177: 580–585 (1995).

Lam et al., "Editing of ubiquitin conjugates by an isopeptidase in the 26S proteasome," *Nature* 385: 737–740 (1997).

Nasmyth, "Viewpoint: Putting the Cell Cycle in Order," *Science* 274: 1643–1645 (1996).

Sondek et al., "Crystal structure of a GA protein βγ dimer at 2.1Å resolution," *Nature* 379: 369–374 (1996).

Skowyra et al., "F–Box Proteins Are Receptors That Recruit Phosphorylated Substrates to the SCF Ubiquitin–Ligase Complex," *Cell* 91: 1–20 (1997).

* cited by examiner

FIG. 1A
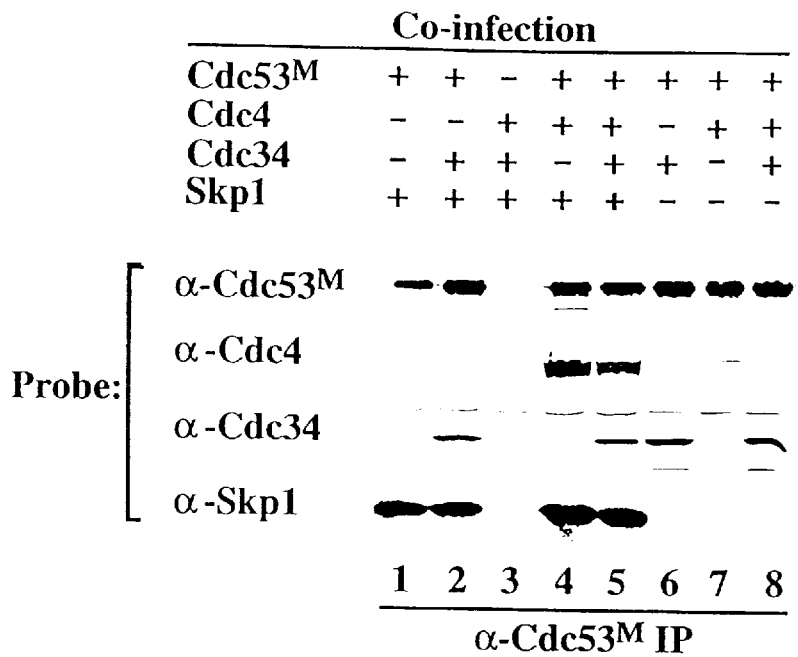
FIG. 1B
FIG. 1C
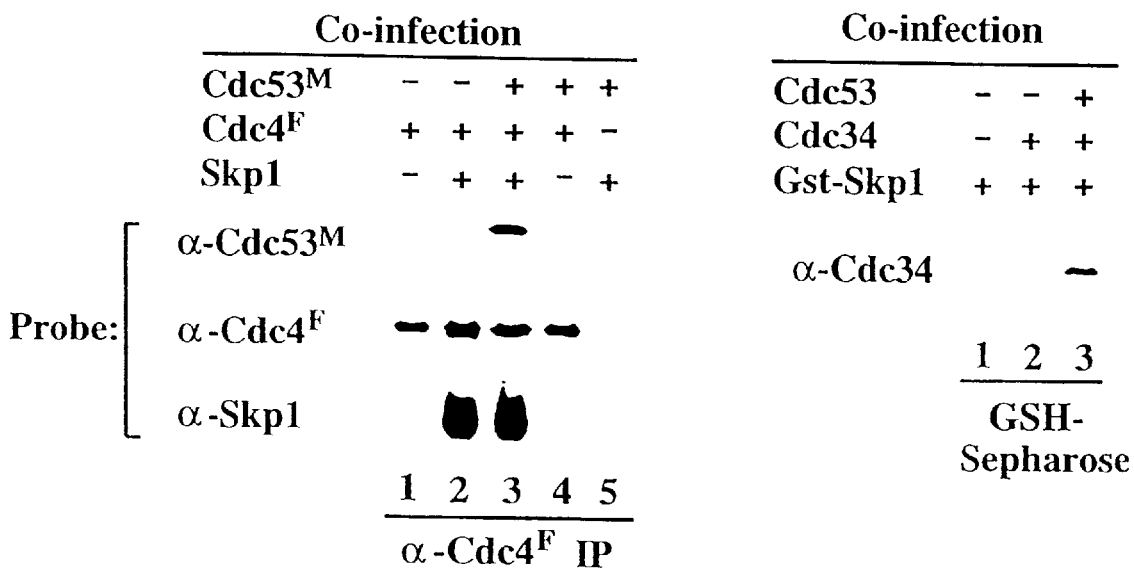

Coomassie Stain

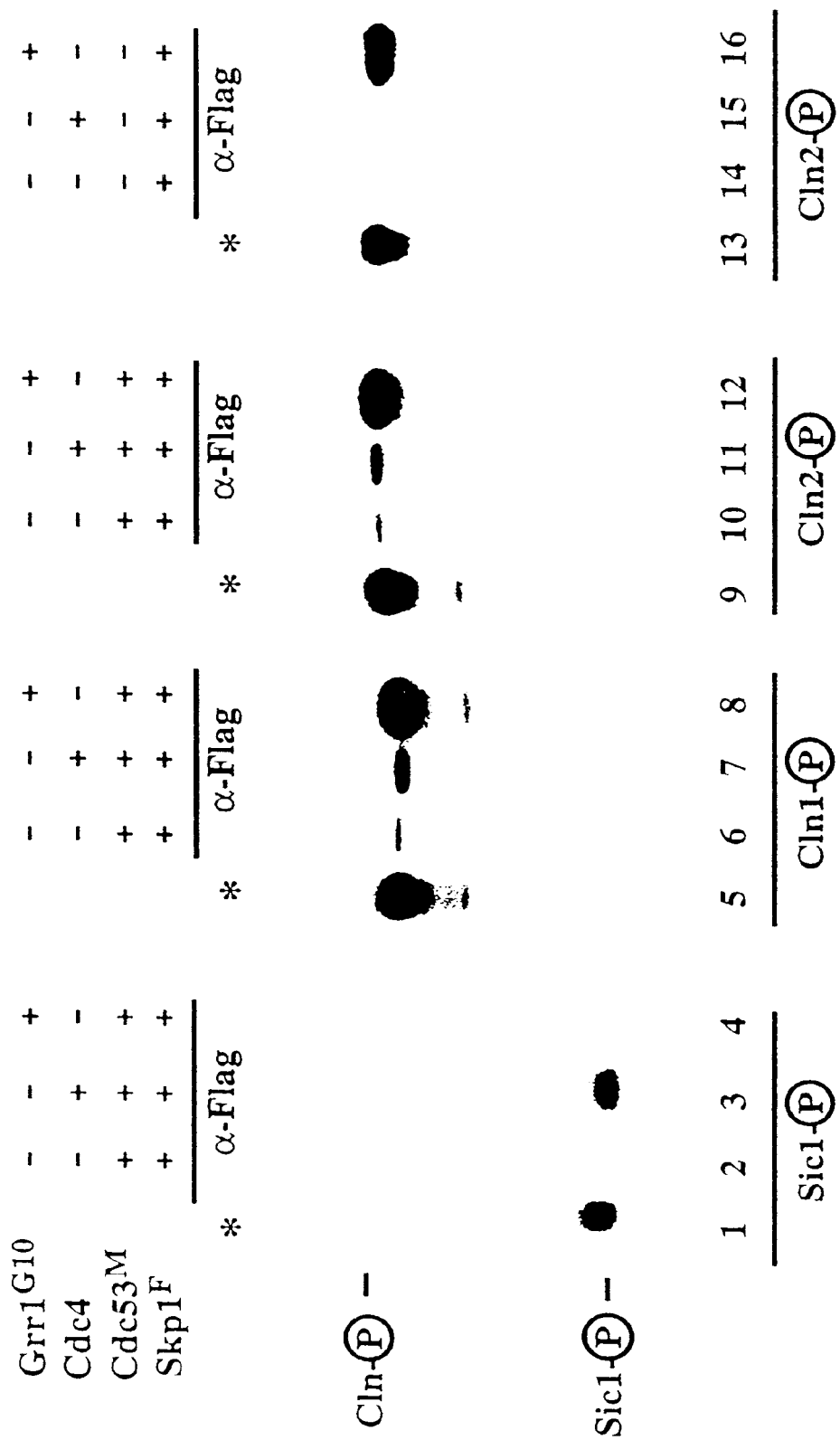

| | | | |
|---|---|---|---|
| $Grr1^{G10}$ | − | − | + |
| $Cdc4$ | − | + | − |
| $Cdc53^{M}$ | + | + | + |
| $Skp1^{F}$ | + | + | + |

α-Flag $Grr1^{G10}$-

$Cdc4$-

$Cdc53^{M}$-

$Skp1^{F}$-

| Name | | F-Box | |
|---|---|---|---|
| TRCP | (h) | LPARGLDIHAENILSY-----LDAKSLCAAELVCKEWYRVTSDGM---IW | SEQ. ID NO: 1 |
| F1 (Alpha) | (h) | LPK----ELLLRIFSF-----LDIVTLCRCAQISKAWNILALDGS---NW | SEQ. ID NO: 3 |
| F2 (Beta) | (h) | LPY----ELIQLILNH-----LTLPDLCRLAQTCKLLSQHCCDPL---QY | SEQ. ID NO: 5 |
|  | (m) | LPY----ELIQLILNH-----LSLPDLCRLAQTCRLLHQHCCDPL---QY | SEQ. ID NO: 7 |
| F3 (Gamma) | (h) | LPT----DPLLLILSF-----LDYRDLINCCYVSRRLSQLSSHDP---LW | SEQ. ID NO: 9 |
|  | (m) | LPT----DPLLLILSF-----VDYRDLINCCYVSRRLSQLSTHDP---LW | SEQ. ID NO: 11 |
| F4 (Delta) | (h) | LPP----EVMLSIFSY-----LNPQELCRCSQVSMKWSQLTKTGS---LW | SEQ. ID NO: 13 |
|  | (m) | LPP----EVMLSIFSY-----LNPQELCRCSQVSTKWSQLAKTGS---LW | SEQ. ID NO: 15 |
| F5 (Zeta) | (h) | LPL----EMLTYILSF-----LPLSDQKEASLVSWAWYRAAQNALRERLW | SEQ. ID NO: 17 |
| F6 (Eta) | (h) | LPP----ELSFTILSY-----LNATDLCLASCV---WQDLANDEL---LW | SEQ. ID NO: 19 |
|  | (m) | LPP----ELSFTILSY-----LNAIDLCLASCV---WQDLANDEL---LW | SEQ. ID NO: 21 |
| F7 (Theta) | (m) | LPR----VLSVYIFSF-----LDPRSLCRCAQVSWYWKSLAELDQ---LW | SEQ. ID NO: 23 |
| F8 (Iota) | (h) | LPI----DVQLYILSF-----LSPHDLCQLGSTNHYWNFTVRHPI---LW | SEQ. ID NO: 25 |
| F9 (Kappa) | (h) | LPL----ELWRMILAY-----LHLPDLGRCSLVCRAWYELILSLDST-RW | SEQ. ID NO: 27 |
| F10 (Lambda) | (m) | LPA----EITFKIFSQ-----LDIRSLCRASLTCRSWNDFKS | SEQ. ID NO: 29 |
| F11 (Mu) | (m) | LPL----LQQPLLCSV-----AHPIASFTMLSYLTGKEAAHLSVE---LW | SEQ. ID NO: 31 |
| F12 (Nu) | (m) | LPD----SLVYQIFLS-----LGPADVLAAGLVCRQWQAVSRDEF---LW | SEQ. ID NO: 33 |
| F13 (Omern) | (m) | LPE----EVLALIFRD-----LPLRDLAVATRVCRAWAAA | SEQ. ID NO: 35 |
| F14 (Pi) | (m) | LPS----VPMMEILSY-----LDAYSLLQAAQVNKNWNELASSDV---LW | SEQ. ID NO: 37 |
| F15 (Rho) | (m) | MPS----EILVKILSY-----LDAVTLVCIGCVSRRFYHLADDNL---IW | SEQ. ID NO: 39 |
| F16 (Sigma) | (h) | LPM----EVLMYIFRWVVSSDLDLRSLEQLSLVCRGFYICARDPE---IW | SEQ. ID NO: 41 |
|  | (m) |                         DLRSLEQLSLVCRGFYICARDPE---IW | SEQ. ID NO: 43 |
| F17 (Tau) | (h) | LPY----ELAINIFXY-----LDRKELGRCAQVSKTWEGD | SEQ. ID NO: 45 |
| F18 (Phi) | (h) | LPL----ELKLRIFRL-----LDVRSVLSLSAVCRDLFTASNDPL---LW | SEQ. ID NO: 47 |
|  | (m) | LPL----ELKLRIFRL-----LDVHSVLASLSAVCHDLLIASNDPL---LW | SEQ. ID NO: 49 |

SEQUENCE LISTING (1) GENERAL INFORMATION:

(iii) NUMBER OF SEQUENCES: 59

(2) INFORMATION FOR SEQ ID NO:1:

(i) SEQUENCE CHARACTERISTICS:
      (A) LENGTH: 42 amino acids
      (B) TYPE: amino acid
      (C) STRANDEDNESS: Not Relevant
      (D) TOPOLOGY: Not Relevant (ii) MOLECULE TYPE: protein (xi) SEQUENCE DESCRIPTION: SEQ ID NO:1:

Leu Pro Ala Arg Gly Leu Asp His Ile Ala Glu Asn Ile Leu Ser Tyr
1             5                   10               15

```
Leu Asp Ala Lys Ser Leu Cys Ala Ala Glu Leu Val Cys Lys Glu Trp
            20                  25                  30

Tyr Arg Val Thr Ser Asp Gly Met Leu Trp
        35                  40
```

(2) INFORMATION FOR SEQ ID NO:2:

(i) SEQUENCE CHARACTERISTICS:
        (A) LENGTH: 126 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:2:

```
CTGCCAGCTC GGGGATTGGA TCATATTGCT GAGAACATTC TGTCATACCT GGATGCCAAA      60

TCACTATGTG CTGCTGAACT TGTGTGCAAG GAATGGTACC GAGTGACCTC TGATGGCATG     120

CTGTGG                                                                126
```

(2) INFORMATION FOR SEQ ID NO:3:

(i) SEQUENCE CHARACTERISTICS:
        (A) LENGTH: 38 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:3:

```
Leu Pro Lys Glu Leu Leu Leu Arg Ile Phe Ser Phe Leu Asp Ile Val
1               5                   10                  15

Thr Leu Cys Arg Cys Ala Gln Ile Ser Lys Ala Trp Asn Ile Leu Ala
            20                  25                  30

Leu Asp Gly Ser Asn Trp
        35
```

(2) INFORMATION FOR SEQ ID NO:4:

(i) SEQUENCE CHARACTERISTICS:
        (A) LENGTH: 114 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:4:

```
TTACCCAAAG AACTTCTGTT AAGAATATTT TCCTTCTTGG ATATAGTAAC TTTGTGCCGA      60

TGTGCACAGA TTTCCAAGGC TTGGAACATC TTAGCCCTGG ATGGAAGCAA CTGG           114
```

(2) INFORMATION FOR SEQ ID NO:5:

(i) SEQUENCE CHARACTERISTICS:
        (A) LENGTH: 38 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:5:

```
Leu Pro Tyr Glu Leu Ile Gln Leu Ile Leu Asn His Leu Thr Leu Pro
1               5                   10                  15
Asp Leu Cys Arg Leu Ala Gln Thr Cys Lys Leu Leu Ser Gln His Cys
                20                  25                  30
Cys Asp Pro Leu Gln Tyr
            35
```

(2) INFORMATION FOR SEQ ID NO:6:

(i) SEQUENCE CHARACTERISTICS:
        (A) LENGTH: 71 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:6:

```
CTACCTTATG AGCTTATTCA GCTGATTCTG AATCATCTTA CACTACCAGA CCTGTGTAGA      60

TTAGCACAGA C                                                          71
```

(2) INFORMATION FOR SEQ ID NO:7:

(i) SEQUENCE CHARACTERISTICS:
        (A) LENGTH: 38 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:7:

```
Leu Pro Tyr Glu Leu Ile Gln Leu Ile Leu Asn His Leu Ser Leu Pro
1               5                   10                  15
Asp Leu Cys Arg Leu Ala Gln Thr Cys Arg Leu Leu His Gln His Cys
                20                  25                  30
Cys Asp Pro Leu Gln Tyr
            35
```

(2) INFORMATION FOR SEQ ID NO:8:

(i) SEQUENCE CHARACTERISTICS:
        (A) LENGTH: 114 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:8:

```
CTACCATATG AGCTCATTCA ACTGATTCTG AATCATCTTT CACTACCAGA CCTGTGTAGA      60

TTAGCCCAGA CTTGCAGGCT TCTCCACCAG CATTGCTGTG ATCCTCTGCA ATAT           114
```

(2) INFORMATION FOR SEQ ID NO:9:

(i) SEQUENCE CHARACTERISTICS:
        (A) LENGTH: 38 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:9:

Leu Pro Thr Asp Pro Leu Leu Leu Ile Leu Ser Phe Leu Asp Tyr Arg
 1               5                  10                  15

Asp Leu Ile Asn Cys Cys Tyr Val Ser Arg Arg Leu Ser Gln Leu Ser
             20                  25                  30

Ser His Asp Pro Leu Trp
         35

(2) INFORMATION FOR SEQ ID NO:10:

(i) SEQUENCE CHARACTERISTICS:
        (A) LENGTH: 114 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:10:

CTGCCCACCG ATCCCCTGCT CCTCATCTTA TCCTTTTTGG ACTATCGGGA TCTAATCAAC     60

TGTTGTTATG TCAGTCGAAG ACTTAGCCAG CTATCAAGTC ATGATCCGCT GTGG         114

(2) INFORMATION FOR SEQ ID NO:11:

(i) SEQUENCE CHARACTERISTICS:
        (A) LENGTH: 38 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:11:

Leu Pro Thr Asp Pro Leu Leu Leu Ile Val Ser Phe Val Asp Tyr Arg
 1               5                  10                  15

Asp Leu Ile Asn Cys Cys Tyr Val Ser Arg Ser Val Ser Gln Leu Ser
             20                  25                  30

Thr His Asp Pro Leu Trp
         35

(2) INFORMATION FOR SEQ ID NO:12:

(i) SEQUENCE CHARACTERISTICS:
        (A) LENGTH: 114 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:12:

CTACCCACCG ACCCTCTGCT CCTCATAGTA TCCTTCGTGG ACTACAGGGA CCTAATCAAT     60

TGTTGCTATG TTAGTCGAAG CGTTAGCCAG CTATCAACTC ATGATCCACT GTGG         114

(2) INFORMATION FOR SEQ ID NO:13:

(i) SEQUENCE CHARACTERISTICS:
        (A) LENGTH: 38 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:13:

Leu Pro Pro Glu Val Met Leu Ser Ile Phe Ser Tyr Leu Asn Pro Gln
1               5                   10                  15

Glu Leu Cys Arg Cys Ser Gln Val Ser Met Lys Trp Ser Gln Leu Thr
            20                  25                  30

Lys Thr Gly Ser Leu Trp
        35

(2) INFORMATION FOR SEQ ID NO:14:

(i) SEQUENCE CHARACTERISTICS:
        (A) LENGTH: 113 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:14:

CTTCCTCCTG AGGTAATGCT GTCAATTTTC AGCTATCTTA ATCCTCAAGA GTTATTCGAT    60

GCAGTCAAGT AAGCATGAAA TGGTCTCAGC TGACAAAAAC GGGATCGCTT TGG    113

(2) INFORMATION FOR SEQ ID NO:15:

(i) SEQUENCE CHARACTERISTICS:
        (A) LENGTH: 38 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:15:

Leu Pro Pro Glu Val Met Leu Ser Ile Phe Ser Tyr Leu Asn Pro Gln
1               5                   10                  15

Glu Leu Cys Arg Cys Ser Gln Val Ser Thr Lys Trp Ser Gln Leu Ala
            20                  25                  30

Lys Thr Gly Ser Leu Trp
        35

(2) INFORMATION FOR SEQ ID NO:16:

(i) SEQUENCE CHARACTERISTICS:
        (A) LENGTH: 114 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:16:

CTTCCTCCTG AGGTAATGCT GTCCATTTTC AGTTACCTTA ATCCTCAAGA ATTGTGTCGG    60

TGTAGTCAAG TCAGTACTAA GTGGTCTCAG CTGGCAAAAA CAGGATCTTT GTGG    114

(2) INFORMATION FOR SEQ ID NO:17:

(i) SEQUENCE CHARACTERISTICS:
        (A) LENGTH: 41 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:17:

```
Leu Pro Leu Glu Met Leu Thr Tyr Ile Leu Ser Phe Leu Pro Leu Ser
1               5                  10                  15

Asp Gln Lys Glu Ala Ser Leu Val Ser Trp Ala Trp Tyr Arg Ala Ala
            20                  25                  30

Gln Asn Ala Leu Arg Glu Arg Leu Trp
            35                  40
```

(2) INFORMATION FOR SEQ ID NO:18:

(i) SEQUENCE CHARACTERISTICS:
       (A) LENGTH: 123 base pairs
       (B) TYPE: nucleic acid
       (C) STRANDEDNESS: double
       (D) TOPOLOGY: linear (ii) MOLECULE TYPE: other nucleic acid
       (A) DESCRIPTION: /desc = "DNA"

(xi) SEQUENCE DESCRIPTION: SEQ ID NO:18:

```
CTGCCCCTGG AGATGCTCAC ATATATTCTG AGCTTCCTGC CTCTGTCAGA TCAGAAAGAG      60

GCCTCCCTCG TGAGTTGGGC TTGGTACCGT GCTGCCCAGA ATGCCCTTCG GGAGAGGCTG     120

TGG                                                                  123
```

(2) INFORMATION FOR SEQ ID NO:19:

(i) SEQUENCE CHARACTERISTICS:
       (A) LENGTH: 35 amino acids
       (B) TYPE: amino acid
       (C) STRANDEDNESS: Not Relevant
       (D) TOPOLOGY: Not Relevant (ii) MOLECULE TYPE: protein (xi) SEQUENCE DESCRIPTION: SEQ ID NO:19:

```
Leu Pro Pro Glu Leu Ser Phe Thr Ile Leu Ser Tyr Leu Asn Ala Thr
1               5                  10                  15

Asp Leu Cys Leu Ala Ser Cys Val Trp Gln Asp Leu Ala Asn Asp Glu
            20                  25                  30

Leu Leu Trp
        35
```

(2) INFORMATION FOR SEQ ID NO:20:

(i) SEQUENCE CHARACTERISTICS:
       (A) LENGTH: 105 base pairs
       (B) TYPE: nucleic acid
       (C) STRANDEDNESS: double
       (D) TOPOLOGY: linear (ii) MOLECULE TYPE: other nucleic acid
       (A) DESCRIPTION: /desc = "DNA"

(xi) SEQUENCE DESCRIPTION: SEQ ID NO:20:

```
TTGCCTCCTG AGCTAAGCTT TACCATCTTG TCCTACCTGA ATGCAACTGA CCTTTGCTTG      60

GCTTCATGTG TTTGGCAGGA CCTTGCGAAT GATGAACTTC TCTGG                    105
```

(2) INFORMATION FOR SEQ ID NO:21:

(i) SEQUENCE CHARACTERISTICS:
       (A) LENGTH: 35 amino acids
       (B) TYPE: amino acid

```
            (C) STRANDEDNESS: Not Relevant
            (D) TOPOLOGY: Not Relevant (ii) MOLECULE TYPE: protein (xi) SEQUENCE DESCRIPTION: SEQ ID NO:21:

Leu Pro Pro Glu Leu Ser Phe Thr Ile Leu Ser Tyr Leu Asn Ala Ile
1               5                  10                  15

Asp Leu Cys Leu Ala Ser Cys Val Trp Gln Asp Leu Ala Asn Asp Glu
            20                  25                  30

Leu Leu Trp
        35

(2) INFORMATION FOR SEQ ID NO:22:

(i) SEQUENCE CHARACTERISTICS:
            (A) LENGTH: 105 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:22:

CTGCCTCCTG AGCTGAGCCT CACCATCCTA TCCCACCTGG ATGCAACTGA CCTTTGCCTA       60

GCTTCCTGTG GTTGGCAAGA ACTCGCTAAT GATGAACTTC TCTGG                     105

(2) INFORMATION FOR SEQ ID NO:23:

(i) SEQUENCE CHARACTERISTICS:
            (A) LENGTH: 38 amino acids
            (B) TYPE: amino acid
            (C) STRANDEDNESS: Not Relevant
            (D) TOPOLOGY: Not Relevant (ii) MOLECULE TYPE: protein (xi) SEQUENCE DESCRIPTION: SEQ ID NO:23:

Leu Pro Arg Val Leu Ser Val Tyr Ile Phe Ser Phe Leu Asp Pro Arg
1               5                  10                  15

Ser Leu Cys Arg Cys Ala Gln Val Ser Trp Tyr Trp Lys Ser Leu Ala
            20                  25                  30

Glu Leu Asp Gln Leu Trp
        35

(2) INFORMATION FOR SEQ ID NO:24:

(i) SEQUENCE CHARACTERISTICS:
            (A) LENGTH: 114 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:24:

CTTCCAAGGG TGTTATCTGT CTACATCTTT TCCTTCCTGG ATCCCCGGAG TCTTTGCCGT       60

TGTGCACAGG TGAGCTGGTA CTGGAAGAGC TTGGCTGAGT TGGACCAGCT CTGG           114

(2) INFORMATION FOR SEQ ID NO:25:

(i) SEQUENCE CHARACTERISTICS:
            (A) LENGTH: 38 amino acids
```

(B) TYPE: amino acid
            (C) STRANDEDNESS: Not Relevant
            (D) TOPOLOGY: Not Relevant (ii) MOLECULE TYPE: protein (xi) SEQUENCE DESCRIPTION: SEQ ID NO:25:

Leu Pro Ile Asp Val Gln Leu Tyr Ile Leu Ser Phe Leu Ser Pro His
1               5                  10                  15

Asp Leu Cys Gln Leu Gly Ser Thr Asn His Tyr Trp Asn Glu Thr Val
            20                  25                  30

Arg His Pro Ile Leu Trp
        35

(2) INFORMATION FOR SEQ ID NO:26:

(i) SEQUENCE CHARACTERISTICS:
            (A) LENGTH: 114 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:26:

CTGCCGATTG ATGTACAGCT ATATATTTTG TCCTTTCTTT CACCTCATGA TCTGTGTCAG      60

TTGGGAAGTA CAAATCATTA TTGGAATGAA ACTGTAAGAC ATCCAATTCT TTGG          114

(2) INFORMATION FOR SEQ ID NO:27:

(i) SEQUENCE CHARACTERISTICS:
            (A) LENGTH: 40 amino acids
            (B) TYPE: amino acid
            (C) STRANDEDNESS: Not Relevant
            (D) TOPOLOGY: Not Relevant (ii) MOLECULE TYPE: protein (xi) SEQUENCE DESCRIPTION: SEQ ID NO:27:

Leu Pro Leu Glu Leu Trp Arg Met Ile Leu Ala Tyr Leu His Leu Pro
1               5                  10                  15

Asp Leu Gly Arg Cys Ser Leu Val Cys Arg Ala Trp Tyr Glu Leu Ile
            20                  25                  30

Leu Ser Leu Asp Ser Thr Arg Trp
        35                  40

(2) INFORMATION FOR SEQ ID NO:28:

(i) SEQUENCE CHARACTERISTICS:
            (A) LENGTH: 120 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:28:

CTCCCCTTGG AGCTGTGGCG CATGATCTTA GCCTACTTGC ACCTTCCCGA CCTGGGCCGC      60

TGCAGCCTGG TATGCAGGGC CTGGTATGAA CTGATCCTCA GTCTCGACAG CACCCGCTGG    120

(2) INFORMATION FOR SEQ ID NO:29:

(i) SEQUENCE CHARACTERISTICS:

(A) LENGTH: 33 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:29:

Leu Pro Ala Glu Ile Thr Phe Lys Ile Phe Ser Gln Leu Asp Ile Arg
1               5                   10                  15

Ser Leu Cys Arg Ala Ser Leu Thr Cys Arg Ser Trp Asn Asp Phe Lys
            20                  25                  30

Ser (2) INFORMATION FOR SEQ ID NO:30:

(i) SEQUENCE CHARACTERISTICS:
        (A) LENGTH: 90 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:30:

CTGCCTGCAG AAATCACTTT TAAAATTTTC AGTCAGCTGG ACATTCGGAG TCTGTGCAGG     60

GCTTCATTGA CATGCAGGAG CTGGAATGAC     90

(2) INFORMATION FOR SEQ ID NO:31:

(i) SEQUENCE CHARACTERISTICS:
        (A) LENGTH: 38 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:31:

Leu Pro Leu Leu Gln Gln Pro Leu Leu Cys Ser Val Ala His Pro Ile
1               5                   10                  15

Ala Ser Phe Thr Met Leu Ser Tyr Leu Thr Gly Lys Glu Ala Ala His
            20                  25                  30

Leu Ser Val Glu Leu Trp
        35

(2) INFORMATION FOR SEQ ID NO:32:

(i) SEQUENCE CHARACTERISTICS:
        (A) LENGTH: 114 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:32:

CTGCCATTAC TGCAGCAGCC ACTTCTGTGT TCTGTGGCTC ATCCCATCGC CAGCTTCACC     60

ATGCTGTCAT ACCTCACGGG AAAGGAGGCC GCTCATCTGT CAGTGGAGTT GTGG          114

(2) INFORMATION FOR SEQ ID NO:33:

(i) SEQUENCE CHARACTERISTICS:

```
        (A) LENGTH: 38 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:33:

Leu Pro Asp Ser Leu Val Tyr Gln Ile Phe Leu Ser Leu Gly Pro Ala
1               5                   10                  15

Asp Val Leu Ala Ala Gly Leu Val Cys Arg Gln Trp Gln Ala Val Ser
            20                  25                  30

Arg Asp Glu Phe Leu Trp
            35

(2) INFORMATION FOR SEQ ID NO:34:

(i) SEQUENCE CHARACTERISTICS:
        (A) LENGTH: 114 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:34:

CTCCCCGACA GCCTTGTCTA CCAGATCTTC CTGAGTTTGG GCCCTGCAGA TGTGCTGGCT      60

GCTGGGCTGG TATGCCGCCA ATGGCAGGCT GTGTCCCGGG ATGAGTTCTT ATGG           114

(2) INFORMATION FOR SEQ ID NO:35:

(i) SEQUENCE CHARACTERISTICS:
        (A) LENGTH: 31 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:35:

Leu Pro Glu Glu Val Leu Ala Leu Ile Phe Arg Asp Leu Pro Leu Arg
1               5                   10                  15

Asp Leu Ala Val Ala Thr Arg Val Cys Arg Ala Trp Ala Ala Ala
            20                  25                  30

(2) INFORMATION FOR SEQ ID NO:36:

(i) SEQUENCE CHARACTERISTICS:
        (A) LENGTH: 93 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:36:

CTGCCAGAGG AAGTGTTGGC GCTCATCTTC CGTGACCTGC CTCTCAGGGA CCTTGCTGTA      60

GCCACCAGAG TCTGCAGGGC CTGGGCGGCG GCT                                  93

(2) INFORMATION FOR SEQ ID NO:37:

(i) SEQUENCE CHARACTERISTICS:
        (A) LENGTH: 38 amino acids
        (B) TYPE: amino acid
```

(C) STRANDEDNESS: Not Relevant
            (D) TOPOLOGY: Not Relevant (ii) MOLECULE TYPE: protein (xi) SEQUENCE DESCRIPTION: SEQ ID NO:37:

Leu Pro Ser Val Pro Met Met Glu Ile Leu Ser Tyr Leu Asp Ala Tyr
1               5                   10                  15

Ser Leu Leu Gln Ala Ala Gln Val Asn Lys Asn Trp Asn Glu Leu Ala
            20                  25                  30

Ser Ser Asp Val Leu Trp
        35

(2) INFORMATION FOR SEQ ID NO:38:

(i) SEQUENCE CHARACTERISTICS:
            (A) LENGTH: 114 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:38:

TTACCTAGTG TGCCGATGAT GGAAATCCTC TCCTATCTGG ATGCCTACAG TTTGCTACAG       60

GCTGCCCAAG TGAACAAGAA CTGGAATGAA CTTGCAAGCA GTGATGTCCT GTGG            114

(2) INFORMATION FOR SEQ ID NO:39:

(i) SEQUENCE CHARACTERISTICS:
            (A) LENGTH: 38 amino acids
            (B) TYPE: amino acid
            (C) STRANDEDNESS: Not Relevant
            (D) TOPOLOGY: Not Relevant (ii) MOLECULE TYPE: protein (xi) SEQUENCE DESCRIPTION: SEQ ID NO:39:

Met Pro Ser Glu Ile Leu Val Lys Ile Leu Ser Tyr Leu Asp Ala Val
1               5                   10                  15

Thr Leu Val Cys Ile Gly Cys Val Ser Arg Arg Phe Tyr His Leu Ala
            20                  25                  30

Asp Asp Asn Leu Ile Trp
        35

(2) INFORMATION FOR SEQ ID NO:40:

(i) SEQUENCE CHARACTERISTICS:
            (A) LENGTH: 114 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:40:

ATGCCATCGG AAATCTTGGT GAAGATACTT TCTTACTTGG ATGCGGTGAC CTTGGTGTGC       60

ATTGGATGTG TGAGCAGACG CTTTTATCAT TTGGCTGATG ACAATCTTAT TTGG            114

(2) INFORMATION FOR SEQ ID NO:41:

(i) SEQUENCE CHARACTERISTICS:
            (A) LENGTH: 43 amino acids (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:41:

Leu Pro Met Glu Val Leu Met Tyr Ile Phe Arg Trp Val Val Ser Ser
1               5                   10                  15

Asp Leu Asp Leu Arg Ser Leu Glu Gln Leu Ser Leu Val Cys Arg Gly
            20                  25                  30

Phe Tyr Ile Cys Ala Arg Asp Pro Glu Ile Trp
        35                  40

(2) INFORMATION FOR SEQ ID NO:42:

(i) SEQUENCE CHARACTERISTICS:
        (A) LENGTH: 129 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:42:

CTGCCAATGG AGGTCCTGAT GTACATCTTC CGATGGGTGG TGTCTAGTGA CTTGGACCTC      60

AGATCATTGG AGCAGTTGTC GCTGGTGTGC AGAGGGTTCT ACATCTGTGC CAGAGACCCT    120

GAAATATGG                                                            129

(2) INFORMATION FOR SEQ ID NO:43:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:43:

Leu Ser Leu Val Cys Arg Gly Phe Tyr Ile Cys Ala Arg Asp Pro Glu
1               5                   10                  15

Ile Trp (2) INFORMATION FOR SEQ ID NO:44:

(i) SEQUENCE CHARACTERISTICS:
        (A) LENGTH: 81 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:44:

GACTTGGACC TCAGATCGTT AGAGCAGTTG TCACTGGTGT GCAGAGGATT CTATATCTGT      60

GCCAGAGACC CTGAAATCTG G                                               81

(2) INFORMATION FOR SEQ ID NO:45:

(i) SEQUENCE CHARACTERISTICS:
        (A) LENGTH: 31 amino acids
        (B) TYPE: amino acid (C) STRANDEDNESS: Not Relevant
        (D) TOPOLOGY: Not Relevant (ii) MOLECULE TYPE: protein (xi) SEQUENCE DESCRIPTION: SEQ ID NO:45:

Leu Pro Tyr Glu Leu Ala Ile Asn Ile Phe Xaa Tyr Leu Asp Arg Lys
1               5                   10                  15

Glu Leu Gly Arg Cys Ala Gln Val Ser Lys Thr Trp Glu Gly Asp
            20                  25                  30

(2) INFORMATION FOR SEQ ID NO:46:

(i) SEQUENCE CHARACTERISTICS:
        (A) LENGTH: 93 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:46:

CTGCCTTACG AATTGGCAAT CAATATATTT AGTATCTGGA CAGGAAAGAA CTAGGAAGAT     60

GTGCACAGGT GAGCAAGACG TGGGAAGGTG ATT                                  93

(2) INFORMATION FOR SEQ ID NO:47:

(i) SEQUENCE CHARACTERISTICS:
        (A) LENGTH: 38 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:47:

Leu Pro Leu Glu Leu Lys Leu Arg Ile Phe Arg Leu Leu Asp Val Arg
1               5                   10                  15

Ser Val Leu Ser Leu Ser Ala Val Cys Arg Asp Leu Phe Thr Ala Ser
            20                  25                  30

Asn Asp Pro Leu Leu Trp
        35

(2) INFORMATION FOR SEQ ID NO:48:

(i) SEQUENCE CHARACTERISTICS:
        (A) LENGTH: 114 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:48:

CTCCCATTGG AACTGAAACT ACGGATCTTC CGACTTCTGG ATGTTCGTTC CGTCTTGTCT     60

TTGTCTGCGG TTTGTCGTGA CCTCTTTACT GCTTCAAATG ACCCACTCCT GTGG          114

(2) INFORMATION FOR SEQ ID NO:49:

(i) SEQUENCE CHARACTERISTICS:
        (A) LENGTH: 38 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:49:

Leu Pro Leu Glu Leu Lys Leu Arg Ile Phe Arg Leu Leu Asp Val His
1               5                   10                  15

Ser Val Leu Ala Leu Ser Ala Val Cys His Asp Leu Leu Ile Ala Ser
                20                  25                  30

Asn Asp Pro Leu Leu Trp
            35

(2) INFORMATION FOR SEQ ID NO:50:

(i) SEQUENCE CHARACTERISTICS:
        (A) LENGTH: 114 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:50:

CTTCCACTGG AGCTGAAACT ACGCATCTTC CGACTTTTGG ATGTTCATTC TGTCCTGGCC      60

CTGTCTGCAG TCTGTCATGA CCTCCTCATT GCGTCAAATG ACCCACTGCT GTGG           114

(2) INFORMATION FOR SEQ ID NO:51:

(i) SEQUENCE CHARACTERISTICS:
        (A) LENGTH: 456 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:51:

Ser Ala Met Val Phe Ser Asn Asn Asp Glu Gly Leu Ile Asn Lys Lys
1               5                   10                  15

Leu Pro Lys Glu Leu Leu Leu Arg Ile Phe Ser Phe Leu Asp Ile Val
                20                  25                  30

Thr Leu Cys Arg Cys Ala Gln Ile Ser Lys Ala Trp Asn Ile Leu Ala
                35                  40                  45

Leu Asp Gly Ser Asn Trp Gln Arg Ile Asp Leu Phe Asn Phe Gln Ile
            50                  55                  60

Asp Val Glu Gly Arg Val Val Glu Asn Ile Ser Lys Arg Cys Gly Gly
65                  70                  75                  80

Phe Leu Arg Lys Leu Ser Leu Arg Gly Cys Ile Gly Val Gly Asp Ser
                85                  90                  95

Ser Leu Lys Thr Phe Ala Gln Asn Cys Arg Asn Ile Glu His Leu Asn
                100                 105                 110

Leu Asn Gly Cys Thr Lys Ile Thr Asp Ser Thr Cys Tyr Ser Leu Ser
            115                 120                 125

Arg Phe Cys Ser Lys Leu Lys His Leu Asp Leu Thr Ser Cys Val Ser
        130                 135                 140

Ile Thr Asn Ser Ser Leu Lys Gly Ile Ser Glu Gly Cys Arg Asn Leu
145                 150                 155                 160

Glu Tyr Leu Asn Leu Ser Trp Cys Asp Gln Ile Thr Lys Asp Gly Ile
                165                 170                 175

Glu Ala Leu Val Arg Gly Cys Arg Gly Leu Lys Ala Leu Leu Leu Arg

```
                   180               185               190
Gly Cys Thr Gln Leu Glu Asp Glu Ala Leu Lys His Ile Gln Asn Tyr
            195               200               205
Cys His Glu Leu Val Ser Leu Asn Leu Gln Ser Cys Ser Arg Ile Thr
            210               215               220
Asp Glu Gly Val Val Gln Ile Cys Arg Gly Cys His Arg Leu Gln Ala
225               230               235               240
Leu Cys Leu Ser Gly Cys Ser Asn Leu Thr Asp Ala Ser Leu Thr Ala
                  245               250               255
Leu Gly Leu Asn Cys Pro Arg Leu Gln Ile Leu Glu Ala Ala Arg Cys
              260               265               270
Ser His Leu Thr Asp Ala Gly Phe Thr Leu Leu Ala Arg Asn Cys His
          275               280               285
Glu Leu Glu Lys Met Asp Leu Glu Glu Cys Ile Leu Ile Thr Asp Ser
      290               295               300
Thr Leu Ile Gln Leu Ser Ile His Cys Pro Lys Leu Gln Ala Leu Ser
305               310               315               320
Leu Ser His Cys Glu Leu Ile Thr Asp Asp Gly Ile Leu His Leu Ser
              325               330               335
Asn Ser Thr Cys Gly His Glu Arg Leu Arg Val Leu Glu Leu Asp Asn
              340               345               350
Cys Leu Leu Ile Thr Asp Val Ala Leu Glu His Leu Glu Thr Ala Glu
              355               360               365
Ala Trp Ser Ala Ser Ser Cys Thr Thr Ala Ser Arg Leu Pro Val Gln
        370               375               380
Ala Ser Ser Gly Cys Gly Leu Ser Ser Leu Met Ser Lys Ser Thr Pro
385               390               395               400
Thr Leu Leu Pro Ser Pro His Arg Gln Gln Trp Gln Glu Val Asp Ser
                  405               410               415
Asp Cys Ala Gly Ala Val Ser Phe Ser Asp Ser Ser Cys Leu Gly Pro
              420               425               430
Arg Gly Asp Glu Ala Ser Phe Pro Leu Glu Asp Leu Ser Leu Pro Asp
          435               440               445
Arg Leu His His His Pro Ile Cys
    450               455

(2) INFORMATION FOR SEQ ID NO:52:

(i) SEQUENCE CHARACTERISTICS:
        (A) LENGTH: 1230 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:52:

TTCGGCCATG GTTTTCTCAA ACAATGATGA AGGCCTTATT AACAAAAAGT TACCCAAAGA    60

ACTTCTGTTA AGAATATTTT CCTTCTTGGA TATAGTAACT TTGTGCCGAT GTGCACAGAT   120

TTCCAAGGCT TGGAACATCT TAGCCCTGGA TGGAAGCAAC TGGCAAAGAA TAGATCTTTT   180

TAACTTTCAA ATAGATGTAG AGGGTCGAGT GGTGGAAAAT ATCTCGAAGC GATGCGGTGG   240

ATTCCTGAGG AAGCTCAGCT TGCGAGGCTG CATTGGTGTT GGGGATTCCT CCTTGAAGAC   300

CTTTGCACAG AACTGCCGAA ACATTGAACA TTTGAACCTC AATGGATGCA CAAAAATCAC   360
```

-continued

```
TGACAGCACG TGTTATAGCC TTAGCAGATT CTGTTCCAAG CTGAAACATC TGGATCTGAC      420

CTCCTGTGTG TCTATTACAA ACAGCTCCTT GAAGGGGATC AGTGAGGGCT GCCGAAACCT      480

GGAGTACCTG AACCTCTCTT GGTGTGATCA GATCACGAAG GATGGCATCG AGGCACTGGT      540

GCGAGGTTGT CGAGGCCTGA AAGCCCTGCT CCTGAGGGGC TGCACACAGT TAGAAGATGA      600

AGCTCTGAAA CACATTCAGA ATTACTGCCA TGAGCTTGTG AGCCTCAACT TGCAGTCCTG      660

CTCACGTATC ACGGATGAAG GTGTGGTGCA GATATGCAGG GGCTGTCACC GGCTACAGGC      720

TCTCTGCCTT TCGGGTTGCA GCAACCTCAC AGATGCCTCT CTTACAGCCC TGGGTTTGAA      780

CTGTCCGCGA CTGCAAATTT TGGAGGCTGC CCGATGCTCC CATTTGACTG ACGCAGGTTT      840

TACACTTTTA GCTCGGAATT GCCACGAATT GGAGAAGATG GATCTTGAAG AATGCATCCT      900

GATAACCGAC AGCACACTCA TCCAGCTCTC CATTCACTGT CCTAAACTGC AAGCCCTGAG      960

CCTGTCCCAC TGTGAACTCA TCACAGATGA TGGGATCCTG CACCTGAGCA ACAGTACCTG     1020

TGGCCATGAG AGGCTGCGGG TACTGGAGTT GGACAACTGC CTCCTCATCA CTGATGTGGC     1080

CCTGGAACAC CTAGAAACTG CCGAGGCCTG GAGCGCCTCG AGCTGTACGA CTGCCAGCAG     1140

GTTACCCGTG CAGGCATCAA GCGGATGCGG GCTCAGCTCC CTCATGTCAA AGTCCACGCC     1200

TACTTTGCTC CCGTCACCCC ACCGACAGCA                                      1230
```

(2) INFORMATION FOR SEQ ID NO:53:

(i) SEQUENCE CHARACTERISTICS:
        (A) LENGTH: 380 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:53:

```
Arg Pro Arg Phe Gly Thr Ser Asp Ile Glu Asp Asp Ala Tyr Ala Glu
1               5                  10                  15

Lys Asp Gly Cys Gly Met Asp Ser Leu Asn Lys Phe Ser Ser Ala
            20                  25                  30

Val Leu Gly Glu Gly Pro Asn Asn Gly Tyr Phe Asp Lys Leu Pro Tyr
        35                  40                  45

Glu Leu Ile Gln Leu Ile Leu Asn His Leu Thr Leu Pro Asp Leu Cys
    50                  55                  60

Arg Leu Ala Gln Thr Cys Lys Leu Leu Ser Gln His Cys Cys Asp Pro
65                  70                  75                  80

Leu Gln Tyr Ile His Leu Asn Leu Gln Pro Tyr Trp Ala Lys Leu Asp
                85                  90                  95

Asp Thr Ser Leu Glu Phe Leu Gln Ser Arg Cys Thr Leu Val Gln Trp
            100                 105                 110

Leu Asn Leu Ser Trp Thr Gly Asn Arg Gly Phe Ile Ser Val Ala Gly
        115                 120                 125

Phe Ser Arg Phe Leu Lys Val Cys Gly Ser Glu Leu Val Arg Leu Glu
    130                 135                 140

Leu Ser Cys Ser His Phe Leu Asn Glu Thr Cys Leu Glu Val Ile Ser
145                 150                 155                 160

Glu Met Cys Pro Asn Leu Gln Ala Leu Asn Leu Ser Ser Cys Asp Lys
                165                 170                 175

Leu Pro Pro Gln Ala Phe Asn His Ile Ala Lys Leu Cys Ser Leu Lys
            180                 185                 190
```

```
Arg Leu Val Leu Tyr Arg Thr Lys Val Glu Gln Thr Ala Leu Leu Ser
        195                 200                 205

Ile Leu Asn Phe Cys Ser Glu Leu Gln His Leu Ser Leu Gly Ser Cys
        210                 215                 220

Val Met Ile Glu Asp Tyr Asp Val Ile Ala Ser Met Ile Gly Ala Lys
225                 230                 235                 240

Cys Lys Lys Leu Arg Thr Leu Asp Leu Trp Arg Cys Lys Asn Ile Thr
                245                 250                 255

Glu Asn Gly Ile Ala Glu Leu Ala Ser Gly Cys Pro Leu Leu Glu Glu
                260                 265                 270

Leu Asp Leu Gly Trp Cys Pro Thr Leu Gln Ser Ser Thr Gly Cys Phe
                275                 280                 285

Thr Arg Leu Ala His Gln Leu Pro Asn Leu Gln Lys Leu Phe Leu Thr
        290                 295                 300

Ala Asn Arg Ser Val Cys Asp Thr Asp Ile Asp Glu Leu Ala Cys Asn
305                 310                 315                 320

Cys Thr Arg Leu Gln Gln Leu Asp Ile Leu Gly Lys Val Thr Ile Tyr
                325                 330                 335

Lys Phe Val Leu Asn Val Cys Phe Leu Asp Arg Lys Ala Asn Leu Arg
                340                 345                 350

Leu Phe Val Arg Lys Lys Lys Ile Phe Gly Tyr Asn Lys Asn Phe Ile
                355                 360                 365

Leu Ile Arg Trp Leu Gly Leu Ile Gly Asn Ala Arg
        370                 375                 380

(2) INFORMATION FOR SEQ ID NO:54:

(i) SEQUENCE CHARACTERISTICS:
        (A) LENGTH: 1380 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:54:

AGGCCAAGAT TCGGCACGAG TGATATAGAA GATGATGCCT ATGCAGAAAA GGATGGTTGT      60

GGAATGGACA GTCTTAACAA AAAGTTTAGC AGTGCTGTCC TCGGGGAAGG GCCAAATAAT     120

GGGTATTTTG ATAAACTACC TTATGAGCTT ATTCAGCTGA TTCTGAATCA TCTTACACTA     180

CCAGACCTGT GTAGATTAGC ACAGACTTGC AAACTACTGA GCCAGCATTG CTGTGATCCT     240

CTGCAATACA TCCACCTCAA TCTGCAACCA TACTGGGCAA AACTAGATGA CACTTCTCTG     300

GAATTTCTAC AGTCTCGCTG CACTCTTGTC CAGTGGCTTA ATTTATCTTG GACTGGCAAT     360

AGAGGCTTCA TCTCTGTTGC AGGATTTAGC AGGTTTCTGA AGGTTTGTGG ATCCGAATTA     420

GTACGCCTTG AATTGTCTTG CAGCCACTTT CTTAATGAAA CTTGCTTAGA AGTTATTTCT     480

GAGATGTGTC CAAATCTACA GGCCTTAAAT CTCTCCTCCT GTGATAAGCT ACCACCTCAA     540

GCTTTCAACC ACATTGCCAA GTTATGCAGC CTTAAACGAC TTGTTCTCTA TCGAACAAAA     600

GTAGAGCAAA CAGCACTGCT CAGCATTTTG AACTTCTGTT CAGAGCTTCA GCACCTCAGT     660

TTAGGCAGTT GTGTCATGAT TGAAGACTAT GATGTGATAG CTAGCATGAT AGGAGCCAAG     720

TGTAAAAAAC TCCGGACCCT GGATCTGTGG AGATGTAAGA ATATTACTGA GAATGGAATA     780

GCAGAACTGG CTTCTGGGTG TCCACTACTG GAGGAGCTTG ACCTTGGCTG GTGCCCAACT     840

CTGCAGAGCA GCACCGGGTG CTTCACCAGA CTGGCACACC AGCTCCCAAA CTTGCAAAAA     900
```

```
CTCTTTCTTA CAGCTAATAG ATCTGTGTGT GACACAGACA TTGATGAATT GGCATGTAAT    960

TGTACCAGGT TACAGCAGCT GGACATATTA GGTAAGGTTA CAATATATAA ATTTGTTTTA   1020

AATGTCTGTT TCCTTGACAG AAAAGCCAAT CTCAGACTTT TGTTAGGAA AAAGAAAATT   1080

TTTGGATACA ATAAAAATTT TATCCTGATA AGATGGCTTG GTTTGATAGG AAATGCCAGA   1140

TAGATCAGTT AATATAGGGA ATAATTATAT ATGTACTTTA ATAAAATAGT GAGGACAATA   1200

ACAATTTTAT AGTTGAACTG TAAAAAACTA TAACCATTAA TTCTTGGTCT ACTTGTAAGA   1260

GTGAGAATTT ACATGAGCTG CGCTCTCTAT TTTTATTAAG GAGAGAAGAA ATTAATTCAT   1320

TTGTATAATG AATTCAAGCT AGTTTTTTTT AAGTTTCTTA ATTAAGCGGC CGCAAGCTTA   1380
```

(2) INFORMATION FOR SEQ ID NO:55:

(i) SEQUENCE CHARACTERISTICS:
        (A) LENGTH: 519 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:55:

```
Met Val Ile Met Leu Glx Glu Arg Gln Lys Phe Phe Lys Tyr Ser Val
1               5                   10                  15

Asp Glu Lys Ser Asp Lys Glu Ala Glu Val Ser Glu His Ser Thr Gly
            20                  25                  30

Ile Thr His Leu Pro Pro Glu Val Met Leu Ser Ile Phe Ser Tyr Leu
        35                  40                  45

Asn Pro Gln Glu Leu Cys Arg Cys Ser Gln Val Ser Met Lys Trp Ser
    50                  55                  60

Gln Leu Thr Lys Thr Gly Ser Leu Trp Lys His Leu Tyr Pro Val His
65                  70                  75                  80

Trp Ala Arg Gly Asp Trp Tyr Ser Gly Pro Ala Thr Glu Leu Asp Thr
                85                  90                  95

Glu Pro Asp Asp Glu Trp Val Lys Asn Arg Lys Asp Glu Ser Arg Ala
            100                 105                 110

Phe His Glu Trp Asp Glu Asp Ala Asp Ile Asp Glu Ser Glu Glu Ser
        115                 120                 125

Ala Glu Glu Ser Ile Ala Ile Ser Ile Ala Gln Met Glu Lys Arg Leu
    130                 135                 140

Leu His Gly Leu Ile His Asn Val Leu Pro Tyr Val Gly Thr Ser Val
145                 150                 155                 160

Lys Thr Leu Val Leu Ala Tyr Ser Ser Ala Val Ser Ser Lys Met Val
                165                 170                 175

Arg Gln Ile Leu Glu Leu Cys Pro Asn Leu Glu His Leu Asp Leu Thr
            180                 185                 190

Gln Thr Asp Ile Ser Asp Ser Ala Phe Asp Ser Trp Ser Trp Leu Gly
        195                 200                 205

Cys Cys Gln Ser Leu Arg His Leu Asp Leu Ser Gly Cys Glu Lys Ile
    210                 215                 220

Thr Asp Val Ala Leu Glu Lys Ile Ser Arg Ala Leu Gly Ile Leu Thr
225                 230                 235                 240

Ser His Gln Ser Gly Phe Leu Lys Thr Ser Thr Ser Lys Ile Thr Ser
                245                 250                 255

Thr Ala Trp Lys Asn Lys Asp Ile Thr Met Gln Ser Thr Lys Gln Tyr
```

```
                    260               265                270
Ala Cys Leu His Asp Leu Thr Asn Lys Gly Ile Gly Glu Glu Ile Asp
            275                 280               285

Asn Glu His Pro Trp Thr Lys Pro Val Ser Ser Glu Asn Phe Thr Ser
    290                 295                 300

Pro Tyr Val Trp Met Leu Asp Ala Glu Asp Leu Ala Asp Ile Glu Asp
305                 310                 315                 320

Thr Val Glu Trp Arg His Arg Asn Val Glu Ser Leu Cys Val Met Glu
                325                 330                 335

Thr Ala Ser Asn Phe Ser Cys Ser Thr Ser Gly Cys Phe Ser Lys Asp
            340                 345                 350

Ile Val Gly Leu Arg Thr Ser Val Cys Trp Gln Gln His Cys Ala Ser
            355                 360                 365

Pro Ala Phe Ala Tyr Cys Gly His Ser Phe Cys Cys Thr Gly Thr Ala
            370                 375                 380

Leu Arg Thr Met Ser Ser Leu Pro Glu Ser Ser Ala Met Cys Arg Lys
385                 390                 395                 400

Ala Ala Arg Thr Arg Leu Pro Arg Gly Lys Asp Leu Ile Tyr Phe Gly
                405                 410                 415

Ser Glu Lys Ser Asp Gln Glu Thr Gly Arg Val Leu Leu Phe Leu Ser
            420                 425                 430

Leu Ser Gly Cys Tyr Gln Ile Thr Asp His Gly Leu Arg Val Leu Thr
            435                 440                 445

Leu Gly Gly Gly Leu Pro Tyr Leu Glu His Leu Asn Leu Ser Gly Cys
        450                 455                 460

Leu Thr Ile Thr Gly Ala Gly Leu Gln Asp Leu Val Ser Ala Cys Pro
465                 470                 475                 480

Ser Leu Asn Asp Glu Tyr Phe Tyr Tyr Cys Asp Asn Ile Asn Gly Pro
                485                 490                 495

His Ala Asp Thr Ala Ser Gly Cys Gln Asn Leu Gln Cys Gly Phe Arg
                500                 505                 510

Ala Cys Cys Arg Ser Gly Glu
        515

(2) INFORMATION FOR SEQ ID NO:56:

(i) SEQUENCE CHARACTERISTICS:
        (A) LENGTH: 2276 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:56:

ATGGTAATCA TGCTGTAAGA GCGACAGAAA TTTTTTAAAT ATTCCGTGGA TGAAAAGTCA      60

GATAAAGAAG CAGAAGTGTC AGAACACTCC ACAGGTATAA CCCATCTTCC TCCTGAGGTA     120

ATGCTGTCAA TTTTCAGCTA TCTTAATCCT CAAGAGTTAT GTCGATGCAG TCAAGTAAGC     180

ATGAAATGGT CTCAGCTGAC AAAAACGGGA TCGCTTTGGA AACATCTTTA CCCTGTTCAT     240

TGGGCCAGAG GTGACTGGTA TAGTGGTCCC GCAACTGAAC TTGATACTGA ACCTGATGAT     300

GAATGGGTGA AAAATAGGAA AGATGAAAGT CGTGCTTTTC ATGAGTGGGA TGAAGATGCT     360

GACATTGATG AATCTGAAGA GTCTGCGGAG GAATCAATTG CTATCAGCAT TGCACAAATG     420

GAAAAACGTT TACTCCATGG CTTAATTCAT AACGTTCTAC CATATGTTGG TACTTCTGTA     480
```

```
AAAACCTTAG TATTAGCATA CAGCTCTGCA GTTTCCAGCA AAATGGTTAG GCAGATTTTA     540

GAGCTTTGTC CTAACCTGGA GCATCTGGAT CTTACCCAGA CTGACATTTC AGATTCTGCA     600

TTTGACAGTT GGTCTTGGCT TGGTTGCTGC CAGAGTCTTC GGCATCTTGA TCTGTCTGGT     660

TGTGAGAAAA TCACAGATGT GGCCCTAGAG AAGATTTCCA GAGCTCTTGG AATTCTGACA     720

TCTCATCAAA GTGGCTTTTT GAAAACATCT ACAAGCAAAA TTACTTCAAC TGCGTGGAAA     780

AATAAAGACA TTACCATGCA GTCCACCAAG CAGTATGCCT GTTTGCACGA TTTAACTAAC     840

AAGGGCATTG GAGAAGAAAT AGATAATGAA CACCCCTGGA CTAAGCCTGT TTCTTCTGAG     900

AATTTCACTT CTCCTTATGT GTGGATGTTA GATGCTGAAG ATTTGGCTGA TATTGAAGAT     960

ACTGTGGAAT GGAGACATAG AAATGTTGAA AGTCTTTGTG TAATGGAAAC AGCATCCAAC    1020

TTTAGTTGTT CCACCTCTGG TTGTTTTAGT AAGGACATTG TTGGACTAAG GACTAGTGTC    1080

TGTTGGCAGC AGCATTGTGC TTCTCCAGCC TTTGCGTATT GTGGTCACTC ATTTTGTTGT    1140

ACAGGAACAG CTTTAAGAAC TATGTCATCA CTCCCAGAAT CTTCTGCAAT GTGTAGAAAA    1200

GCAGCAAGGA CTAGATTGCC TAGGGAAAA GACTTAATTG ACTTTGGGAG TGAAAAATCT    1260

GATCAAGAGA CTGGACGTGT ACTTCTGTTT CTCAGTTTAT CTGGATGTTA TCAGATCACA    1320

GACCATGGTC TCAGGGTTTT GACTCTGGGA GGAGGGCTGC CTTATTTGGA GCACCTTAAT    1380

CTCTCTGGTT GTCTTACTAT AACTGGTGCA GGCCTGCAGG ATTTGGTTTC AGCATGTCCT    1440

TCTCTGAATG ATGAATACTT TTACTACTGT GACAACATTA ACGGTCCTCA TGCTGATACC    1500

GCCAGTGGAT GCCAGAATTT GCAGTGTGGT TTTCGAGCCT GCTGCCGCTC TGGCGAATGA    1560

CCCTTGACTT CTGATCTTTG TCTACTTCAT TTAGCTGAGC AGGCTTTCTT TCATGCACTT    1620

TACTCATAGC ACATTTCTTG TGTTAACCAT CCCTTTTTGA GCGTGACTTG TTTTGGCCCC    1680

ATTTCTTACA ACTTCAGAAA TCTTAATTTA CCAGTGAATT GTAATGTTGT TTCTCTTGCA    1740

AATTATACTT TTGGTTTAGA AAGGGATTAG GTCTTTTCAA AAGGGTGAGA ACAGTCTTAC    1800

ATTTTTCTTT TAAATGAAAT GCTTTAAAGA ATGTTGGTAA TGCCATGTCA TTTAAAGTAT    1860

TTCATAGATA ATTTTGAGTT TTAAAGTCCA TGGAGGTGAT TGGTTCTCTT TACACATTAA    1920

CACTGTACCA AGCTTTGCAG ATCTTTTCCG ACACACATGT CTGAAGACTT ATTTTCAAAG    1980

ACAGCACATT TTTGGAAACT AATCTCTTTT CCGTAATATT TCCTTTATTT CAATGATTCT    2040

CAGAAGGCCA ATTCAAACAA ACCCACATTT AAGGTTCTTT AGGATTATAG AATAAATTGG    2100

CTTCTGAGTG TTAGCTCAGT GAGTAGGAAA GCACCAATCG ATATTTGTTT CCTTTAGGGA    2160

TACTTTGTTC TCACCACTGT CCCTATGTCA TCAAATTTGG GAGAGATTTT TTAAAATACC    2220

ACAATCATTT GAAGAAATGT ATAAATAAAA TCTACTTTGA GGACTTTACC AAGTAA        2276
```

(2) INFORMATION FOR SEQ ID NO:57:

(i) SEQUENCE CHARACTERISTICS:
        (A) LENGTH: 39 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:57:

```
Leu Pro Leu Glu Leu Ser Phe Tyr Leu Leu Lys Trp Leu Asp Pro Gln
1               5                   10                  15

Thr Leu Leu Thr Cys Cys Leu Val Ser Lys Gln Trp Asn Lys Val Ile
            20                  25                  30
```

```
Ser Ala Cys Thr Glu Val Trp
        35
```

(2) INFORMATION FOR SEQ ID NO:58:

(i) SEQUENCE CHARACTERISTICS:
        (A) LENGTH: 117 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:58:

```
CTTCCCCTGG AGCTCAGTTT TTATTTGTTA AAATGGCTCG ATCCTCAGAC TTTACTCACA         60

TGCTGCCTCG TCTCTAAACA GTGGAATAAG GTGATAAGTG CCTGTACAGA GGTGTGG          117
```

(2) INFORMATION FOR SEQ ID NO:59:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:59:

```
AATTCGCGCG                                                               10
```

F-BOX GENES AND PROTEINS

This invention was made with government support under National Institutes of Health Grant No. R01AG11085. The Government has certain rights in the invention.

FIELD OF THE INVENTION

The present invention provides compositions and methods for identification of F-box proteins, as well as for drug discovery and assessment. In particular, the present invention provides components of an E3 complex involved in ubiquitination of cell cycle regulators and other proteins, as well as members of a class of proteins that directly function in recognition of ubiquitination targets.

BACKGROUND OF THE INVENTION

The proper development and maintenance of a multicellular organism is a complex process that requires precise spatial and temporal control of cell proliferation. Cell proliferation is controlled via an intricate network of extracellular and intracellular signaling pathways that process growth regulatory signals. This signaling network is superimposed upon the basic cell cycle regulatory machinery that controls particular cell cycle transitions. In eukaryotes, the cell cycle is comprised of an ordered series of discrete events. In contrast to the periodicity of eukaryotic DNA replication and mitosis, cellular growth requires that most metabolic reactions occur continuously. The cell cycle regulatory machinery coordinates the events that occur during the cell cycle, as well as cell growth. Protein degradation is an important aspect of the development and maintenance of multicellular organisms, as it provides direction, order, and the appropriate timing for the key events that occur during the cell cycle.

The problem of how cell division is controlled has long been a topic of intense research. Early models suggested the existence of an initiator that would accumulate during the cell cycle, and induce DNA replication or mitosis when it reached a critical concentration. The mitotic process would then inactivate the initiator, thereby "resetting" the cell cycle. Subsequent research showed that mitotic cyclins accumulate during interphase to drive entry of cells into mitosis. These cyclins are then degraded at the end of mitosis, in order to reset the cycle. Protein degradation has been shown to have a pervasive role in the regulation of cell cycle progression. For example, proteolysis is required for multiple mitotic processes, and for initiating DNA replication (See, King et aL, Science 274:1652–1659 [1996]). Nonetheless, much remains unknown regarding the proteins and the interactions that are involved in the proteolytic regulation of the cell cycle and other processes. Indeed, many proteins are likely to be involved in proteolysis and cellular maintenance (as well as other processes). Such information is needed for the development of compounds to regulate the cell cycle and prevent or treat diseases associated with abnormal cell proliferation.

SUMMARY OF THE INVENTION

The present invention provides compositions and methods for gene identification (e.g., F-box genes), as well as drug discovery and assessment. The present invention provides components of an E3 complex involved in ubiquitination of cell cycle regulators and other proteins, as well as members of a class of proteins that directly function in recognition of ubiquitination targets.

Thus, the present invention provides the function of a class of proteins referred to as F-box proteins in targeted ubiquitination. The present invention finds utility in methods for developing compounds that affect ubiquitination. The present invention also provides numerous novel F-box containing mammalian genes whose encoded proteins are contemplated to function in processes including, but not limited, to targeted ubiquitination of cellular proteins.

The present invention also provides amino acid and DNA sequence information for eighteen novel F-box-containing human or mouse genes. As with Cdc4, Grr1, Skp2, and cyclin F, these novel F-box proteins have the capacity to associate with Skp1 and to simultaneously interact with other proteins through other protein-protein interaction motifs encoded by regions of their genes other than the F-box. Thus, the present invention provides compositions and methods for determining the interaction of these proteins with other proteins.

In one embodiment, the present invention provides an isolated polypeptide comprising at least one functionally active fragment of an F-box protein. In a preferred alternative embodiment, the F-box protein is mammalian, while in a particularly preferred embodiment, the F-box protein is human or murine.

In another embodiment, the functionally active fragment comprises the amino acid sequence selected from the amino acid sequences set forth in SEQ ID NOS:1, 3, 5, 9, 13, 17, 19, 25, 27, 41, 45, 47, 51, 53, 55, and 57, while in alternative embodiment, the functionally active fragment comprises the amino acid sequence selected from the amino acid sequences set forth in SEQ ID NOS:7, 11, 15, 21, 23, 29, 31, 33, 35, 37, 39, 43, and 49.

The present invention also provides a purified antibody which binds specifically to the isolated polypeptide encoding an F-box protein. In one embodiment, the antibody is monoclonal, while in another embodiment, the antibody is polyclonal. In another embodiment, the present invention provides a purified antibody which specifically binds to a complex comprised of an F-box protein and an F-box protein target. In yet another embodiment, the present invention provides an antibody which specifically binds to a complex comprised of an F-box protein and Skp1; it is contemplated that the Skp1 in the complex may be bound to another protein, but such binding is not required.

The present invention also provides an isolated nucleotide sequence encoding at least one functionally active fragment of an F-box protein, wherein the nucleotide sequence encodes at least a portion of an F-box protein. In a preferred embodiment, the F-box protein is mammalian, while in particularly preferred embodiments, the F-box protein is human or murine. In one embodiment, the isolated nucleotide sequence comprises at least a portion of the sequence set forth in SEQ ID NOS:2, 4, 6, 10, 14, 18, 20, 26, 28, 42, 48, 52, 54, 56, and 58. In another embodiment, the isolated nucleotide sequence comprises at least a portion of the sequence set forth in SEQ ID NO:8, 12, 16, 22, 24, 30, 32, 34, 36, 38, 40, 44, and 50.

The present invention also provides a vector comprising a nucleotide sequence, wherein the nucleotide sequence comprises the nucleotide sequence encoding at least one functionally active fragment of an F-box protein, wherein the nucleotide sequence encodes at least a portion of an F-box protein. In one preferred embodiment, the isolated nucleotide sequence comprises at least a portion of the sequence set forth in SEQ ID NOS:2, 4, 6, 10, 14, 18, 20, 26, 28, 42, 48, 52, 54, 56, and 58, while in another preferred embodiment, the isolated nucleotide sequence comprises at least a portion of the sequence set forth in SEQ ID NO:8, 12, 16, 22, 24, 30, 32, 34, 36, 38, 40, 44, and 50.

The present invention also provides a host cell transformed with at least one vector comprising a nucleotide sequence, wherein the nucleotide sequence comprises the nucleotide sequence encoding at least one functionally active fragment of an F-box protein, wherein the nucleotide sequence encodes at least a portion of an F-box protein. In one preferred embodiment, the isolated nucleotide sequence comprises at least a portion of the sequence set forth in SEQ ID NOS:2, 4, 6, 10, 14, 18, 20, 26, 28, 42, 48, 52, 54, 56, and 58, while in another preferred embodiment, the isolated nucleotide sequence comprises at least a portion of the sequence set forth in SEQ ID NO:8, 12, 16, 22, 24, 30, 32, 34, 36, 38, 40, 44, and 50.

The present invention also provides an isolated nucleotide sequence encoding the amino acid sequence selected from group consisting of SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, and 57. In one embodiment, the present invention provides a vector comprising an isolated nucleotide sequence encoding the amino acid sequence selected from group consisting of SEQ ID NOS:1, 3, 5, 7, 9, 11, 13, 15 , 17, 19, 21, 23, 25, 27, 29, 31, 33, 35, 37, 39, 41, 43, 45, 47, 49, 51, 53, 55, and 57. In another embodiment, the present invention provides a host cell transformed with this vector.

The present invention further provides a polynucleotide sequence comprising at least fifteen nucleotides, which hybridizes under stringent conditions to at least a portion of a polynucleotide sequence, wherein the polynucleotide sequence is selected from the polynucleotide sequences set forth in SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, and 58.

The present invention also provides methods for detection of polynucleotides encoding F-box protein in a biological sample comprising the steps of: hybridizing at least a portion of the polynucleotide encoding an F-box protein, to nucleic acid material of a biological sample, thereby forming a hybridization complex; and detecting the hybridization complex, wherein the presence of the complex correlates with the presence of a polynucleotide encoding F-box protein in the biological sample. In one embodiment of the method, prior to hybridization, the nucleic acid material of the biological sample is amplified by the polymerase chain reaction.

The present invention also provides methods for the detection of F-box protein targets comprising the steps of: providing an F-box protein, and a sample suspected of containing an F-box protein target; exposing the F-box protein to the sample under conditions such that the F-box protein binds to the F-box protein target to form an F-box protein and target complex; and detecting the F-box protein and target complex. In one embodiment of the method, the box protein target is selected from the group consisting of cyclins, cyclin-dependent kinases, and IκB. An alternative embodiment further comprises the step of analyzing siad F-box protein and target complex, wherein the analyzing comprises observing the F-box protein and target complex for degradation of the F-box protein target. In another embodiment, the method further comprises the step of exposing the F-box protein and F-box protein target to an F-box protein antagonist. In yet another embodiment of the method, the F-box protein antagonist prevents the formation of the F-box protein and the target complex.

The present invention also provides methods for the detection of an F-box protein and Skp1 complex, comprising the steps of: providing an F-box protein, and Skp1; exposing the F-box protein to Skp1 under conditions such that the F-box protein binds to Skp1 to form an F-box protein and Skp1 complex; and detecting the F-box protein and Skp1 complex. One embodiment of the method further comprises the step of exposing the F-box protein and Skp1 to an F-box protein antagonist. In yet another embodiment of the method, the F-box protein antagonist prevents the formation of the F-box protein and Skp1 complex.

The present invention also provides methods and compositions useful to determine the complexity and diversity of mammalian F-box proteins, as well as the identity of F-box proteins from various species, the protein-protein interaction domains involved, the proteolytic pathways, and regulatory pathways. Indeed, the present invention provides methods and compositions to identify the functions and ubiquitination targets of these and other F-box containing proteins.

However, the present invention is not limited to F-box proteins involved in ubiquitination. Thus, the function of F-box proteins is not necessarily limited to ubiquitination, and the present invention provides the methods and compositions to make this determination. It is contemplated that additional F-box containing genes will be discovered through the use of two-hybrid screens with Skp1 or ubiquitination targets as the two-hybrid "bait" (e.g., as described in the Example 6). It is also contemplated that additional F-box genes will be discovered through sequencing of the mammalian genome and sequence analysis, to determine the homology with existing F-box proteins, such as those identified in the present invention.

The present invention also provide compositions and methods for development of drugs that disrupt at least one pathway in which F-box proteins function, and are required for biological and/or biochemical processes.

The present invention also provides methods and compositions to identify and/or investigate cell cycle regulators, transcription regulators, proteins involved in DNA replication, and other cellular regulatory proteins. It is further contemplated that the present invention finds use in elucidating inflammatory response and infectious disease processes involving protein degradation, as well as development of compounds that control (i.e., either enhance or retard) protein degradation, as appropriate to ameliorate the effects of the inflammatory response or disease process.

The present invention also provides methods and compositions for identifying and investigating the function of protein targets whose abundance is altered in disease, as well as for detection, identification, and characterization of mutations in F-box genes through various methods, including, but not limited sequence analysis, Southern blot analysis of DNA, etc. Furthermore, the present invention also finds use in assessing alterations in cellular protein abundance due to overexpression of particular F-box proteins. It is contemplated that such alterations are associated with particular diseases. The present invention also finds use in determination of overexpression caused by gene amplification in DNA samples from diseased tissue or individuals through such methods as Southern analysis using a particular F-box gene as probe.

It is also contemplated that targets of novel human F-box proteins will be determined by those experienced in the art by approaches including, but not limited to two-hybrid library screens, immunoprecipitation analysis followed by immunoblotting with antibodies against candidate targets, peptide mapping, mass spectral analysis, peptide sequencing, and/or by screening lambda based expression libraries with F-box protein probes.

In addition, the present invention finds use in engineering F-box proteins to artificially recruit particular proteins into an E3 complex for ubiquitination. Thus, it is clear that the present invention provides methods and compositions for detailed investigation of F-box proteins, as well as proteins that associate with F-box proteins. Furthermore, the present invention thereby provides methods and compositions for the detection and analysis of abnormalities in proteolytic functions, as well as methods and compositions for the development of compounds suitable for use in ameliorating such abnormalities.

DESCRIPTION OF THE FIGURES

Unless otherwise indicated, a "P" enclosed within a circle indicates that the protein associated with the symbol is phosphorylated.

FIGS. 1A, 1B and 1C show the assembly of a multiprotein complex containing Cdc34, Cdc53, Skp1, and Cdc3, with each showing the enhancement of the formation of a Cdc53/Cdc4 complex by Skp1. FIG. 1A shows the results of immunoprecipitation with Myc tag on Cdc53 ($Cdc53^M$) using anti-Myc antibodies. FIG. 1B shows the immunoprecipitation results with a Flag tag on Cdc4 ($Cdc4^F$). FIG. 1C shows that Skp1 and Cdc34 can associate with Cdc53 simultaneously.

FIG. 5A is an autoradiograph showing differential recognition of Sic1 and Cln proteins by Grr1 and Cdc4.

FIG. 7 shows the alignment of various F-box proteins provided in the present invention.

DEFINITIONS

Figure 2A:
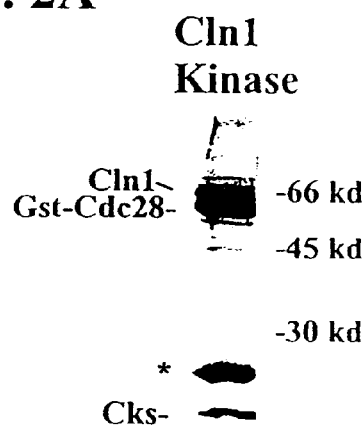
FIG. 2A shows an SDS-PAGE analysis of purified Cln1 HA/Gst-Cdc28HA/Cks1.

To facilitate understanding of the invention, a number of terms are defined below.

As used herein, the term "F-box proteins" refers to the amino acid sequences of substantially purified proteins involved in proteolysis, including but not limited to proteins involved in the ubiquitin-ligase complex obtained from any species, including bovine, ovine, porcine, murine, equine, and human, from any source whether natural, synthetic, semi-synthetic, or recombinant. The F-box is a sequence of 35–45 amino acids and allows the F-box proteins to enter into complexes with Skp1. Thus, the F-box proteins bind Skp1, and contain a motif that displays sequence similarity to Grr1 and Cdc4. This conserved structural motif is included in the sequence alignments shown in FIG. 7 (i.e., the amino acid residues that are shared by the F-box proteins shown). However, it is not intended that the term be limited to the exact sequences set forth in FIG. 7. In some embodiments, the F-box proteins further comprise additional motifs, in particular motifs involved in protein-protein interaction. These additional motifs included, but are not limited to leucine-rich repeats, and WD-40. In preferred embodiments, the F-box protein is mammalian, while in particularly preferred embodiments, the F-box protein is human or murine.

As used herein, the term "F-box target" refers to any moiety that is recognized by at least one F-box containing protein. It is intended that the term encompass such proteins as the cyclins (e.g., A, D, and E), as well as cyclin kinase inhibitors (e.g., p27), and IκB, as well as other proteins. It is not intended that the term be limited to any particular protein or compound.

As used herein, the term "multiprotein complex" refers to complexes comprises more than one protein. It is intended that the term encompass complexes with any number of proteins. In preferred embodiments, the proteins comprising a multiprotein complex function cooperatively. For example, in particularly preferred embodiments of the present invention, Cdc34, Cdc53, Skp1, and Cdc4 comprise a multiprotein complex. It is also intended that the term encompass complexes comprising Skp1, any of the amino acid sequences set forth in Table 2 or Table 4, and a Cdc53 homolog. In preferred embodiments, the Cdc53 homolog in such multiprotein complexes comprises human Cul proteins (e.g., Cul 1 through 5), as well as murine Cul proteins. It is also intended that this term encompass complexes comprised of an F-box protein and its target protein (i.e., an F-box target protein).

The term "modulate," as used herein, refers to a change or an alteration in the biological activity of an F-box protein (e.g., mammalian F-box proteins). Modulation may be an increase or a decrease in protein activity, a change in binding characteristics, or any other change in the biological, functional, or immunological properties of an F-box protein.

The term "mimetic," as used herein, refers to a molecule, the structure of which is developed from knowledge of the structure of an F-box protein, or portions thereof and, as such, is able to effect some or all of the actions of F-box proteins and/or F-box protein-like molecules.

The term "antagonist" refers to molecules or compounds which inhibit the action of a composition (e.g., an F-box protein). Antagonists may or may not be homologous to the targets of these compositions in respect to conformation, charge or other characteristics. In particularly preferred embodiments, antagonists prevent the functioning of F-box proteins. It is contemplated that antagonists may prevent binding of an F-box protein and its target(s). It is also contemplated that antagonists prevent or alter the binding of an F-box protein and Skp1. However, it is not intended that the term be limited to a particular site of function.

The term "derivative," as used herein, refers to the chemical modification of a nucleic acid encoding an F-box protein (in particular, mammalian F-box proteins), or the encoded F-box protein. Illustrative of such modifications would be replacement of hydrogen by an alkyl, acyl, or amino group. A nucleic acid derivative would encode a polypeptide which retains essential biological characteristics of the natural molecule.

A "variant" of an F-box protein, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of a glycine with a tryptophan). Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

"Alterations" in the polynucleotide of for example, SEQ ID NO:4, as used herein, comprise any alteration in the sequence of polynucleotides encoding human F1 Alpha F-box protein, including deletions, insertions, and point mutations that may be detected using hybridization assays. Included within this definition is the detection of alterations to the genomic DNA sequence which encodes an F-box protein (e.g., by alterations in the pattern of restriction fragment length polymorphisms) capable of hybridizing to a particular sequence, the inability of a selected fragment to hybridize to a sample of genomic DNA (e.g., using allele-specific oligonucleotide probes), and improper or unexpected hybridization, such as hybridization to a locus other than the normal chromosomal locus for the polynucleotide sequence encoding an F-box protein (e.g., using fluorescent in situ hybridization [FISH] to metaphase chromosomes spreads).

A "consensus gene sequence" refers to a gene sequence which is derived by comparison of two or more gene sequences and which describes the nucleotides most often present in a given segment of the genes; the consensus sequence is the canonical sequence. In some embodiments, "consensus," refers to a nucleic acid sequence which has been resequenced to resolve uncalled bases, or which has been extended using any suitable method known in the art, in the 5' and/or the 3' direction and resequenced, or which has been assembled from the overlapping sequences of more than one clone using any suitable method known in the art, or which has been both extended and assembled.

The term "sample," as used herein, is used in its broadest sense. The term encompasses biological sample(s) suspected of containing nucleic acid encoding F-box proteins or fragments thereof, and may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

As used herein the terms "protein" and "polypeptide" refer to compounds comprising amino acids joined via peptide bonds and are used interchangeably.

The terms "gene sequences" or "native gene sequences" are used to indicate DNA sequences encoding a particular gene which contain the same DNA sequences as found in the gene as isolated from nature. In contrast, "synthetic gene sequences" are DNA sequences which are used to replace the naturally occurring DNA sequences when the naturally occurring sequences cause expression problems in a given host cell. For example, naturally-occurring DNA sequences encoding codons which are rarely used in a host cell may be replaced (e.g., by site-directed mutagenesis) such that the synthetic DNA sequence represents a more frequently used codon. The native DNA sequence and the synthetic DNA sequence will preferably encode the same amino acid sequence.

As used herein, the term "gene" means the deoxyribonucleotide sequences comprising the coding region of a structural gene and the including sequences located adjacent to the coding region on both the 5, and 3, ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences; these sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA)

transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

As used herein, the term "structural gene" refers to a DNA sequence coding for RNA or a protein. In contrast, "regulatory genes" are structural genes which encode products which control the expression of other genes (e.g., transcription factors).

As used herein the term "coding region" when used in reference to structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

The term "portion," as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:3" encompasses the full-length human F1 protein, and fragments thereof.

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

A "composition comprising a given polynucleotide sequence" as used herein refers broadly to any composition containing the given polynucleotide sequence. The composition may comprise an aqueous solution. Compositions comprising polynucleotide sequences encoding F-box proteins or fragments thereof, may be employed as hybridization probes. In this case, the F-box-encoding polynucleotide sequences are typically employed in an aqueous solution containing salts (e.g., NaCl), detergents (e.g., SDS) and other components (e.g., Denhardt's solution, dry milk, salmon sperm DNA, etc.).

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

A "deletion," as used herein, refers to a change in either amino acid or nucleotide sequence in which one or more amino acid or nucleotide residues, respectively, are absent.

An "insertion" or "addition," as used herein, refers to a change in an amino acid or nucleotide sequence resulting in the addition of one or more amino acid or nucleotide residues, respectively, as compared to the naturally occurring molecule.

A "substitution," as used herein, refers to the replacement of one or more amino acids or nucleotides by different amino acids or nucleotides, respectively.

The term "biologically active," as used herein, refers to a protein having structural, regulatory, or biochemical functions of a naturally occurring molecule. Likewise, "immunologically active" refers to the capability of the natural, recombinant, or synthetic F-box proteins, or any oligopeptide thereof, to induce a specific immune response in appropriate animals or cells and to bind with specific antibodies.

As used herein, the term "purified" or "to purify" refers to the removal of contaminants from a sample. For example, proteins of interest are purified by removal of contaminating proteins; they are also purified by the removal of substantially all proteins that are not of interest. The removal of non-immunoglobulin proteins and/or the removal of immunoglobulins that do not bind protein results in an increase in the percent of protein of interest-reactive immunoglobulins in the sample. In another example, recombinant polypeptides are expressed in bacterial host cells and the polypeptides are purified by the removal of host cell proteins; the percent of recombinant polypeptides is thereby increased in the sample.

The term "substantially purified," as used herein, refers to nucleic or amino acid sequences that are removed from their natural environment, isolated or separated, and are at least 60% free, preferably 75% free, and most preferably 90% free from other components with which they are naturally associated.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule. The term "native protein" as used herein refers to a protein which is isolate from a natural source as opposed to the production of a protein by recombinant means.

As used herein, the term "overproducing" is used in reference to the production of polypeptides in a host cell, and indicates that the host cell is producing more of the polypeptide by virtue of the introduction of nucleic acid sequences encoding the polypeptide than would be expressed by the host cell absent the introduction of these nucleic acid sequences. To allow ease of purification of polypeptides produced in a host cell it is preferred that the host cell express or overproduce the polypeptide at a level greater than 1 mg/liter of host cell culture.

"A host cell capable of expressing a recombinant protein as a soluble protein at a level greater than or equal to X milligrams per 1 OD of cells per liter" is a host cell that produces X milligrams of recombinant protein per liter of culture medium containing a density of host cells equal to 1 $OD_{600}$. The amount of recombinant protein present per OD per liter is determined by quantitating the amount of recombinant protein recovered following affinity purification.

"A host cell capable of secreting a recombinant protein into the culture supernatant at a level greater than or equal to 10 mg recombinant protein per 1 OD of cells per liter" refers to a host cell that secretes a recombinant protein into the culture supernatant (i.e., the medium, such as LB broth, used to grow the host cell) at a level greater than or equal to 10 mg recombinant protein per liter of medium containing a concentration (i.e., density) of host cells equal to 1 $OD_{600}$. The host cells may be grown in shaker flasks (approximately 1 liter culture medium) or in fermentation tank (approximately 10 liters culture medium) and the amount of recombinant protein secreted into the culture supernatant may be determined using a quantitative ELISA assay.

As used herein, the term "fusion protein" refers to a chimeric protein containing the protein of interest (i.e., a ubiquitination complex and/or fragments thereof) joined to an exogenous protein fragment (the fusion partner which consists of a non-ubiquitination complex protein). The fusion partner may enhance solubility of the protein as expressed in a host cell, may provide an "affinity tag" to allow purification of the recombinant fusion protein from the host cell or culture supernatant, or both. If desired, the fusion protein may be removed from the protein of interest prior to immunization by a variety of enzymatic or chemical means known to the art.

As used herein, the term "affinity tag" refers to such structures as a "poly-histidine tract" or "poly-histidine tag," or any other structure or compound which facilitates the purification of a recombinant fusion protein from a host cell, host cell culture supernatant, or both. As used herein, the term "flag tag" refers to short polypeptide marker sequence useful for recombinant protein identification and purification.

As used herein, the terms "poly-histidine tract" and "poly-histidine tag," when used in reference to a fusion protein refers to the presence of two to ten histidine residues at either the amino- or carboxy-terminus of a protein of interest. A poly-histidine tract of six to ten residues is preferred. The poly-histidine tract is also defined functionally as being a number of consecutive histidine residues added to the protein of interest which allows the affinity purification of the resulting fusion protein on a nickel-chelate or IDA column.

As used herein, the term "chimeric protein" refers to two or more coding sequences obtained from different genes, that have been cloned together and that, after translation, act as a single polypeptide sequence. Chimeric proteins are also referred to as "hybrid proteins." As used herein, the term "chimeric protein" refers to coding sequences that are obtained from different species of organisms, as well as coding sequences that are obtained from the same species of organisms.

As used herein, the term "protein of interest" refers to the protein whose expression is desired within the fusion protein. In a fusion protein, the protein of interest will be joined or fused with another protein or protein domain, the fusion partner, to allow for enhanced stability of the protein of interest and/or ease of purification of the fusion protein.

As used herein "soluble" when in reference to a protein produced by recombinant DNA technology in a host cell, is a protein which exists in solution in the cytoplasm of the host cell; if the protein contains a signal sequence, the soluble protein is secreted into the culture medium of eukaryotic cells capable of secretion or by bacterial hosts possessing the appropriate genes. In contrast, an insoluble protein is one which exists in denatured form inside cytoplasmic granules (i.e., inclusion bodies) in the host cell. High level expression (i.e., greater than 1 mg recombinant protein/liter of culture) of recombinant proteins often results in the expressed protein being found in inclusion bodies in the host cells. A soluble protein is a protein which is not found in an inclusion body inside the host cell or is found both in the cytoplasm and in inclusion bodies and in this case the protein may be present at high or low levels in the cytoplasm.

"Peptide nucleic acid$_2$" as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et. al., Anticancer Drug Des., 8:53–63 [1993]).

The term "hybridization" as used herein, refers to any process by which a strand of nucleic acid binds with a complementary strand through base pairing. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation; $T_m = 81.5 + 0.41(\% \text{ G+C})$, when a nucleic acid is in aqueous solution at 1 M NaCl (See e.g., Anderson and Young, Quantitative Filter Hybridization, in *Nucleic Acid Hybridization* (1985). Other references include more sophisticated computations which take structural as well as sequence characteristics into account for the calculation of $T_m$.

The term "hybridization complex," as used herein, refers to a complex formed between two nucleic acid sequences by virtue of the formation of hydrogen binds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0 t$ or $R_0 t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity" as used herein, refer to the natural binding of polynucleotides under permissive salt and temperature conditions by base-pairing For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology," as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence. When used in reference to a single-stranded nucleic acid sequence, the term "substantially homologous" refers to any probe which can hybridize (i.e., it is the complement of) the single-stranded nucleic acid sequence under conditions of low stringency as described.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

Low stringency conditions comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.1% SDS, 5×Denhardt's reagent (50×Denhardt's contains per 500 ml: 5 g Ficoll (Type 400, Pharmacia), 5 g BSA [Fraction V; Sigma]) and 100 µg/ml denatured salmon sperm DNA followed by washing in a solution comprising 5×SSPE, 01% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions which promote hybridization under conditions of high stringency (e.g., increasing the temperature of the hybridization and/or wash steps, the use of formamide in the hybridization solution, etc.).

The term "antisense," as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term also is used in reference to RNA sequences which are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter which permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation. (−) (i.e., "negative") is sometimes used in reference to the antisense strand with the designation (+) sometimes used in reference to the sense (i.e., "positive") strand.

A gene may produce multiple RNA species which are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

"Transformation," as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Thus, the term "stable transfection" or "stably transfected" refers to the introduction and integration of foreign DNA into the genome of the transfected cell. The term "stable transfectant" refers to a cell which has stably integrated foreign DNA into the genomic DNA. The term also encompasses cells which transiently express the inserted DNA or RNA for limited periods of time. Thus, the term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

The term "correlates with expression of a polynucleotide," as used herein, indicates that the detection of the presence of ribonucleic acid that is similar to a particular nucleotide sequence by Northern analysis is indicative of the presence of mRNA encoding an F-box protein in a sample and thereby correlates with expression of the transcript from the polynucleotide encoding the protein.

As used herein, the term "polyA$^+$ RNA" refers to RNA molecules having a stretch of adenine nucleotides at the 3' end. This polyadenine stretch is also referred to as a "poly-A tail". Eukaryotic mRNA molecules contain poly-A tails and are referred to as polyA$^+$ RNA. As used herein, the term "cell culture" refers to any in vitro culture of cells. Included within this term are continuous cell lines (e.g, with an immortal phenotype), primary cell cultures, finite cell lines (e.g., non-transformed cells), and any other cell population maintained in vitro. In particularly preferred embodiments, the cell cultures comprise insect cells.

As used herein, the term "Baculoviridae" refers to the family of viruses that multiply only in invertebrates. Genera of viruses that multiply only in invertebrates are also included in other families (e.g., Iridovirus [Iridoviridae], Entomopoxvirus [Poxviridae], Densovirus [Parvoviridae], cytoplasmic polyhedral virus group [Reoviridae], and Sigmavirus [Rhabdoviridae]). "Baculovirus" refers to viruses that infect insect cells. "Baculovirus-derived vectors" are expression vectors that are derived from baculoviruses; these vectors are commonly used to express foreign genes in insect cells. For example, these vectors find use in expression systems for recombinant proteins that require eukaryotic processing systems. It is intended that the present invention encompass baculovirus-derived vectors, as well as vectors derived from other viruses capable of infecting invertebrate cells. In preferred embodiments, the vectors are used to infect insect cells.

As used herein, the term "selectable marker" refers to the use of a gene which encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity which can be detected in any eukaryotic cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene which is used in conjunction with tk$^-$ cell lines, the CAD gene which is used in conjunction with CAD-deficient cells and the mammalian hypoxanthine-guanine phosphoribosyl transferase (hprt) gene which is used in conjunction with hprt$^-$ cell lines. A review of the use of selectable markers in mammalian cell lines is provided in Sambrook, J. et. a!., *Molecular Cloning: A Laboratory Manual*, 2nd ed., Cold Spring Harbor Laboratory Press, New York (1989) pp.16.9–16.15.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification$_5$ but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g. ELISA, as well as enzyme-based histochemical assays), fluorescent, radioactive, and luminescent systems. It is not intended that the present invention be limited to any particular detection system or label.

As used herein, the term "target" when used in reference to the polymerase chain reaction, refers to the region of nucleic acid bounded by the primers used for polymerase chain reaction. Thus, the "target" is sought to be sorted oat from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular$_5$ the amplified segments created by the PCR process itself are, themselves, efficient templates for subsequent PCR amplifications.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly in the case of T7 RNA polymerase, this amplification enzyme has a stringent specificity for its own promoters (M. Chamberlin et al., Nature 228:227 [1970]). In the case of T4 DNA ligase, the enzyme will not ligate the two oligonucleotides where there is a mismatch between the oligonucleotide substrate and the template at the ligation junction (D. Y. Wu and R B. Wallace, Genomics 4:560 [1989]). Finally, Taq and Pfu polymerases$_5$ by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription (T. Maniatis et al., Science 236:1237 [19871]). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see, S. D. Voss et al., Trends Biochem. Sci., 11:287 [1986]; and T. Maniatis et at, supra). For example, the SV40 early gene enhancer is very active in a wide variety of cell types from many mammalian species, and has been widely used for the expression of proteins in mammalian cells (R. Dijkema et al., EMBO J., 4:761 [1985]). Two other examples of promoter/enhancer elements active in a broad range of mammalian cell types are those from the human elongation factor Iα gene (T. Uetsuki et al., J. Biol. Chem., 264:5791 [1989]; D. W. Kim et al., Gene 91:217 [1990]; and S. Mizushima and S. Nagata, Nuc. Acids Res., 18:5322 [1990]), and the long terminal repeats of the Rous sarcoma virus (C. M. Gorman et al., Proc. Natl. Acad. Sci. USA 79:6777 [1982]), and the human cytomegalovirus (M. Boshart et al.,Cell 41:521 [1985]).

As used herein, the term "promoter/enhancer" denotes a segment of DNA which contains sequences capable of providing both promoter and enhancer functions (i.e., the functions provided by a promoter element and an enhancer element, as discussed above). For example, the long terminal repeats of retroviruses contain both promoter and enhancer functions. The enhancer/promoter may be "endogenous," "exogenous," or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques), such that transcription of that gene is directed by the linked enhancer/promoter.

The presence of "splicing signals" on an expression vector often results in higher levels of expression of the recombinant transcript. Splicing signals mediate the removal of introns from the primary RNA transcript and consist of a splice donor and acceptor site (See e.g., J. Sambrook et at, *Molecular Cloning: A Laboratory Manual*, 2nd ed., Cold Spring Harbor Laboratory Press, New York [1989], pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence," as used herein, denotes a DNA sequence that directs both the termination and polyadenylation of the nascent RNA transcript. Efficient polyadenylation of the recombinant transcript is desirable, as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. An heterologous poly A signal is one which is isolated from one gene and placed 3' to another gene. A commonly used heterologous poly A signal is the SV40 poly A signal. The SV40 poly A signal is contained on a 237 bp BamHI/Bc/I restriction fragment, and directs both termination and polyadenylation (S. Sambrook, supra, at 16.6–16.7).

Eukaryotic expression vectors may also contain "viral replicons," or "viral origins of replication." Viral replicons are viral DNA sequences which allow for the extrachromosomal replication of a vector in a host cell expressing the appropriate replication factors.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "Southern blot" refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (See e.g., J. Sambrook et al, supra at pp 9.31–9-58).

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (See e.g., Sambrook et al., supra at pp. 7.39–7.52).

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is such present in a form or setting that is different from that in which it is found in nature (e.g., in an expression vector). In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acid encoding a mammalian F-box protein includes, by way of example, such nucleic acid in cells ordinarily expressing an F-box protein where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

As used herein, the term "immunogen" refers to a substance, compound, molecule, or other moiety which stimulates the production of an immune response. The term "antigen" refers to a substance, compound, molecule, or other moiety that is capable of reacting with products of the immune response. For example, F-box proteins may be used as immunogens to elicit an immune response in an animal to produce antibodies directed against the subunit used as an immunogen. The subunit may then be used as an antigen in an assay to detect the presence of anti-F-box protein antibodies in the serum of the immunized animal. It is not intended that the present invention be limited to antigens or immunogens consisting solely of one protein (i.e., it is intended that the present invention encompass complexes). Nor is it intended that the present invention be limited to any particular antigens or immunogens.

The term "antigenic determinant," as used herein, refers to that portion of a molecule (i.e., an antigen) that makes contact with a particular antibody (i.e., an epitope). When a protein or fragment of a protein is used to immunize a host animal (e.g., an "immunocompetent" animal with "immunocompetent cells"), numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding," as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

As used herein, the term "antibody" (or "immunoglobulin"), refers to intact molecules as well as fragments thereof, such as Fa, F(ab')$_2$, and Fv, which are capable of binding the epitopic determinant. Antibodies that bind F-box polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The present invention encompasses polyclonal, as well as monoclonal antibodies. The antibodies used in the methods invention may be prepared using various immunogens. In one embodiment, the immunogen is a human F-box protein or subunit (e.g., any of the amino acid sequences set forth in Tables 2 and 4) used as an immunogen) to generate antibodies that recognize human F-box proteins. Such antibodies include, but are not limited to polyclonal, monoclonal, chimeric, single chain, Fab fragments, and an Fab expression library.

Various procedures known in the art may be used for the production of polyclonal antibodies to F-box proteins and subunits. For the production of antibody, various host animals can be immunized by injection with the peptide corresponding to the F-box protein epitope of interest, including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin [KLH]). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies directed toward F-box proteins, any technique that provides for the production of antibody molecules by continuous cell lines in culture may be used (See, e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein, Nature 256:495–497 [1975]), as well as the trioma technique, the human B-cell hybridoma technique (See e.g., Kozbor et al. Immunol. Today 4:72 [1983]), and the EBV-hybridoma technique to produce human monoclonal antibodies (Cole et al., in *Monoclonal Antibodies and Cancer Therapy*, Alan R. Liss, Inc., pp. 77–96 [1985]).

In an additional embodiment of the invention, monoclonal antibodies can be produced in germ-free animals utilizing recent technology (See e.g., PCT/US90/02545). According to the invention, human antibodies may be used and can be obtained by using human hybridomas (Cote et al., Proc. Natl. Acad. Sci. U.S.A.80:2026–2030 [1983]) or by transforming human B cells with EBV virus in vitro (Cole et al., in *Monoclonal Antibodies and Cancer Therapy*, Alan R. Liss, pp. 77–96 [1985]).

According to the invention, techniques described for the production of single chain antibodies (U.S. Pat. No. 4,946,778; herein incorporated by reference) can be adapted to produce F-box protein-specific single chain antibodies. An additional embodiment of the invention utilizes the techniques described for the construction of Fab expression libraries (Huse et al., Science 246:1275–1281 [1989]) to allow rapid and easy identification of monoclonal Fab fragments with the desired specificity for F-box proteins Antibody fragments which contain the idiotype (antigen binding region) of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

In the production of antibodies, screening for the desired antibody can be accomplished by techniques known in the art (e.g., radioimmunoassay, ELISA [enzyme-linked immunosorbant assay], "sandwich" immunoassays, immunoradiometric assays, gel diffusion precipitin reactions, immunodiffusion assays, in situ immunoassays [using colloidal gold, enzyme or radioisotope labels, for example], Western Blots, precipitation reactions, agglutination assays (e.g., gel agglutination assays, hemagglutination assays, etc.), complement fixation assays, immunofluorescence assays, protein A assays, and immunoelectrophoresis assays, etc.

As used herein the term "immunogenically-effective amount" refers to that amount of an immunogen required to invoke the production of protective levels of antibodies in a host upon vaccination.

As used herein, the term "reporter reagent" or "reporter molecule" is used in reference to compounds which are capable of detecting the presence of antibody bound to antigen. For example, a reporter reagent may be a colorimetric substance which is attached to an enzymatic substrate. Upon binding of antibody and antigen, the enzyme acts on its substrate and causes the production of a color. Other reporter reagents include, but are not limited to fluorogenic and radioactive compounds or molecules.

As used herein the term "signal" is used in reference to the production of a sign that a reaction has occurred, for example, binding of antibody to antigen. It is contemplated that signals in the form of radioactivity, fluorogenic reactions, and enzymatic reactions will be used with the present invention. The signal may be assessed quantitatively as well as qualitatively.

GENERAL DESCRIPTION OF THE INVENTION

The present invention provides compositions and methods for gene identification, as well as drug discovery and assessment. The present invention provides components of an E3 complex involved in ubiquitination of cell cycle regulators and other proteins, as well as members of a class of proteins that directly function in recognition of ubiquitination targets. These compositions are involved in protein degradation pathways associated with the eukaryotic cell cycle.

Protein degradation is a commonly employed mechanism for the control of protein abundance. It is also a particularly effective method for promoting unidirectional cell cycle transitions because of its rapidity and irreversibility. Three major transitions (i.e., entry into S phase, separation of sister chromatids, and exit from mitosis), require the degradation of specific proteins via the ubiquitin-26S proteosome pathway (reviewed in King et al., Science 274:1652–1659 [1996]). Ubiquitin is a relatively small protein (approximately 76 amino acid residues) found in all cells of higher organisms. Ubiquitin plays major roles in intracellular protein degradation and histone modification.

Thus, ubiquitination is an important mechanism used to regulate protein abundance. However, until the development of the present invention, the specificity of target selection for ubiquitin dependent proteolysis was largely unknown. Central to this process are the E3s which confer substrate specificity on the ubiquitination reaction and are therefore likely points for regulation. The present invention provides methods for producing ubiquitinated Sic1 in vivo and in vitro using recombinant proteins. The present invention also provides compositions methods for the development of drugs and other compounds effective in correcting abnormalities in protein degradation, based on the demonstration that 1) Cdc53, Skp1, and Cdc4 form a functional E3 ubiquitin ligase complex that works together with the E2 Cdc34 to ubiquitinate Sic1; 2) Cdc4 acts as a receptor for phosphorylated Sic1 recognition; and 3) the sole function Cln/Cdc28 kinases in this process is to phosphorylate Sic1, allowing recognition by Cdc4. Importantly, it was found that distinct F-box proteins can selectively recognize different ubiquitination substrates in a phosphorylation-dependent manner.

The formation of ubiquitin-protein conjugates in protein degradation pathways involves three components that participate in a cascade of ubiquitin transfer reactions: a ubiquitin activating enzyme (E1), a ubiquitin conjugating enzyme (E2), and a specificity factor (E3) (Hershko et al., J. Biol. Chem., 267:8807–8812 [1983]). Ubiquitin is activated as a thiol-ester on E1 in an ATP-dependent reaction, transferred to an E2 as a thiol ester and ultimately conjugated to the target protein in conjunction with an E3, which functions in substrate recognition and in some instances may serve as a thiol-ubiquitin carrier (Scheffner et al., Cell 75:495–505 [1993]; and Scheffner et al., Nature 373:81–83 [1995]). Together, these enzymes polyubiquitinate lysine residues in target proteins through formation of isopeptide bonds with ubiquitin, leading to recognition by the 26S proteosome. This association eventually results in the degradation of the target protein.

While E1 and E2 proteins can be identified through sequence similarity, this is not yet generally true for E3 proteins. Thus, the present invention provides previously unreported methods and compositions. This is significant as the identity of E3 components are a central issue in cell cycle control because they are potential regulators of both the timing of ubiquitination and the selection of substrates. Prior to the development of the present invention, much of the prior knowledge of E3s was provided by analysis of the HECT domain protein E6-AP which functions as a ubiquitin-ligase for p53, (Huibregtse et al., Proc. Natl. Acad. Sci. USA 92:2563–2567 [1995]; and Scheffner et al., Nature 373:81–83 [1995]); and the anaphase promoting complex (APC), which functions in the destruction of mitotic cyclins and proteins involved in sister chromatid cohesion (reviewed in King et al., [1996] supra). These APC substrates contain a destruction box motif, although precisely how the timing and selection of substrates by the APC is achieved is unknown. In contrast, timing of ubiquitination of a variety of non-APC substrates is thought to be regulated in part by the phosphorylation of the substrate itself. PEST sequences (i.e., sequences that are rich in proline, glutamic acid, serine and threonine) are frequently found in unstable proteins such as cyclins and contain sites of phosphorylation (Rogers et al., Science 234:364–368 [1986]). Phosphorylation of specific residues has been implicated in the destruction of G1 cyclins in yeast and mammalian cells (Tyers et al., EMBO J., 11:1773–84 [1992]; Lanker et al., Science 271:1597–1601 [1996]; Clurman et al., Genes Dev., 10:1979–1990 [1996]; Diehl et al., Genes Dev., 11:957–972 [1997]; and Won and Reed, EMBO J., 15:4182–4193 [1996]), and the cyclin-kinase inhibitor (CKI) p27 (Sheaff et al., Genes Dev., 11:1464–1478 [1997]).

In *S. cerevisiae*, entry into S-phase requires activation of the Cdc28 kinase by G1 cyclins (Cln1, Cln2, and Cln3) and S-phase cyclins (Clb5 and Clb6) (Nasmyth, Curr. Opin. Cell Biol., 5:166–179 [1993]). Although both Cln/Cdc28 and Clb/Cdc28 complexes assemble during G1, Clb/Cdc28 is sequestered in an inactive form through association with the CK1 p40Sic1 (Mendenhall, Science 259:216–219 [1993]; and Schwob et. al., Cell 79: 233–244 [1994]). Sic1 levels vary in the cell cycle, sharply decreasing at the G1/S transition, and this correlates with activation of Clb5/Cdc28. The decrease in Sic1 levels depends on the E2 Cdc34, suggesting that ubiquitination triggers Sic1 destruction (Schwob et al., Cell 79:233–244 [1994]). Sic1 destruction also requires CLN and CDC28 function; elimination of Sic1 defines the threshold requirement for Cln/Cdc28 activity in S-phase entry (Schneider et al., Science 272: 560–562 [1996]; Schwob et al., [1994], supra; and Tyers, Proc. Natl. Acad. Sci. U.S.A. 93:7772–7776 [1996]). Although Sic1 is a phosphoprotein (Schneider et al., Science 272:560–562 [1996]), it is not known whether Cln/Cdc28 complexes directly phosphorylate Sic1 or whether phosphorylation plays another, perhaps indirect, role in Sic1 destruction. The development of the present invention provides methods and compositions to resolve these questions.

Three other genes, SKP1, CDC53, and CDC4, are also required for S-phase entry (Schwob et al., 1994, supra, and Bai et al., Cell 86:263–274 [1996]). These genes, together with CDC34, show a pattern of suppression and enhancement consistent with roles in a common process; conditional alleles of these genes cause arrest with unreplicated DNA and multiple buds (Yochem and Byers, J. Mol. Biol., 195:233–245 [1987]; Goebl et al., J. Mol. Biol., 195:233–245 [1988]; Bai et al., [1996] supra; and Mathias et al., Mol. Cell. Biol., 16:6634–6643 (1996]). Sic1 accumulates in cdc34-1, cdc4-1, or skp 1-11 mutants, and deletion of SIC1 allows such mutants to undergo DNA synthesis (Schwob et al., [1996], supra; and Bai et al., [1996], supra). Components of the Cdc34 pathway have also been implicated in the destruction of a number of other important regulatory proteins, including Cln2 (Deshaies et al., EMBO J., 14:303–312 [1995]; Bai et al., [1996] supra; and Willems et al., Cell 86:453–463 [1996]), Cdc6 (Piatti et al., Genes Dev., 10:1516–1531 [1996]), the CKIs Rum1 and Far1 (McKinney et al., Genes Dev., 7:833–843 [1993]; and Kominami and Toda, Genes Dev., 11:1548–1560 [1997]), and the transcription factor Gcn4 (Komitzer et al, EMBO J., 33:6021–6030 [1994]). Thus, it is contemplated that Cdc34, Cdc53, Skp1, and Cdc4 are utilized for the destruction of diverse regulatory proteins. A requirement for Cdc34 for Cln2 ubiquitination has been demonstrated in crude yeast lysates (Deshaies et al., [1995], supra), but this requirement has been suggested to be indirect (Blondel and Mann, Nature 384:279–282 [1996]). Interestingly, SKP1 is also required for the G2/M transition (Bai et al., [1996], supra; and Connelly and Heiter, Cell 86:275–285 [1996]), and has been found to be a component of the kinetochore complex CBF3 (Connelly and Fleiter, Cell 86:275–285 [1996], supra; and Stemmann and Lechner, EMBO J., 15:3611–3620 [1996]).

Skp1 binds to Cdc4, and this interaction involves a motif in Cdc4 referred to as the F-box (Bai et al., [1996], supra). The F-box motif is found in a large number of proteins including cyclin F (Bai et al., EMBO J., 15:3611–3620 [1994]) and the cyclin A/Cdk2-associated protein Skp2 (Zhang et al., Cell 82:915–925 [1995]), both of which bind Skp1. The two largest classes of F-box proteins either contain WD-40 repeats (e.g., Cdc4) or leucine-rich repeats (LRR) (e.g., Skp2 and Grr1) (Bai et al., [1996], supra). GRR1 was initially identified as a gene required for glucose repression (Flick and Johnston, Mol. Cell. Biol., 11:5101–12 [1991]) but was later also found to be involved in Cln destruction (Barral et al., Genes Dev., 9:399–409 [1995]). The discovery that Skp1 is required for the destruction of both Sic1 and Cln2, while Cdc4 and Grr1 were only implicated in the destruction of one of these, led to development of one embodiment of the present invention (i.e., one model) in which F-box proteins function to recognize targets for ubiquitination, and Skp1 links these F-box/target complexes to the ubiquitination machinery.

The present invention was developed in a stepwise fashion, with an important aspect being the elucidation of the role of Skp1 and F-box proteins in ubiquitination through in vitro reconstruction of the Sic1 ubiquitination pathway. Sic1 ubiquitination was found to depend upon each of the proteins implicated in Sic1 destruction in vivo. For example, Skp1 recruits Cdc4 into a Cdc53/Cdc34 complex, and enhances recognition of Sic1 by Cdc4, with the latter interaction requiring Sic1 phosphorylation. In contrast, Grr1 does not interact with Sic1, but does recruit phosphorylated Cln1 and Cln2 into Skp1/Cdc53 complexes. Thus, the present invention provides F-box proteins that function as receptors, which recruit substrates into a Skp1/Cdc53/Cdc34 complex for ubiquitination by Cdc34.

Thus, the present invention provides the function of a class of proteins referred to as F-box proteins in targeted ubiquitination. The present invention finds utility in methods for developing compounds that affect ubiquitination. The present invention also provides numerous novel F-box containing mammalian genes whose encoded proteins are contemplated to function in processes including, but not limited, to targeted ubiquitination of cellular proteins. Specifically, F-box proteins function as receptors for proteins to be ubiquitinated.

As described in the Examples, through a series of experiments using a set of defined proteins found in *S. cerevisiae*, it was demonstrated that three proteins (i.e., Cdc53, Skp1, and the F-box protein Cdc4) form a complex referred to as an "E3" which functions together with an E1 ubiquitin activating enzyme, and the E2 ubiquitin conjugating enzyme Cdc34, to ubiquitinate the Cdk inhibitor Sic1. Recognition of Sic1 by this E3 complex requires that Sic1 be specifically phosphorylated and phosphorylation may be a general mechanism used to regulate the timing of ubiquitination of target proteins. Thus, it is contemplated that compounds that alter this phosphorylation will in turn, alter the timing of ubiquitination of target proteins. Such compounds are contemplated as possible drugs that disrupt at least one pathway in which F-box proteins function, and are required for biological and/or biochemical processes.

Cdc53 was found to function as an adapter and link Skp1 to the E2, while Skp1 was found also to function as an adapter and links Cdc53 to the F-box protein Cdc4. Cdc4 was found to function as an adapter to link ubiquitination targets (e.g., Sic1) to the Skp1/Cdc53/Cdc34 complex. E1 is not a stable component of the ubiquitination complex, but is required for ubiquitination of the target protein. The F-box protein contains minimally two protein-protein interaction domains. The F-box is a sequence of 35–45 amino acids and allows the F-box proteins to enter into complexes with Skp1. F-box proteins also contain additional domains, typically, but not necessarily C-terminal to the F-box sequence, which based on the results with Cdc4 function as recognition components for ubiquitination substrates. Cdc4 contains C-terminal WD-40 repeats. Another F-box protein (Grr1) contains leucine rich repeats which are protein-protein interaction domains. Because Skp1 simultaneously forms complexes with Cdc53 proteins and an F-box protein, these interactions give rise to formation of an E3 complex. Any particular F-box protein may interact simultaneously with both Skp1 and at least one ubiquitination target. F-box proteins may have a single ubiquitination target but it is contemplated that they (i.e., at least some F-box proteins) also have multiple in vivo ubiquitination targets. For example, the data obtained for Cdc4 indicate that it is involved in the destruction of at least two proteins, Sic1 and Cdc6. Thus, the present invention provides the necessary components and methods to alter ubiquitination of target proteins through the use of new drugs or other compounds.

Based on the sequence of the yeast genome, it was determined that *S. cerevisiae* contains nine F-box proteins. To date, three of these (CDC4, GRR1, and MET30), have been analyzed genetically. CDC4 is required for the destruction of Sic1 and Cdc6, while Grr1 is required for the destruction of the G1 (Cln) cyclins, and MET30 is required for proper control of methionine biosynthetic pathways and is predicted to control the abundance of Met4.

The present invention also provides methods and compositions useful to determine the complexity and diversity of mammalian F-box proteins, as well as the identity of F-box proteins from various species, the protein-protein interaction domains involved, the proteolytic pathways, and regulatory pathways. For example, the mammalian proteins (cyclin F, Skp2) contain an F-box and associate with Skp1, but their functions and ubiquitination targets have not been demonstrated. Cyclin F contains a cyclin box motif C-terminal to the F-box. Skp2 contains a leucine rich motif C-terminal to its F-box. Mouse MD6, an additional mammalian F-box containing protein; X54352) is in Genbank but its function is unknown. The present invention provides human MD6, with the following sequences:

LPLELSFYLLKWLDPQTLLTC-
CLVSKQWNKVISACTEVW (SEQ ID NO:57); and
CTTCCCCTGGAGCTCAGTTTTTATTTGT-
TAAAATGGCTCGATCCTCAGACTTTA CTCA-
CATGCTGCCTCGTCTCTAAACAGTG-
GAATAAGGTGATAAGTGCCTGTAC
AGAGGTGTGG (SEQ ID NO:58; AA252600).

Furthermore, the closest homolog of MD6 is MET30; it is contemplated that MD6 plays a homologous role in methionine biosynthesis in eukaryotes. The present invention provides methods and compositions to identify the functions and ubiquitination targets of these and other F-box containing proteins.

The present invention also provides amino acid and DNA sequence information for eighteen novel F-box-containing human or mouse genes. As with Cdc4, Grr1, Skp2, and cyclin F, these novel F-box proteins have the capacity to associate with Skp1 and to simultaneously interact with other proteins through other protein-protein interaction motifs encoded by regions of their genes other than the F-box. Thus, the present invention provides compositions and methods for determining the interaction of these proteins with other proteins.

Mammalian Skp1, by analogy with budding yeast, functions as an adapter linking Skp1 to an E2. It is contemplated that cellular proteins brought into complexes containing Cdc53 and Skp1 by any one of these novel F-box proteins has the potential to be ubiquitinated by an E2 (e.g., Cdc34) in combination with an E1. It is further contemplated that interaction with an F-box protein may also produce an alternative regulatory function (e.g., altering subcellular localization of the associated protein). Thus, the function of F-box proteins is not necessarily limited to ubiquitination, and the present invention provides the methods and compositions to make this determination. It is contemplated that additional F-box containing genes will be discovered through the use of two-hybrid screens with Skp1 or ubiquitination targets as the two-hybrid "bait" (e.g., as described in the Example 6). It is also contemplated that additional F-box genes will be discovered through sequencing of the mammalian genome and sequence analysis, to determine the homology with existing F-box proteins, such as those identified in the present invention.

For example, it is contemplated that cell cycle regulators such as cyclins and cyclin-kinase inhibitors, transcription regulators, proteins involved in DNA replication, and other cellular regulatory proteins will be identified and/or investigated using the methods and compositions provided by the present invention. It is further contemplated that the present invention will find use in elucidating inflammatory response and infectious disease processes involving protein degradation, as well as development of compounds that control (i.e., either enhance or retard) protein degradation as appropriate, to ameliorate the effects of the inflammatory response or disease process.

Thus, it is also contemplated that F-box proteins are involved in regulatory pathways important for cellular homostasis and/or growth control. In this context, F-box proteins may be involved in the elimination or modification of proteins which positively or negatively regulate the cell cycle, which positively or negatively regulate transcription, or which positively or negatively regulate the abundance of a protein involved in a signaling pathway. Elimination of proteins could be mediated by the 26S proteosome after targeted ubiquitination by a E3 complex containing an F-box protein. Ubiquitination without proteolytic destruction may alter the activity of the target protein either positively or negatively. Thus, it is contemplated that molecules that alter the activities or target specificities of F-box proteins, or the ability of F-box proteins to enter into macromolecular complexes such as E3 complexes composed of and F-box protein, a Cdc53 homolog and Skp1, will find utility as pharmaceutical agents for a variety of diseases. The present invention provides the compositions and methods for the identification of molecules (including but not limited to proteins, peptides, naturally occuring alkaloids, and synthetic alkaloids) which alter the activities, levels, or targets of F-box proteins.

For example, disruption of the F-box protein/Skp1 complex is achieved using synthetic molecules, proteins, or peptides which mimic the F-box sequence or its three dimensional structure and block association of any F-box protein with Skp1. It is contemplated that blockage of this interaction renders the F-box protein non-functional with respect to ubiquitination of its target proteins. Similarly, disruption of such complexes is also achieved with synthetic molecules, proteins, or peptides which specifically bind the F-box of a particular F-box protein. This approach provides specificity for a particular pathway involving a specific F-box. These classes of molecules can be identified using various methods, including, but not limited to, peptide phage display libraries to identify peptide sequences that bind either an F-box sequence of a specific domain in Skp1 involved in interaction with the F-box. In this method, F-box sequences or Skp1 sequences are immobilized on solid supports such as a magnetic bead through the use of biotinylated F-box or Skp1 sequences and streptavidin coated magnetic beads. Phage display libraries are then bound to the coated magnetic beads and phage binding the beads are isolated and analyzed for binding sequences.

A similar method involves the use of two-hybrid screens to identify proteins or fragments of proteins that bind Skp1 or the F-box sequence. Such molecules find use in blocking assembly of Skp1/F-box protein complexes in vivo and are useful (either directly or as precursors) in the generation of pharmacological agents.

In another embodiment, disruption of F-box/target interactions are also contemplated. In addition to the F-box, F-box containing proteins may also contain an additional interaction domain including but not limited to WD-40 or leucine rich repeats. For example, F1Alpha and F2 Beta contain leucine rich repeats. Embodiments of the present invention provide methods to identify targets of F-box proteins which include, but are not limited to cyclins, cell cycle regulators, cyclin-kinase inhibitors, β-catenin, IκB, and transcriptional regulators. It is contemplated that molecules which either block, enhance, or otherwise facilitate association of any target with any F-box protein are useful as pharmaceutical agents in the treatment of human diseases. The approaches described herein provide examples of approaches that would yield peptides, proteins, and naturally occuring or synthetic molecules which can bind target recognition motifs in F-box proteins or motifs in the target protein responsible for recognizing the F-box protein. It is also contemplated that molecules which bind these domains block complex formation and thereby block, accelerate, or alter the normal function of the F-box protein, which may include (depending upon the particular F-box protein), but is not limited to ubiquitination.

The present invention also provides experimental strategies to determine whether molecules identified in these ways can block complex assembly. It is contemplated that binding assays based on immobilized Skp1 and soluble F-box protein (or vice versa), or immobilized F-box protein and soluble target (or vice versa), will be developed in a manner similar to the development of embodiments of the present invention (i.e., with Skp1, Cdc4 [an F-box protein] and Sic1 [the target of Cdc4]). Molecules to be tested for their ability to alter either Skp1/F-box protein interaction or F-box protein/target interaction may be added to binding reactions and the effects of the added agent examined by determining the fraction of soluble protein bound relative to that bound in the absence of the agent. It is also contemplated that such an assay be adapted to high throughput screening strategies through the use of radiolabeled or otherwise tagged soluble binding protein.

The present invention also provides evidence for phosphorylation specific recognition of target proteins and methods for determining whether recognition of the target requires that the target be phosphorylated. It is contemplated that agents that block or enhance specific phosphorylation of target proteins to allow recognition by F-box proteins will be identified through approaches disclosed herein. It is contemplated that such agents will find use as pharmaceutical agents that increase or decrease the rate of ubiquitination of target proteins.

In addition, the present invention finds use in the identification and development of compounds effective against viral infection and disease. For example, two viral proteins (adenovirus E3-12.9K and baculovirus ORF11), appear to essentially encode only an F-box, and a SKP1-related gene is present in Chorella virus. As viruses subvert the cell cycle in order to replicate, it is contemplated that disruption of the ubiquitin-mediated proteolysis pathway would also disrupt viral replication. It is possible that F-box containing viruses can inhibit degradation of specific protein subsets (e.g., cyclins) to enhance their replication, or promote the degradation of specific inhibitory proteins. It is also possible that these proteins may target the destruction of proteins that inhibit or kill the virus. The present invention finds use in development of compositions and methods to inhibit viral replication by interfering with the ubiquitin-mediated proteolysis pathway utilized by the virus, as well as by upregulating the cellular machinery to enhance proteolysis of viral components. In particular, the present invention finds use in identification and development of compounds effective against immunodeficiency viruses (e.g., human immunodeficiency virus, as well as other viruses such as feline immunodeficiency virus, bovine immunodeficiency virus, and simian immunodeficiency virus).

It is further contemplated that targets of novel human F-box proteins will be determined by those experienced in the art by approaches including, but not limited to two-hybrid library screens, immunoprecipitation analysis followed by immunoblotting with antibodies against candidate targets, peptide mapping, mass spectral analysis, peptide sequencing, and/or by screening lambda based expression libraries with F-box protein probes.

The present invention also finds use in investigating the function and methods of altering protein targets whose abundance is altered in disease. For example, cyclins are frequently overexpressed in cancer cells. Thus, mutations in F-box proteins involved in cyclin destruction will lead to cyclin accumulation; such cyclin accumulation may promote inappropriate cell division characteristic of cancer. The present invention also finds utility in the identification of mutations in F-box genes through various methods, including, but not limited sequence analysis, Southern blot analysis of DNA, etc. Furthermore, the present invention also finds use in assessing alterations in cellular protein abundance due to overexpression of particular F-box proteins. It is contemplated that such alterations are associated with particular diseases. The present invention also finds use in determination of overexpression caused by gene amplification in DNA samples from diseased tissue or individuals through such methods as Southern analysis using a particular F-box gene as probe.

Furthermore, the present invention thereby provides methods and compositions for the detection and analysis of abnormalities in proteolytic functions, as well as methods and compositions for the development of compounds suitable for use in ameliorating such abnormalities.

DETAILED DESCRIPTION OF THE INVENTION

As discussed above, the present invention provides compositions and methods for gene identification and characterization, as well as drug discovery and assessment. In particular, the present invention provides components of an E3 complex involved in ubiquitination of cell cycle regulators and other proteins, as well as members of a class of proteins that directly function in recognition of ubiquitination targets (i.e., F-box proteins). These compositions are involved in protein degradation pathways associated with the eukaryotic cell cycle.

Assembly of a Complex Containing Cdc53/Skp1/ Cdc4 and the E2 Cdc34

Strong genetic evidence implicated Cdc34, Cdc53, Skp1, and Cdc4 as molecules involved in the control of S-phase entry through destruction of Sic1. In preliminary work, SKP1 and CDC4 were found to show reciprocal overproduction suppression of their respective temperature sensitive mutants and that Cdc4 physically associated with Skp1. A further search for suppressors using a GAL-driven cDNA library revealed that CDC53 overexpression suppresses skp1-11. These observations, coupled with genetic and physical evidence of a Cdc53/Cdc34 interaction resulted in the development of embodiments of the present invention.

The first step in assembling the complexes of interest involved co-infection of insect cells with various baculovirus expression vectors. Insect cells were co-infected with various combinations of baculoviruses expressing Myc-tagged Cdc53 (Cdc53$^M$), Cdc34, Cdc4, and Skp1. Anti-Myc immune complexes from lysates of these infected cells were immunoblotted to identify associated proteins (See, FIG. 1A). As shown in FIG. 1A, in the presence of all four proteins, anti-Cdc53$^M$ complexes contained Cdc4, Cdc34, and Skp1 (FIG. 1A, lane 5). However, in the absence of Skp1, only low levels of Cdc4 were found to bind with Cdc53$^m$, regardless of the presence of Cdc34 (See, FIG. 1A, lanes 7 and 8). To confirm this result, the association of Cdc53$^M$ with anti-Cdc4$^F$ immune complexes was analyzed. These results indicated the association of Cdc53$^M$ with anti-Cdc4$^F$ immune complexes was also greatly enhanced in the presence of Skp1 (See, FIG. 1B). Thus, one function of Skp1 is to facilitate association of Cdc53 with Cdc4. In contrast to Cdc4, both Skp1 and Cdc34 were shown to associate with Cdc53$^M$ in the absence of other yeast proteins (See, FIG. 1A). Furthermore, it appeared that Cdc53 can simultaneously associate with both Cdc34 and Skp1, as the association of Gst-Skp1 with Cdc34 is enhanced in the presence of Cdc53$^M$ (See, FIG. 1C). These data indicated that Cdc34 Cdc53, Skp1, and Cdc4 form a multiprotein complex.

Phosphorylation of Sic1 by Cln/Cdc28 is Required for its Recognition by a Cdc4/Skp1/Cdc53 Complex While previous studies implicated involvement of Cln/Cdc28-dependent phosphorylation in Sic1 degradation (Schwob et al., Cell 79:233–244 [1994]; Schneider et al., Science 272:560–562 [1996]; and Tyers, Proc. Natl. Acad. Sci. U.S.A. 93:7772–7776 [1996]), until the development of the present invention, it was not clear whether Sic1 was directly phosphorylated by Cln/Cdc28, or whether this phosphorylation was correlative or causative for subsequent Sic1 degradation (and if causative, whether this modification played a role in Sic1 recognition by the ubiquitination machinery). Nor was it known whether Cln/Cdc28 might also directly regulate the activity of the ubiquitination machinery. Once the methods to generate and purify Cln1/Gst-Cdc28 and Sic1/Clb5/Gst-Cdc28 complexes from insect cells were established in vitro during the development of the present invention, the determination was made as to whether any of these components might function in Sic1 recognition, and if Sic1 phosphorylation plays a role in this process. This aspect of the present invention finds use in providing methods for the development of drugs or other compounds suitable for prevention and/or treatment of cancers (i.e., uncontrolled cellular growth), as well as treatment of other diseases associated with abnormalities in cell cycle control.

Figure 2B:
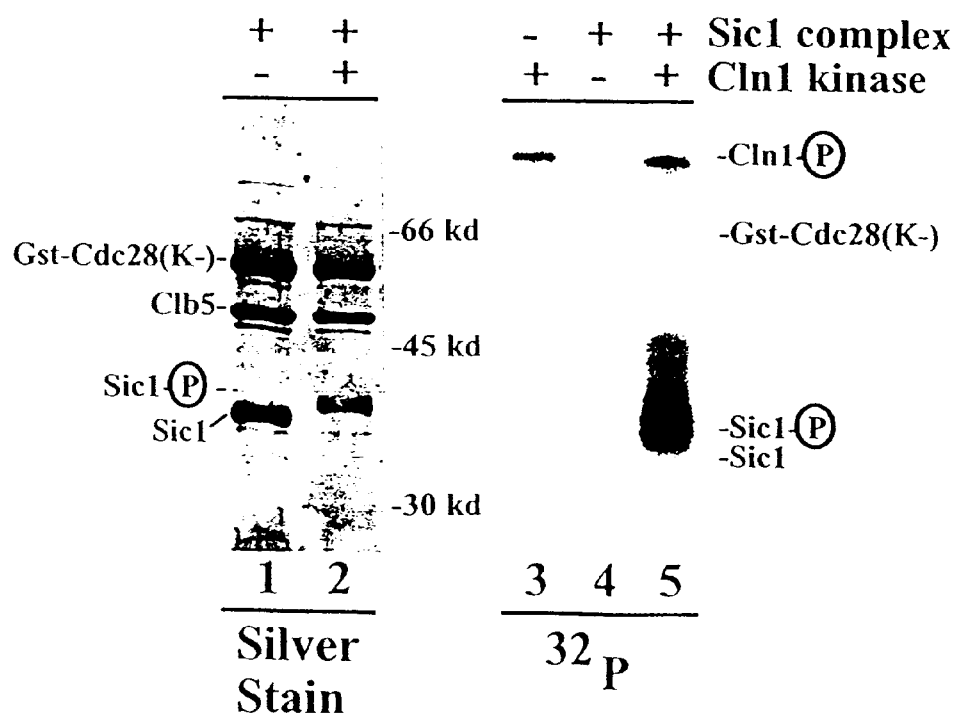
FIG. 2B is an autoradiograph showing the phosphorylation of Sic1 by Cln1/Cdc28 complexes in vitro.

In order to accomplish this, Sic1 was purified to near homogeneity from insect cells by virtue of its association with Clb5/Gst-Cdc28 complexes (See, FIG. 2B). Initially, it was believed that such a complex would represent the primary form of Sic1 ubiquitinated in vivo. However, it was found that uninhibited Clb5/Cdc28 in these preparations phosphorylated Sic1, making it impossible to directly assess the role of specific phosphorylation by Clns. Therefore, a kinase-impaired Gst-Cdc28(K–) containing a mutation in a critical catalytic residue (D145N) was used to assemble Sic1 complexes. In such complexes, Sic1 remains essentially unphosphorylated, however the Sic1 is readily phosphorylated by Cln1/Cdc28 (See, FIG. 2A). In vitro phosphorylation of Sic resulted in a reduction in its electrophoretic mobility (See, FIG. 2B), reminiscent of that observed with Sicd in vivo.

In the absence of Cln1 kinase, the extent of Sic1 phosphorylation was found to be less than 2% of that of phosphorylated Sic1, but this modification did not result in alterations in electrophoretic mobility. For simplicity, this weakly phosphorylated form of Sic1 is herein referred to as "unphosphorylated Sic1."

Cdc4 is the Specificity Factor for Recognition of Phosphorylated Sic1

Figure 2C:
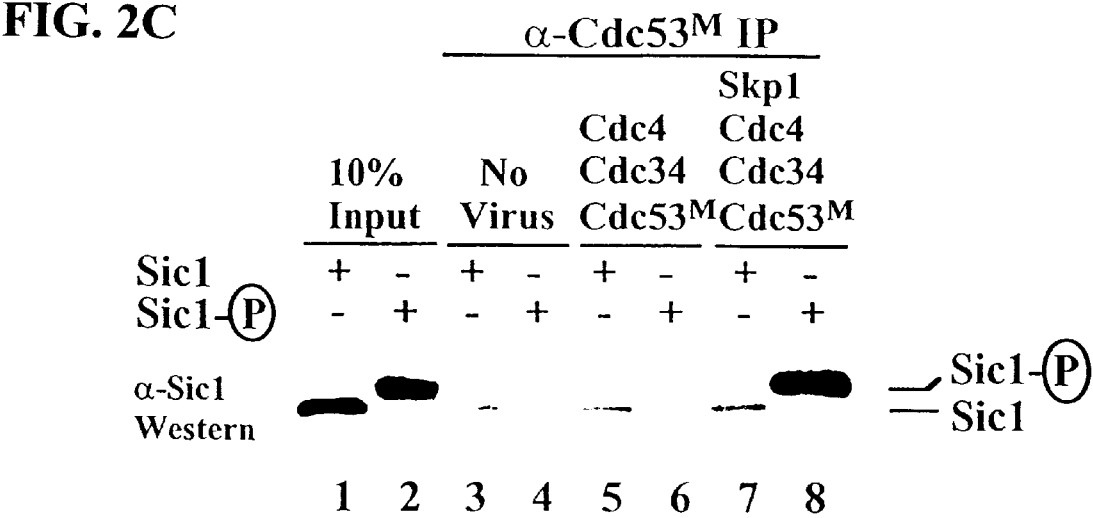
FIG. 2C shows immunoblot results indicating that phosphorylation of Sic1 is required for its association with Cdc34/Cdc53/Skp1/Cdc4 complexes.

Phosphorylated and unphosphorylated Sic1 were used in binding reactions with anti-Cdc53$^M$ immune complexes assembled and purified from insect cells (See, FIG. 2C). Phosphorylated Sic1 was found to efficiently associate with Cdc53/Skp1/Cdc4 complexes; this association was dependent upon the presence of Skp1 (See, FIG. 2C, lanes 6 and 8). Typically 10–20% of the input phosphorylated Sic1 was bound at about 20 nM Sic1. In contrast, the extent of binding of unphosphorylated Sic1 (See, FIG. 2C, lane 7) was comparable to that observed in control immune complexes generated from uninfected cells (See, FIG. 2C, lane 3), and was less than 1% of the input Sic1. It was also observed that, consistent with the results in FIG. 1, the level of Cdc4 found in immune complexes lacking Skp1 were more than 10-fold lower than that found in the presence of Skp1. Thus, Cdc4 and/or Skp1 function as binding factors for Sic1, and association of Sic1 with this complex requires phosphorylation by Cln1/Cdc28.

In addition, to directly examine the roles of Skp1 and Cdc4 in Sic1 recognition, binding experiments were performed using series of complexes assembled in vivo that contained constant high levels of Flag-tagged Skp1 (Skp1$^F$), and increasing quantities of Cdc4. These experiments, as described in the Examples, showed that association of phosphorylated Sic1 with anti-Skp1$^F$ immune complexes was absolutely dependent upon the presence of Cdc4 (e.g., compare lanes 3 and 9 of FIG. 2E). Moreover, deleting the last three WD-40 repeats from the C-terminus of Cdc4 (Cdc4ΔWD) abolished its ability to associate with phosphorylated Sic1 (See, FIG. 2E, lanes 10–16). Therefore, these experiments indicated that Cdc4 functions as the specificity factor for binding of phosphorylated Sic1, and the Cdc4-Sic1 interaction requires an intact WD-40 repeat domain in Cdc4. While Skp1 alone does not interact with Sic1, it stimulates association of Sic1 with with Flag-Cdc4 (Cdc4$^F$) by about 5-fold (See, FIG. 2D). The weak association of Sic1 with Cdc4 alone (See, FIG. 2D, lane 3) may reflect the participation of an insect cell Skp1 homolog. Although it is not clear if Skp1 physically contacts Sic1 or stabilizes a form of Cdc4 compatible with Sic1 binding, and such an understanding is not necessary in order to use the present invention, these results clearly demonstrated that there is a positive contribution of Skp1 tin the Cdc4/Sic1 interaction.

Sic1 is Ubiquitinated In Vivo

Figure 3A:
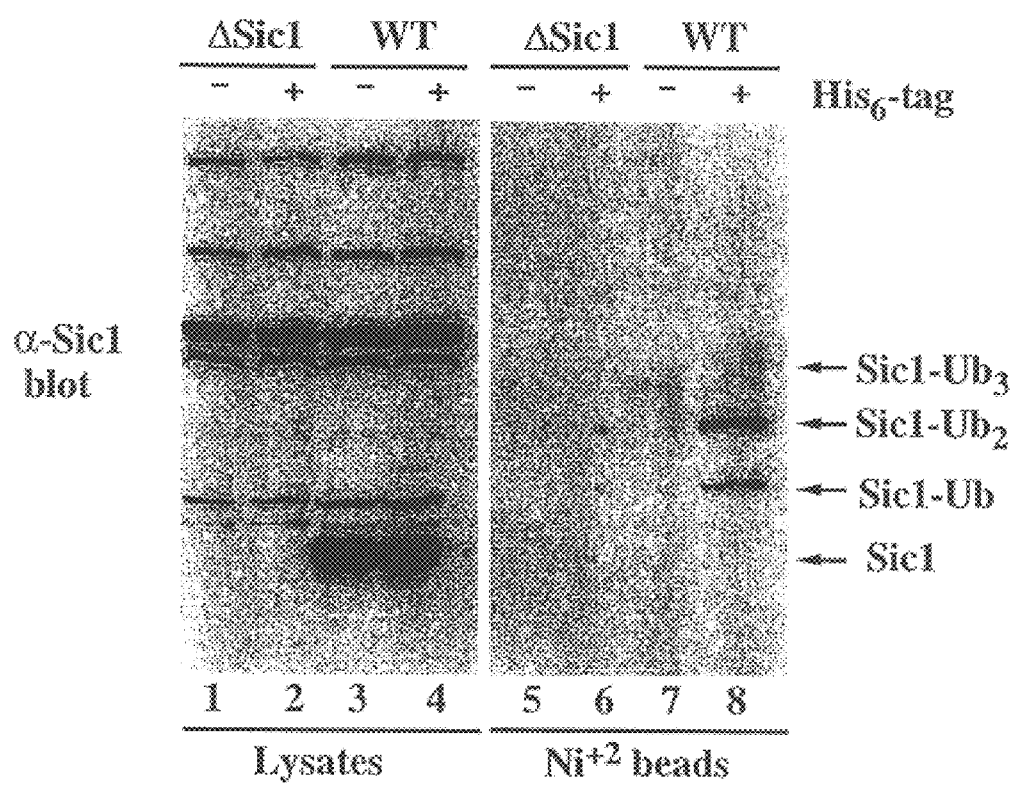
FIG. 3A shows the immunoblot results demonstrating that phosphorylated Sic1 is ubiquitinated in vivo and in vitro with purified Cdc34 E2 and Cdc53/Skp1/Cdc4 complexes.

While the finding that Cdc4, Skp1, and Cdc53 form a complex that binds both phosphorylated Sic1 and the E2 Cdc34 was consistent with a role for ubiquitination in the regulation of Sic1 abundance, prior to the development of the present invention, Sic1 had not been demonstrated to be ubiquitinated in vivo. In order to directly accomplish this, insect cell lysates were generated from either wild type cells or sic1 deletion mutants expressing His$_6$-Ub$^{RA}$ or Ub$^{RA}$ as a negative control, and ubiquitinated proteins purified using Ni$^{+2}$ beads (Willems et al., Cell 86:453–463 [1996]) prior to immunoblotting with anti-Sic1 antibodies (See, FIG. 3A).

The K48R mutation in Ub$^{RA}$ blocks polyubiquitination and therefore recognition by the proteolytic machinery (i.e., proteosome recognition) (Chau et al., Science 243:1576–1583 [1989]), while the G76A mutation reduces the rate at which hydrolases remove ubiquitin conjugates (Hodgins et al., J. Biol. Chem., 267:8807–8812 [1992]). A ladder of bands recognizable by anti-Sic1 antibodies was detected in the Ni$^{+2}$-bead bound proteins from wild type lysates expressing His$_6$-Ub$^{RA}$ (See, FIG. 3A, lane 8) but not in conjugates derived from Ub$^{RA}$-expressing cells or a sic1 deletion strain (See, FIG. 3A, lanes 5 and 6). This result demonstrates that Sic1 is ubiquitinated in vivo. Thus, the present invention also provides an important therapeutic target for development of drugs and other compounds for disease prevention and/or treatment.

Reconstitution of the Sic1 Ubiquitination Pathway Using Purified Proteins

Figure 5B:
FIG. 5B shows an immunoblot verifying the presence of Cdc4, Grr1G10, $Cdc53^M$, and $Skp1^F$.
Figure 5B:
Figure 5B:
Figure 5B:
Figure 5C:
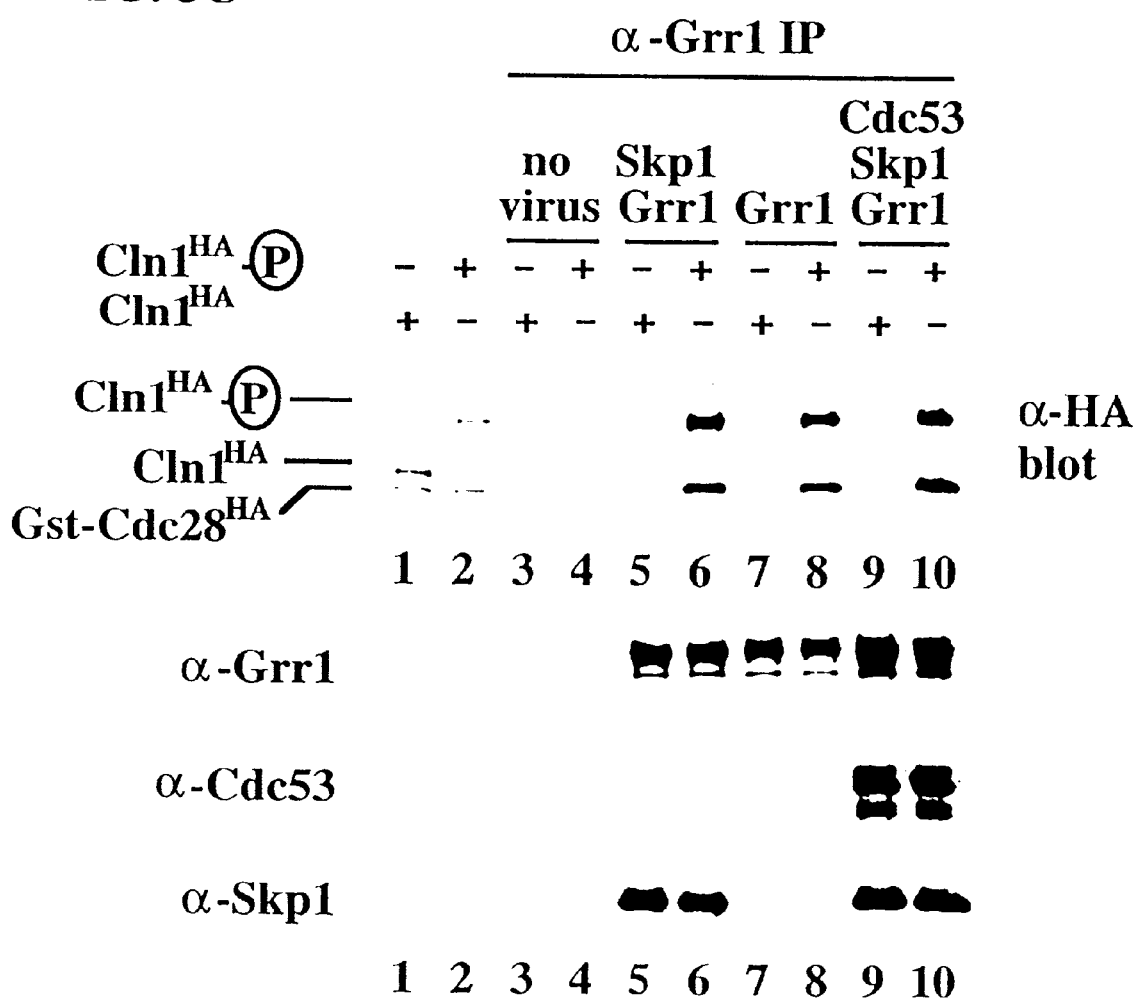
FIG. 5C is an immunoblot indicating that phosphorylation of Cln is required for the association of Cln1/Cdc28 complexes with Grr1.

Once a strategy to generate Cdc4/Skp1/Cdc53 complexes that recognized phosphorylated Sic1 was developed, the next step was to determine whether these complexes can catalyze ubiquitination of Sic1 in vitro when supplemented with Cdc34, E1, ATP, and ubiquitin. It was observed that in the presence of all reaction components, phosphorylated Sic1 in complexes with Clb5/Cdc28 was efficiently convened to higher molecular weight conjugates detectable with anti-Sic1 antibodies (See, FIG. 5B, lane 6; and FIG. 5C, lane 5). In contrast, unphosphorylated Sic1 was not detectably ubiquitinated. Sic1 ubiquitination absolutely required Cdc34, Cdc4, Cdc53, Skp1, E1 and ubiquitin (See e.g, FIG. 5B and FIG. 5C), as well as yeast Skp1. The pattern of high molecular weight Sic1 conjugates obtained in reactions with ubiquitin was different from that observed when Gst-Ub$^{RA}$ was used as the ubiquitin source, (See, FIG. 5C, compare lanes 5 and 11) confirming that the high molecular weight forms observed were products of ubiquitination. With Gst-Ub$^{RA}$, the Sic1 reaction products were integrated into a ladder of bands differing by approximately 35 kDa, the size of Gst-Ub$^{RA}$ (See, FIG. 3C, lane 11). Since Gst-Ub$^{RA}$ had a reduced ability to form polyubiquitin chains, the number of bands observed is likely to reflect the number of individual lysines ubiquitinated on a single Sic1 molecule. The ubiquitination reaction was time-dependent and the reaction efficiency ranged from 10–40% of the input Sic1 protein (See e.g., FIG. 3B and 3C). When the reaction was performed with pre-bound Sic1, the efficiency was greater than 50%. In addition, it was found that greater than 50% of the Sic1 ubiquitin conjugates formed after 60 minutes had dissociated from the Cdc4/Skp1/Cdc53 complex. Neither Gst-Cdc28, Clb5, Cdc53, Skp1, or Cdc4 formed ubiquitin conjugates under the reaction conditions employed, although Cdc34 was ubiquitinated as previously reported.

Figure 3B:
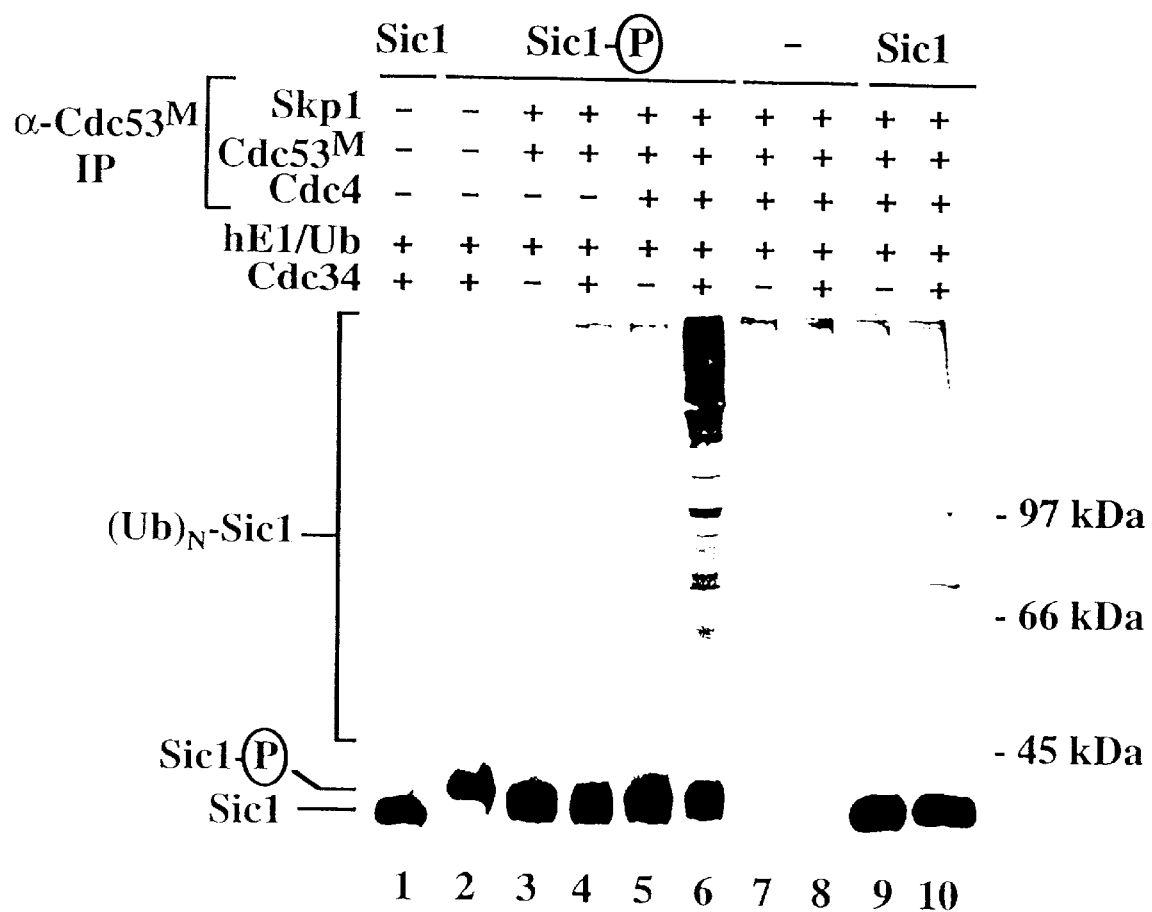
FIG. 3B shows immunoblot results for anti-$Cdc53^M$ immune complexes tested against $Cdc53^M$/Skp1, $Cdc53^M$/Skp1/Cdc4, and supplemented with ATP, ubiquitin, human E1, Cdc34 purified from *E. coli*, and either unphosphorylated or phosphorylated Sic1 complexes.
Figure 3C:
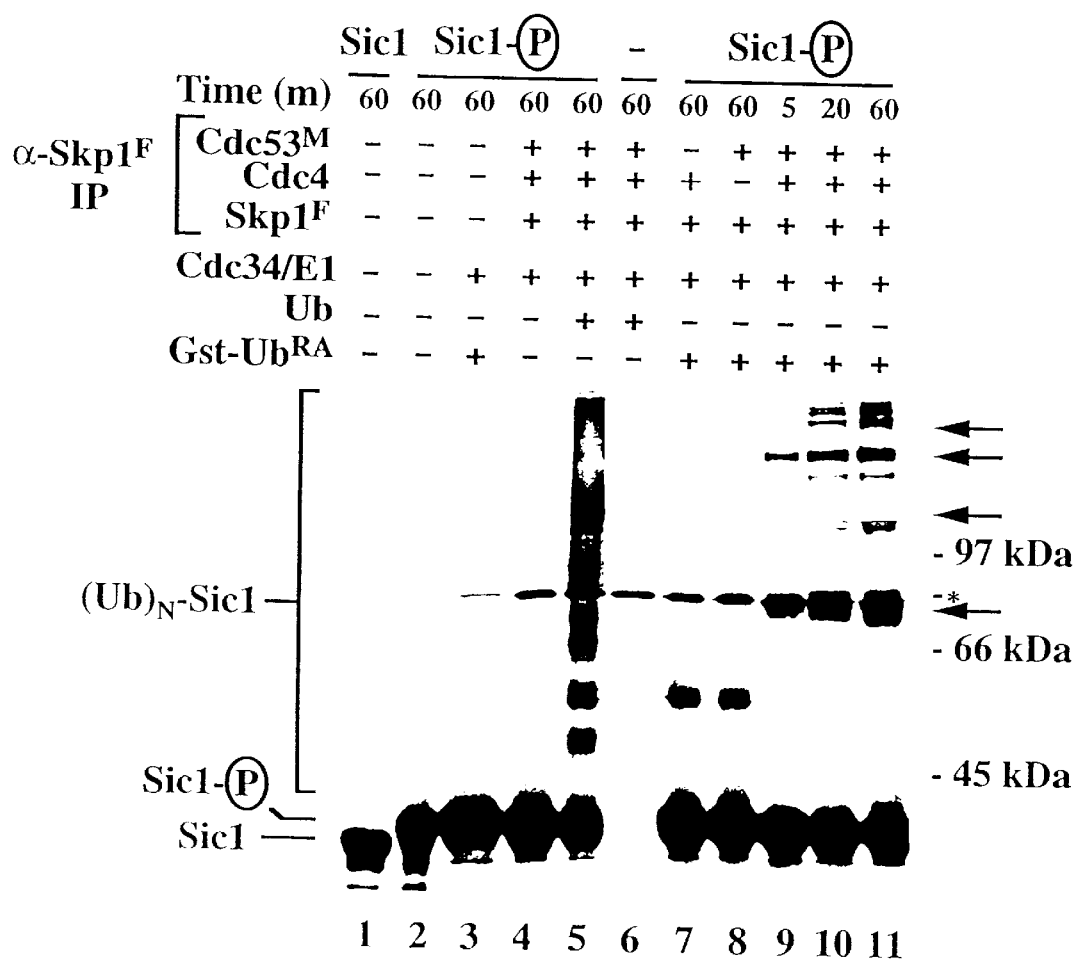
FIG. 3C shows immunoblot results for anti-$Skp1^F$ immune complexes tested with $Skp1^F$/$Cdc53^M$/Cdc4, $Skp1^F$/Cdc4, and $Skp1^F$/$Cdc53^M$.
Figure 3D:
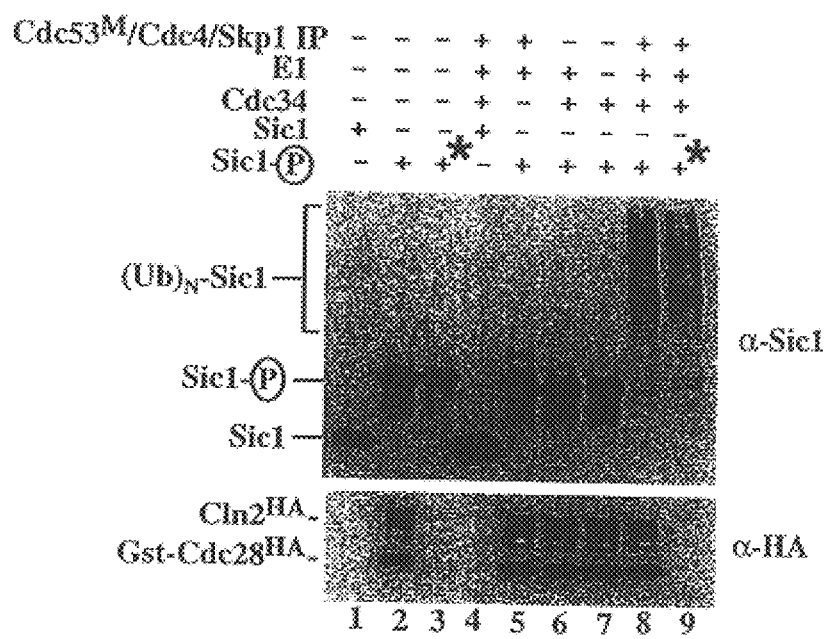
FIG. 3D shows immunoblot results that indicate ubiquitination of Sic1 does not require that Cln/Cdc28 be present in the ubiquitination reaction nor that Sic1 be associated with Clb5/Cdc28.

To test whether Sic1 ubiquitination requires association with Clb5/Cdc28 complexes, ubiquitination reactions using Sic1 produced in bacteria were performed both with and without phosphorylation with Cln2/Cdc28 (See, FIG. 3D). As in the case of Sic1 assembled in insect cells with Clb5/Cdc28, phosphorylated Sic1 from bacteria was efficiently ubiquitinated with greater than 90% of the Sic1 forming ubiquitin conjugates (See, FIG. 3D, lane 8), and ubiquitination absolutely required Sic1 phosphorylation (i.e., unphosphorylated Sic1 was not ubiquitinated; See e.g., FIG. 3D, lane 4). Thus, phosphorylation of Sic1 was shown to be required for its recognition by Cdc4 and Skp1.

Next, it was determined whether Cln/Cdc28, present in small amounts in the ubiquitination reaction, is also required for additional steps in the ubiquitination process (e.g, to phosphorylate the ubiquitination machinery). This was accomplished by treating bacterial Sic1 with Cln2/Gst-Cdc28 complexes immobilized on GSH-Sepharose beads, removing the complexes from the beads prior to use in ubiquitination reactions, and determining whether the complexes were free of soluble kinase by immunoblotting with anti-HA antibodies (See, FIG. 3D, lane 3). These results indicated that Sic1 phosphorylated in this manner was also efficiently ubiquitinated (See, FIG. 3D, lane 9). Thus, these data indicated that Sic1 phosphorylation constitutes the primary requirement of Cln/Cdc28 kinases in Sic1 ubiquitination in the in vitro reaction.

Figure 3E:
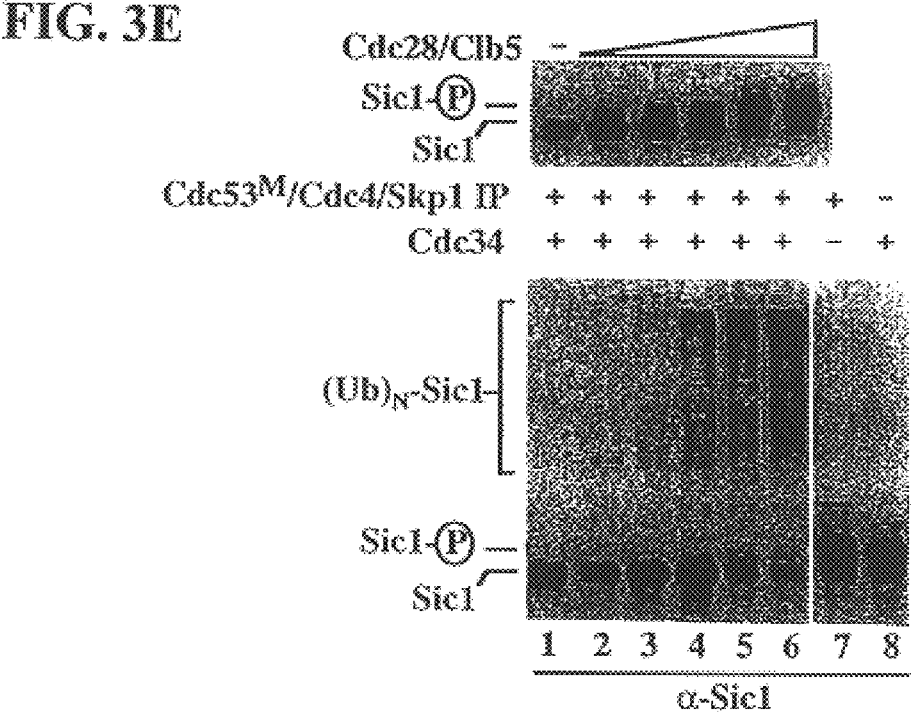
FIG. 3E shows immunoblot results that Clb5/Cdc28-phosphorylated Sic1 is a substrate for ubiquitination by Cdc34.

Although Sic1 was found to be an inhibitor of Cdc28/Clb5 complexes, when the kinase complex contained an excess of Sic1, it was incapable of phosphorylating Sic1 and converting it into a substrate for ubiquitination (FIG. 3E shows the reduced electrophoretic mobility) and $^{32}$P incorporation. This Clb5/Cdc28-phosphorylated Sic1 was also a substrate for ubiquitination (See, FIG. 3E). Although it is not necessary to understand the mechanisms involved in order to use the present invention, overexpression of CLB5 can drive S-phase entry in cln- cells and suggests that active Clb5/Cdc28 formed during Sic1 destruction may collaborate with Cln/Cdc28 to complete the Sic1 ubiquitination process.

F-box Proteins are Receptors for Ubiquitination Substrates

The determination that Cdc4 functions in the recognition and ubiquitination of phosphorylated Sic1 is consistent with a function of F-box proteins being recognition of ubiquitination targets. During the development of the present invention, investigations into whether specific F-box proteins could have broad specificity and interact with multiple targets, or could be relatively restricted in their target specificity, perhaps associating with only a single target, were conducted.

To elucidate the selectivity of F-box proteins, experiments were conducted to determine whether substitution of Cdc4 by another F-box protein (Grr1) could support Sic1 binding and ubiquitination. Grr1 has an F-box near its N-terminus and can interact simultaneously with Skp1 and Cdc53 when co-expressed in insect cells. Gene 10-tagged Grr1 (Grr1$^{10}$) was also found to interact simultaneously with Skp1 and Cdc53, when co-expressed in insect cells (See, FIG. 4A). It was found that Grr1 and Cdc4 interact with Skp1/Cdc53 in a mutually exclusive manner. In contrast with Cdc4, however, the Grr1/Cdc53 interaction in insect cells was not enhanced by co-expression of Skp1, although Skp1 assembled with these complexes.

Figure 4A:
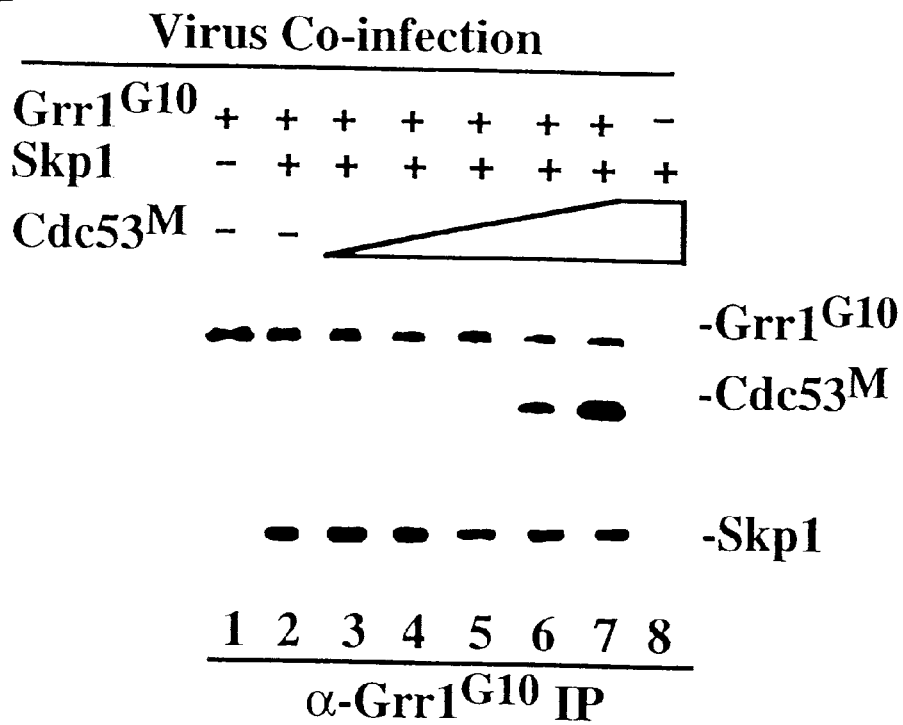
FIG. 4A shows immunoblot results indicating that Grr1 can associate with Skp1 and Cdc53.
Figure 4B:
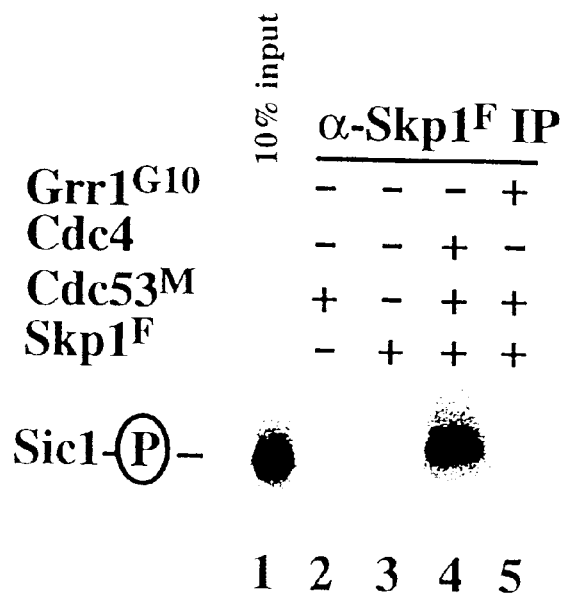
FIG. 4B shows an autoradiograph indicating that phosphorylated Sic1 associates with Cdc4 but not Grr1-containing complexes.

Importantly, Grr1 assembled with Cdc53/Skp1 (i.e., Cdc53/Skp1/Grr1 complex) was unable to associate with phosphorylated Sic1 and did not support ubiquitination of phosphorylated Sic1 complexes in the in vitro system with purified proteins under conditions where Cdc4 readily facilitates Sic1 binding and ubiquitination (See, FIGS. 4B and C). Therefore, the F-box proteins of some embodiments of the present invention display selectivity toward particular targets.

Recognition of Phosphorylated Cln1 and Cln2 by Grr1

Previous studies have shown that mutations of potential Cdc28 phosphorylation sites in the C-terminal PEST domain in Cln2 increase its stability in vivo (Lanker et al., Science 273:1597–1601 [1996]), and that only the phosphorylated form of Cln2 is associated with Cdc53 in vivo (Willems et al., [1996], supra), implicating this interaction in the Cln destruction pathway. Cdc28 is required for Cln phosphorylation although it has not been determined that the requisite phosphorylation reflects autophosphorylation or phosphorylation by a distinct protein kinase. The finding that Sic1 is recognized by the F-box protein Cdc4, together with a genetic requirement for the F-box protein Grr1 in Cln destruction, led to the next step in the development of the present invention, namely the examination of whether Grr1 functions in recognition of phosphorylated Clns.

To generate Cln proteins for binding reactions, Cln/(Gst-Cdc28 complexes were isolated from insect cells. In the presence of ATP, both Cln1 and Cln2 were found to be autophosphorylated, a modification that reduces their electrophoretic mobility (see below). To examine whether Grr1 can associate with phosphorylated Clns and to compare the extent of selectivity of Grr1 and Cdc4 toward Cln binding, anti-Skp1$^F$ immune complexes from cells co-expressing Grr1 or Cdc4 in the presence or absence of Cdc53 were used in binding reactions with $^{32}$P-labeled Cln1 or Cln2 kinase complexes. $^{32}$P-labeled Sic1 was used as a control for Cdc4 binding. Both Cln1 and Cln2 complexes were found to associate with Grr1/Skp1$^F$/Cdc53 complexes (See, FIG. 5A) with an efficiency of about 40% of the input Cln1 or Cln2 (See, FIG. 5A, lanes 8 and 12) and this association did not require Cdc53 (lane 16). In contrast, about 6% of the input Cln proteins associated with Cdc4/Skp1$^F$ complexes independent of the presence of Cdc53 (lanes 7, 11, and 15), compared with 1% association in the absence of an F-box protein (lanes 6, 10, 14). The extent of selectivity of these F-box proteins for Cln and Sic1 was further reflected by the observation that Cln1 protein present in the phosphorylated Sic1 preparation was selectively enriched in Grr1 complexes (FIG. 5A, lane 4). The presence of all proteins in the binding reaction was confirmed by immunoblotting (FIG. 5B) and the quantities of Cdc4 and Grr1 were comparable, based on Coomassie staining of SDS gels of immune complexes. Thus, Grr1 and Cdc4 display specificity toward physiological substrates.

Cln1 Phosphorylation is Required for Recognition by Grr1

If Cln phosphorylation is required for ubiquitination as suggested by genetic studies (Lanker et al., [1996], supra; and Willem et al., [1996], supra), and if Grr1 is the receptor for Clns, then the Grr1/Cln interaction would be expected to be phosphorylation dependent. Thus, the next step in the development of the present invention was to examine Grr1 alone and in complexes with Skp1 or Skp1/Cdc53. Thus, Grr1 alone, or in complexes with Skp1 or Skp1/Cdc53 was immunoprecipitated from insect cell lysates and used in binding assays with phosphorylated or unphosphorylated Cln1 complexes (FIG. 5C).

Figure 5D:
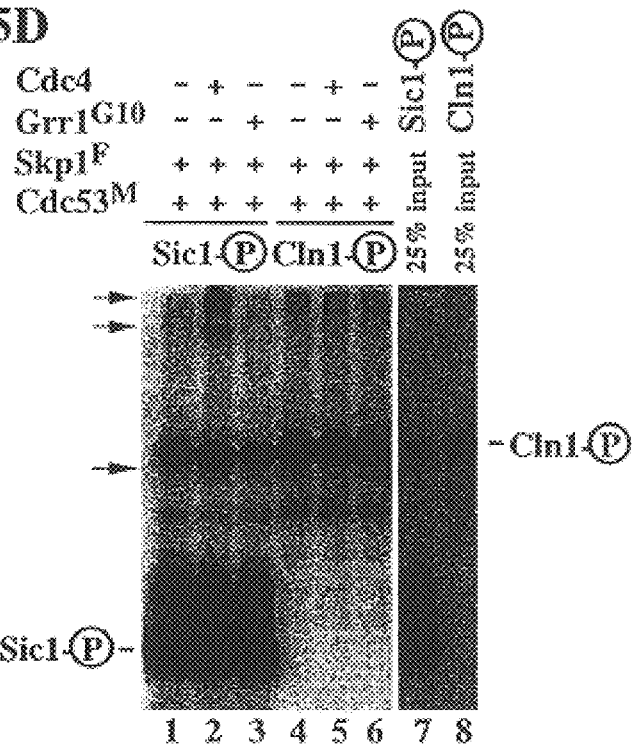
FIG. 5D is an autoradiograph showing that purified Skp1/Cdc53/Grr1 complexes are not sufficient for Cln1 ubiquitination by Cdc34 in vitro.

Unphosphorylated Cln1 was produced in insect cells as a complex with kinase deficient Gst-Cdc28(K–), which minimized Cln1 autophosphorylation during expression and allowed the role of phosphorylation to be tested. As isolated, this Cln1 protein migrated as a homogeneous species of approximately 66 kDa (FIG. 5C, lane 1). In contrast, phosphorylated Cln1 (lane 2) undergoes a dramatic mobility shift to approximately 80 kDa, consistent with the results observed in vivo. Phosphorylated Cln1 (and its associated Cdc28 protein) efficiently associated with all Grr1 complexes (FIG. 5C, lanes 6, 8, 10), but was absent from control binding reactions lacking Grr1 (FIG. 5C, lane 4). In contrast, the levels of unphosphorylated Cln1 associated with Grr1 complexes were compared to that found in binding reactions lacking Grr1 (FIG. 5C, lanes 3, 5, 7, 9). Thus, association of both Cln1 with Grr1 and Sic1 with Cdc4 is greatly enhanced by phosphorylation. Although the Grr1/Skp1/Cdc53 complex is capable of binding efficiently to phosphorylated Cln1, it was not competent for Cln1 ubiquitination when supplemented with Cdc34 and E1 (FIG. 5D). Moreover, Cdc4 complexes that functioned in Sic1 ubiquitination also failed to catalyze ubiquitination of Cln1 (FIG. 5D), despite the fact that Cln1 can associate, albeit weakly, with Cdc4 (FIG. 5A). In contrast, identical preparations of phosphorylated Cln1 protein were efficiently ubiquitinated in partially purified yeast lysates in a Cdc34-dependent manner (See e.g, FIG. 5E), indicating that this preparation of Cln1 is competent for ubiquitination. Although an understanding of the mechanism is not necessary in order to use the present invention, the absence of Cln1 ubiquitination in the purified system is may reflect the requirement of additional factors or modifications.

F-box Proteins as Receptors for Ubiquitination Targets

The present invention contemplates that a large number of proteins contain the F-box, and are thereby implicated in the ubiquitin pathway. The development of the present invention has revealed that F-box proteins directly contact ubiquitination substrates and can display selectivity in recognition of potential targets for ubiquitination, as would be expected of E3 proteins. For example, both Grr1 and Cdc4 assemble into mutually exclusive complexes with Cdc53 and Skp1 (FIG. 4). However, Grr1 does not associate with Sic1, nor does it support Sic1 ubiquitination. In contrast, it was found that Cln proteins efficiently associate with Grr1/Skp1$^F$ complexes and with Cdc4/Skp1$^F$ (although less efficiently) (See e.g., FIG. 5). Although Cdc53 was originally isolated as a Cln2-interacting protein (Willems et al., [1996], supra), the present invention provides evidence that this original interaction was bridged by Grr1 and possibly Cdc4. The Grr1/Cln interaction is of interest in view of the fact that GRR1, CDC53, and SKP1 are required for destruction of Cln proteins, and suggests that Grr1 functions as a component of an E3 for Cln ubiquitination. The absence of Cln ubiquitination by purified Grr1 complexes is likely to indicate the absence of an essential factor(s) or modifications that are not required for Sic1 ubiquitination in vitro, and provides evidence that Cln ubiquitination may be more complex than is Sic1 ubiquitination. Nonetheless, the present invention provides methods, compositions, and models for the development of compounds that interact with the ubiquitination process, and thereby affect protein degradation through any number of routes.

Despite the observation that F-box proteins may show selectivity towards potential substrates, it is unlikely that F-box proteins will be monospecific. For example, in *S. pombe*, recent genetic data have linked the CDC4 homolog pop+ with the ubiquitination of both the CK1 Rum1 and Cdc18, a regulator of DNA replication (Kominami and Toda, Genes Dev., 11:1548–1560 [1997]). In budding yeast, CDC4 has also been implicated in destruction of the Cdc18 homolog Cdc6 (Piatti et al., Genes Dev., 10:1516–1531 [1996]), indicating that it too has multiple targets. It was also determined that Cdc4 can associate with Clns, albeit less efficiently than with Grr1 (FIG. 5). Of importance is the fact that all of the targets of F-box protein mediated destruction identified to date are central regulators of key events in the cell, including DNA replication, cell cycle progression, and nutritional sensing.

A Cdc53/Cdc4/Skp1 E3 Complex is Required for Sic1 Ubiquitination by Cdc34

Sic1 destruction is genetically dependent upon Cdc34, Cdc4, Cdc53, and Skp1. During the development of the present invention, it was determined that these proteins are directly involved in the ubiquitination process. As Cdc5 3 can simultaneously bind the E2 Cdc34 and Skp1, it frictions as an adapter linking the Skp1/F-box protein complex to E2s (FIG. 1). In turn, Skp1 has the ability to link Cdc4 to Cdc53. Cdc4 binds both Skp1 and the ubiquitination substrate Sic1. The interaction of Cdc4 with Skp1 was shown to involve the F-box located in the N-terminus of Cdc4, while the interaction with Sic1 involves Cdc4's C-terminal WD-40 repeats (FIG. 2). Skp1 was also shown to be involved in substrate recognition because it enhances the association of Cdc4 with phosphorylated Sic1. Cdc4 was shown to act as a receptor that, in conjunction with Skp1, recruits substrates to the ubiquitination complex. It is contemplated that any of these proteins could also have carrier roles in the transfer of ubiquitin like E6AP (See e.g., Scheffner et al., Cell 75:495–505 [1995]). However, it was determined that mutation of the only conserved cysteine in Skp1 or all 6 cysteines in Cdc53 did not impair complementation of skp1 or cdc53 null mutations, respectively, indicating that these two proteins are unlikely to transfer ubiquitin by a thio-ester intermediate.

Phosphorylation Directly Regulates Association of Sic1 and Cln Proteins with E3s A central feature in the recognition of Sic1 and Cln by F-box proteins is the phosphorylation dependent nature of the interaction. Association of Sic1 with Cdc4-containing complexes and subsequent ubiquitination requires Sic1 phosphorylation, as shown in FIGS. 2 and 3. It was also shown that Sic1 phosphorylated by excess Clb5/Cdc28 kinase can be ubiquitinated in vitro (See, FIG. 3E). It is contemplated that the initial generation of Clb5/Cdc28 activity at the G1/S transition could potentially accelerate Sic1 destruction facilitating the sharp and unidirectional change of state characteristic of cell cycle transitions.

Similarly, association of Grr1 with Cln proteins is greatly enhanced by phosphorylation, as indicated in FIG. 5. Phosphorylation of specific residues in the C-terminal PEST domain of Cln1 is required for Cln2 instability (Lanker et al., [1996], supra), and phosphorylated Cln2 is found in complexes with Cdc53 in vivo (Willems et al. [1996], supra). The present invention shows that Cln/Cdc28 can provide that function in vitro. The present invention also provides methods, compositions, and models for the determination of whether Cln ubiquitination is activated by autophosphorylation in trans, as the accumulation of active Cln/Cdc28 complexes may be required to achieve sufficient Cln phosphorylation to promote its destruction.

While regulating the association of F-box proteins through substrate phosphorylation is an effective method controlling the timing of ubiquitination, it is not necessarily the case that all F-box proteins will recognize their substrates in a proteolysis substrates in these and other organisms, as well as providing the flexibility to differentially regulate the ubiquitination of a very large number of substrates.

Other Applications

In addition, various embodiments of the present invention find use in other settings. For example, the methods, compositions, and models of the present invention provide the tools to determine the function of such proteins as elongin C, a Skp1-related protein is part of a complex containing the Cdc53-related protein Cul2, the von Hippel-Lindau (VHL) tumor suppressor protein, elongin B, and elongin A, a protein that is also found in association with elongin C, and contains an F-box. Thus, the present invention provides the means to develop compounds that affect systems other than ubiquitination-mediated proteolysis.

Indeed, the F-box-directed ES complex (FEC) embodiment described in detail herein, represents one example of a pathway through which protein kinases control the stability of target proteins. In view of the large number of protein kinases and possible FECs, this pathway may be second only to transcriptional regulation in the control of protein abundance. While the specific examples described herein focus on the concern the cell cycle, the present invention provides methods, compositions and models applicable to other, diverse regulatory systems.

Figure 6A:
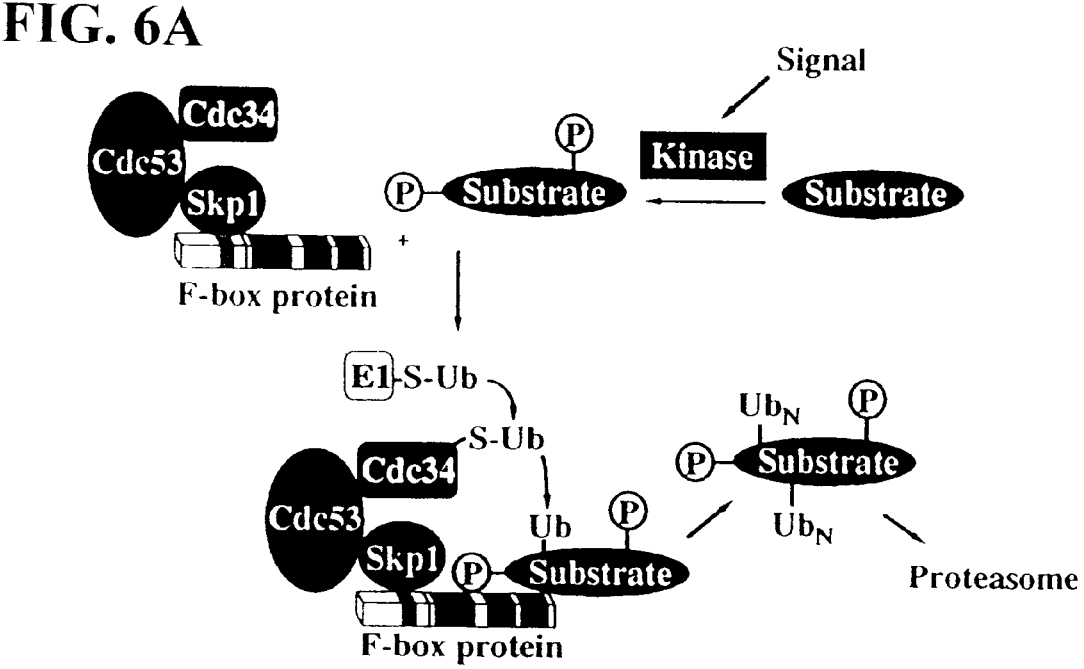
FIG. 6A is a schematic showing that phosphorylation of substrates through protein kinase signalling pathways is required for recognition by F-box receptor proteins.

Although an understanding of the mechanism it is not necessary in order to use the present invention, FIG. 6A provides a model in which a protein kinase phosphorylates target proteins, thus activating them for association with their receptors, the F-box proteins. Although some F-box proteins may already be associated with a Skp1/Cdc53 complex prior to association with substrates, as shown in FIG. 6A, it is also possible that F-box proteins exist in a unbound form, and that association of the F-box protein with the substrate drives association with Skp1/Cdc53. Since Skp1 enhances the association of Cdc4 with Sic1, depending on the relative Kd values for individual interactions and concentrations of the constituents, association of the target with an F-box protein may enhance association with Skp1. Once the ubiquitination complex is formed and polyubiquitination takes place with the assistance of E1 and E2 phosphorylation dependent manner. Observations made during the development of the present invention indicate that WD-40 and LRR containing F-box proteins can interact with phosphorylated substrates, but approximately half of the known F-box proteins do not have obvious protein interaction motifs. Nonetheless, the present invention provides methods, compositions, and models to determine whether the interaction of these proteins with their targets is regulated by phosphorylation or even involves ubiquitination.

The timing of ubiquitination could be controlled by mechanisms unrelated to substrate phosphorylation, such as controlled accessibility of substrates or regulated expression, localization, or modification of the F-box protein, thus providing methods for development of compounds that affect proteolysis.

While the abundance of Cdc4 is not cell cycle regulated, the F-box protein Skp2 displays cell cycle-regulated mRNA abundance which peaks in S-phase, consistent with its association with cyclin A during that phase of the cycle (Zhang et al., [1995], supra). In vivo, association of Grr1 and Skp1 is enhanced in the presence of glucose in a post-translational mechanism.

A large number of proteins contain PEST sequences and in a subset of these proteins, these sequences have been shown to be phosphorylated and to mediate instability. The development of one embodiment of the present invention focused on the role of Skp1 and F-box proteins in assembly of a ubiquitination complexes that recognizes specific phosphorylated proteins. While the particular complex defined by this embodiment of the present invention is unlikely to be responsible for recognition of all PEST-dependent proteolysis substrates, this complex is likely to be the prototype for a diverse set of complexes in higher eukaryotes. Five CDC53 homologs have been identified in mammals (Cul1–5; Kipreos et al., Cell 85:829–839 [1996]), approximately 15 E2-relates genes exist in *S. cerevisiae* alone, several dozen F-box containing proteins have been identified in several species, and several SKP1 related genes exist in *C. elegans* and are likely to exist in mammals as well. It is clear that the present invention provides methods, compositions, and models to identify PEST-dependent proteins, the substrate is then released and recognized to the 26S proteosome where it is proteolyzed.

Figure 6B:
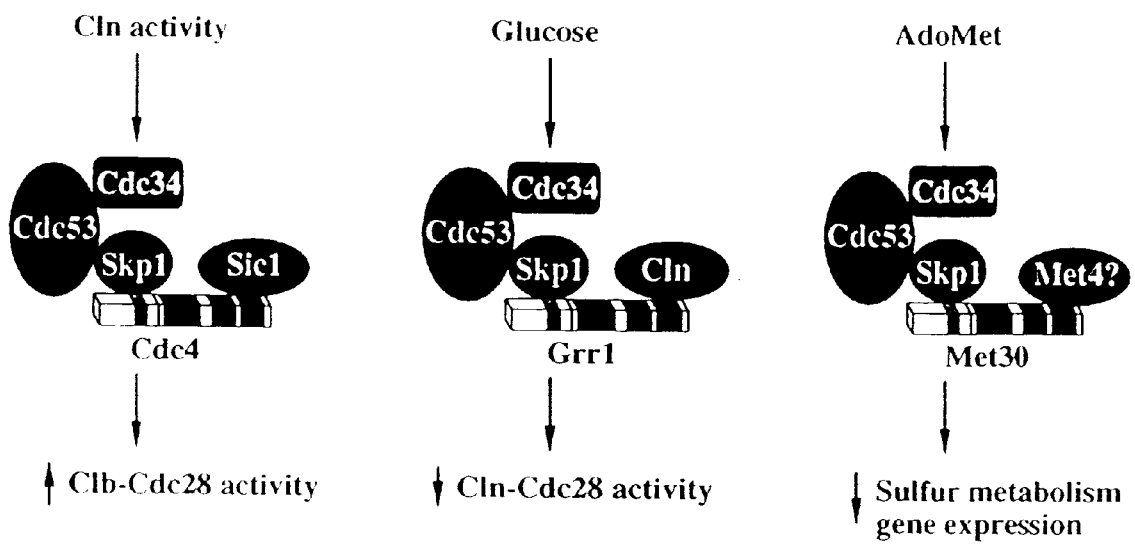
FIG. 6B is a schematic showing that distinct F-box complexes may regulate different biological processes through selective recruitment of substrates. Hypothetical FEC configurations are shown together with the signals that are being sensed, the corresponding substrates and the physiological consequences of complex function.

As indicated in FIG. 6B, it is contemplated that other combinations of FEC (or "SCF") complexes exist in cells. For example, the F-box protein Met30 is closely related to Cdc4, and is required for repression of genes in the methionine biosynthetic pathway in the presence of S-adenosylmethionine (AdoMet) (See, Thomas et al., Mol Cell. Biol., 15:6526–6534 [1995]). Met30 forms a complex with Met4, a transcription factor required for methionine biosynthetic gene expression. The present invention provides the means to determine whether Met4 is ubiquitinated in response to adomethionine. Furthermore, although the primary embodiment of the present invention has focused on Cdc34, the present invention provides means to determine whether other E2s are capable of functioning in the context of FECs.

Figure 6C:
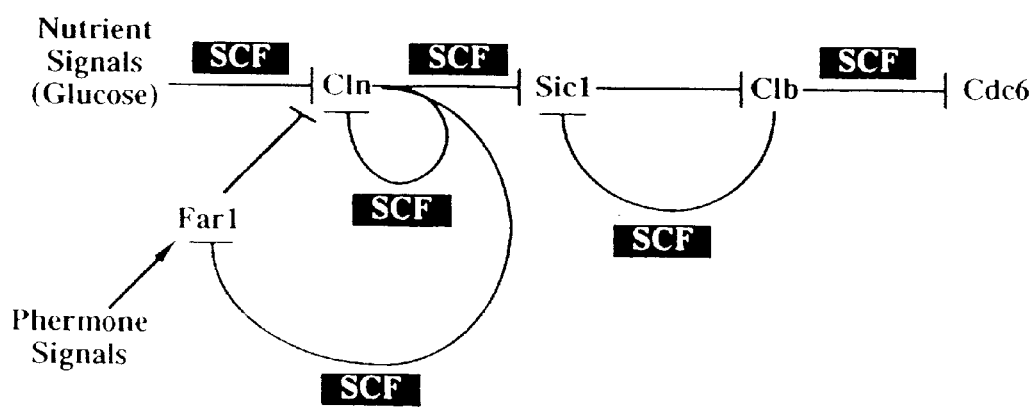
FIG. 6C is a schematic showing the interplay between protein kinase and the SCF pathway in the G1 to S-phase transition in *S. cerevisiae*. In this Figure, perpendicular bars indicate inhibitory events.

Also, as shown in FIG. 6C, SCF complexes (i.e., Skp1, Cdc53, and Cdc4 present in a multiprotein complex), work together with protein kinase signalling pathways to control protein abundance. FIG. 6C illustrates one such pathway, in which SCF pathways function multiple times in the transition from G1 to S phase in *S. cerevisiae*.

Like protein synthesis, protein destruction is a fundamental mechanism used by organisms to manipulate their function. In one embodiment, the present invention provides the composition of an E3 complex, FEC, involved in selection of ubiquitination substrates. Because the constituents of this complex are members of protein families, the present invention provides the prototype for a large class of E3s formed by combinatorial interactions of related family members as indicated in FIG. 6B. The identification of F-box proteins as the receptor components of this ubiquitin ligase provides the means for identification of the key regulatory molecules controlled by ubiquitin-mediated proteolysis. Thus, the present invention provides means for the elucidation of the biochemistry of this general ubiquitination pathway is likely to have important ramifications for many aspects of biology including cell proliferation, development, and differentiation.

EXPERIMENTAL

The following examples are provided in order to demonstrate and further illustrate certain preferred embodiments and aspects of the present invention, and are not to be construed as limiting the scope thereof.

In the experimental disclosure which follows, the following abbreviations apply: h (human); Sc (*Saccharomyces cerevisiae*); m (mouse); Ub (ubiquitin); E1 (Ub activating enzyme); E2 (Ub carrier protein); E3 (Ub-protein ligase); ° C. (degrees Centigrade); rpm (revolutions per minute); BSA (bovine serum albumin); CFA (complete Freund's adjuvant); IFA (incomplete Freund's adjuvant); IgG (immunoglobulin G); IM (intramuscular); IP (intraperitoneal); IV (intravenous or intravascular); Sc (subcutaneous); $H_2O$ (water); HCl (hydrochloric acid); aa (amino acid); bp (base pair); kb (kilobase pair); kd (kilodaltons); gm (grams); $\mu$g (micrograms); mg (milligrams); ng (nanograms); $\mu$l (microliters); ml (milliliters); mm (millimeters); nm (nanometers); $\mu$m (micrometers); M (molar); mM (millimolar); MW (molecular weight); sec(s) (second/seconds); min(s) (minute/minutes); hr(s) (hour/hours); $MgCl_2$ (magnesium chloride); NaCl (sodium chloride); DTT (dithiothreitol); $OD_{280}$ (optical density at 280 nm); $OD_{600}$ (optical density at 600 nm); PAGE (polyacrylamide gel electrophoresis); PBS (phosphate buffered saline [150 mM NaCl, 10 mM sodium phosphate buffer, pH 7.2]); PEG (polyethylene glycol); PMSF (phenylmethylsulfonyl fluoride); SDS (sodium dodecyl sulfate); SDS-PAGE (sodium dodecyl sulfate polyacrylamide gel electrophoresis); LMA (low melting temperature agarose gel; Tris (tris(hydroxymethyl)aminomethane); NETN (20 mM Tris-HCl, pH 8, 100 mM NaCl, 1 mM EDTA, 0.5% NP-40, 5 mM NaF, 30 mM p-nitrophenylphosphate, 1 $\mu$g/ml each leupeptin and antipain, and 1 mM PMSF); TBST (20 mM Tris (pH 8), 100 mM NaCl, 0.5% Tween-20); IPTG (isopropyl-$\beta$-D-thiogalactopyranoside); LB (Luria-Bertani medium; per liter: 10 g tryptone, 5 g yeast extract, 10 g NaCl, pH 7; sterilized by autoclaving for 20 minutes at 15 lbs/in$^2$); vol (volume); w/v (weight to volume); V/V (volume to volume); Amersham (Amersham Life Science, Inc., Arlington Heights, Ill.); ICN (ICN Pharmaceuticals, Inc., Costa Mesa, Calif.); Amicon (Amicon, Inc., Beverly, Mass.); ATCC (American Type Culture Collection, Rockville, Md.); Becton Dickinson (Becton Dickinson Labware, Lincoln Park, N.J.); BioRad (BioRad, Richmond, Calif.); Clontech (CLONTECH Laboratories, Palo Alto, Calif.); Difco (Difco Laboratories, Detroit, Mich.); GIBCO BRL or Gibco BRL (Life Technologies, Inc., Gaithersburg, Md.); Babco (Berkeley Antibody Company, Richmond, Calif.); Invitrogen (Invitrogen Corp., San Diego, Calif.); Kodak (Eastman Kodak Co., New Haven, Conn.); New England Biolabs (New England Biolabs, Inc., Beverly, Mass.); Novagen (Novagen, Inc., Madison, Wis.); Qiagen (Chatsworth, Calif.); Pharmacia (Pharmacia, Inc., Piscataway, N.J.); Sigma (Sigma Chemical Co., St. Louis, Mo.); Sorvall (Sorvall Instruments, a subsidiary of DuPont Co., Biotechnology Systems, Wilmington, Del.); Stratagene (Stratagene Cloning Systems, La Jolla, Calif.); Whatman (Whatman LabSales, Hillsboro, Oreg.); Bethyl Laboratories (Bethyl Laboratories, Montgomery, Tex.); and Zeiss (Carl Zeiss, Inc., Thornwood, N.Y.).

Unless otherwise indicated, all restriction enzymes were obtained from New England BioLabs and were used according to the manufacturer's instructions; all oligonucleotide primers, adapter and linkers were synthesized using standard methodologies on an ABI DNA synthesizer. All chemicals were obtained from Sigma unless otherwise indicated.

EXAMPLE 1

Preparation of Antibodies

In this Example, anti-Skp1 and anti-Sic1 antibodies were prepared. Using standard methods as known in the art, anti-Skp1 and anti-Sic1 polyclonal antibodies were generated in rabbits, with bacterial Gst fusion protein described below, used as the antigen.

A. Antigen Preparation

Expression plasmids for GST-SKP1 and GST-SIC1 were generated by ligating open reading frames for the encoded proteins into pGEX2TK (Pharmacia), using established procedures known in the art (See e.g., J. Sambrook et aL, supra). The Genbank accession numbers for SKP1 and SIC1 are U61764 and X78309, respectively.

Plasmids, were transformed into F coli strain BL21 (DE3) (Novagen). For expression, 1 L of E. coli cells were grown in LB medium containing 0.1 mg/ml ampicillin at 37° C., until the $OD_{600}$ reached 0.8. Expression was induced with 400 mM IPTG for three hours. Cells were harvested by centrifugation (2,000×g for 10 minutes), and then lysed in 70 ml NETN buffer for 30 minutes, on ice. The insoluble material was then removed by centrifugation (14,000×g, for 20 minutes). The lysate was then incubated with 0.5 ml glutathione Sepharose (Pharmacia) for 1 hour at 4° C. The Sepharose beads were washed three times with 10 ml NETN buffer, and washed twice with 5 ml of 100 mM NaCl, and the protein was eluted with buffer containing 0.5 ml 100 mM Tris (pH 7.5), 100 mM NaCl, 40 mM glutathione. The protein was then stored at −8° C., prior to its use in the affinity purification of antibodies.

B. Antibody Production and Affinity Purification

Polyclonal rabbit anti-Cdc34 and anti-Cdc4 sera (provided by M. Goebl), as well as anti-Sic1, were affinity purified using recombinant antigens immobilized on nitrocellulose. The anti-Skp1 antibodies were not affinity purified.

To affinity purity the anti-Sic1 antibodies, GST-Sic1 protein (0.1 mg) was subjected to electrophoresis on a 12% polyacrylamide (SDS-PAGE) gel, the protein was blotted to nitrocellulose (3 hours, at 350 mA). Nitrocellulose filters containing GST-Sic1 protein were incubated with 1 ml of anti-Sic1 antibodies for 3 hours, the filters were washed twice with 10 ml of buffer containing 50 mM Tris (pH 7.5), 50 mM NaCl, 0.5% Tween-20, and then eluted with 1 ml of 100 mM glycine (pH 2), and stored at 4° C. until use.

In addition to the anti-Skp1 and anti-Sic1 polyclonal rabbit antibodies generated in this Example, and the anti-Cdc34 and anti-Cdc4 polyclonal rabbit antibodies from Dr. Goebl, monoclonal antibodies were also used in the following Examples. These commercially available monoclonal antibodies were obtained from Babco (anti-HA,anti-Myc), Novagen (anti-T7 gene10, [i.e., "G10"]), and Kodak (anti-Flag, M2).

EXAMPLE 2

Expression, Purification and Phosphorylation of Recombinant Proteins

In this Example, recombinant proteins were expressed, purified and phosphorylated. In these experiments, insect cells and baculoviruses were used. Baculovirus expression vectors were generated in this Example using the vectors in combination with linearized BaculoGold or AcMNPV wild-type DNA (Pharmingen). The viruses, their tags, and base vectors are listed in Table 1.

Cdc4ΔWD is a mutant version of Cdc4 that contains a stop codon at residue 566, which removes the last three WD-40 repeats. Gst-Cdc28HA (D154N), also referred to as "Gst-Cdc28HA(K−)," is a kinase-impaired form of Cdc28. In complexes with either Cln1 or Clb5, this kinase was found to exhibit <2% activity toward histone H1.

For expression of $His_6$Cdc34 and $His_6$-Sic1, plasmids were transformed into BL21 (DE3) cells (Novagen). One liter of cells were grown in LB containing 0.1 mg/ml ampicillin, at 37° C., until an $OD_{600}$ of 0.8 was reached. Expression was then induced with 400 mM IPTG for three hours. Cells were harvested by centrifugation (2,000×g, for 10 minutes), lysed in 70 ml of 20 mM sodium phosphate buffer (pH 7.5) containing 500 mM NaCl , and 0.1 mg/ml lysozyme (Sigma), and incubated for 45 minutes on ice. Insoluble material was removed by centrifugation (14,000× g, for 20 minutes). The lysate was then incubated with 0.5 ml $Ni^{+2}$-NTA (Qiagen) resin as directed by the manufacturer. The protein was eluted with 20 mM sodium phosphate (pH 6) containing 500 mM NaCl and 200 mM imidazole, and stored at −80° C.

TABLE 1

Baculovirus Expression Vectors

| Virus | Tag | Base Vector |
|---|---|---|
| Cak1 | None | pVL |
| Cdc4 | None | pBBIII |
| Cdc4ΔWD | None | pBBIII |
| Cdc4$^F$ | C-terminal Flag | pBBIII |
| Cdc34 | None | pBBIII |
| Cdc53$^M$ | N-terminal Myc | pBBIII |
| Clb5 | None | pVL |
| Cln1$^{HA}$ | C-terminal HA | pBBIII |
| Cln2$^{HA}$ | C-terminal HA | pVL |
| Gst-Cdc28$^{HA}$ | N-terminal Gst C-terminal HA | pVL |
| Gst-Cdc28$^{HA}$ (D154N) | N-terminal Gst C-terminal HA | pVL |
| Grr1$^{G10}$ | N-terminal $His_6$-G10 | pBBHis |
| $His^6$-Cks1 | N-terminal His6 | pVL |
| Sic1 | None | pBBIII |
| Skp1 | None | pVL |
| Skp1$^F$ | N-terminal Flag | pBBIII |
| Gst-Skp1 | N-terminal Gst | pVL |

For recombinant protein expression and assembly of complexes, $4 \times 10^5$ insect cells (Hi5, Invitrogen) were infected with the indicated virus combinations for 40 hours. These combinations included baculoviruses expressing Myc-tagged Cdc53 (Cdc53$^M$), Cdc34, Cdc4, and Skp1. Cells were then harvested and disrupted in lysis buffer (50 mM Tris-HCl (pH 7.5), 150 mM NaCl, 0.5% Nonidet P40, 10 mM NaF, 10 mM β-glycerol phosphate, 1 mM PMSF, and 5 μg/ml each leupeptin, antipain, and aprotinin). For isolation of protein complexes, typically about 3 ml of lysis buffer was used per $0.5 \times 10^8$ cells.

To examine the assembly of recombinant yeast proteins, 0.4 ml lysate were typically derived from $2 \times 10^6$ cells. In both cases, cell lysates were centrifuged for 2 minutes at 14,000×g, prior to affinity- or immuno-purification. Immunopurification was performed by incubating the lysates at 4° C. for 2 hours with 4 μg of the anti-Myc or anti-G10 antibody and 8 μl of Protein A-Sepharose, or with 8 μl of immobilized anti-Flag antibodies (Kodak; See, Example 1). Immune complexes were washed three times with 1 ml of lysis butter prior to SDS-PAGE.

For SDS-PAGE, an equal volume of 2×sample buffer (250 mM Tris (pH 6.8), 4% SDS, 20% glycerol, 10% 2-mercaptoethanol) was added to the samples to be tested, and boiled for 2 minutes. Samples were then electrophoresed in 12% polyacrylamide gels with 35 mA constant current. Proteins were transferred to nitrocellulose filters using a BioRad transfer apparatus in 50 mM Tris/glycine buffer (pH 8), containing 20% methanol, for three hours, at 350 mA. The nitrocellulose filters were then blocked with 5% non-fat dry milk solution for 1 hour, followed by incubation overnight with primary antibody. The antibody dilution used was 1:1000 for anti-Cdc4, anti-Cdc34, anti-gene10, anti-Sic1, anti-myc, and anti-HA; the anti-Skp1 antibody was diluted 1:4000. Blots were washed in TBST (20 mM Tris (pH 8), 100 mM NaCl, 0.5% Tween-20) for 30 minutes, and then incubated with either goat anti-rabbit conjugated horseradish peroxidase (HRP) or rabbit anti-goat conjugated HRP (Promega), as appropriate, at a dilution of 1:25,000, for 30 minutes. Immunoblots were then washed with TBST for 30 minutes, and developed using enhanced chemiluminescence detection (Amersham) as described by the supplier.

As shown in FIG. 1A, in the presence of all four proteins (Cdc53$^M$, Cdc34, Cdc4, and Skp1), anti-CdcS3$^M$ complexes contained Cdc4, Cdc34, and Skp1. However, in the absence of Skp1, only low levels of Cdc4 bound to Cdc53$^M$, regardless of the presence of Cdc34 (FIG. 1A, lanes 7 and S). This result was confirmed through the analysis of Cdc53$^M$ association with anti-Cdc4 immune complexes (See, FIG. 1B). Thus, Skp1 was shown to facilitate association of Cdc53 with Cdc4. In contrast, both Skp1 and Cdc34 can simultaneously associate with Cdc53$^M$ in the absence of other yeast proteins (See; FIGS. 1A and 1C). Together, these data indicated that Cdc34, Cdc53, Skp1, and Cdc4 form a multiprotein complex.

A. Sic1/Clb5/Gst-Cdc28HA(K−) Complexes

Sic1/Clb5/Gst-Cdc28HA(K−) complexes were purified from 4×10$^8$ cells, as described by Connell-Crowley et al. (Connell-Crowley et al., Mol. Biol. Cell., 8:287–301[1997]). Briefly, eight T-150 flasks of insect cells (Highfive, Invitrogen) were infected with 1 ml each of baculoviruses expressing either GST-Cdc28HA, Cln1HA, Cks1, and Cak1, or baculoviruses expressing Gst-Cdc28HA(K−), Clb5, and Sic1. After 40 hours, the cells were lysed at 4° C., in 6 ml of NETN (20 mM Tris-HCl, pH 8, 100 mM NaCl, 1 mM EDTA, 0.5% NP-40, 5 mM NaF, 30 mM p-nitrophenylphosphate, 1 μg/ml each leupeptin and antipain, and 1 mM PMSF). Lysates were cleared by centrifugation at 14,000×g for 10 minutes. Supernatants were rotated with 0.2 ml of GSH-Sepharose for 60 minutes at 4° C., and the beads were washed three times with 2 ml of the lysis buffer, followed by two washes with 100 mM Tris (pH 8), 100 mM NaCl. Proteins were then eluted with 0.2 ml of 100 mM Tris (pH 8), 100 mM NaCl, 40 mM glutathione (Sigma), and 10% glycerol. The proteins were then stored at −80° C. until use.

B. Gst-Cdc28HA/ClnHA/Cks1 and Gst-Cdc28HA(K−)/ClnHA/Cks1 Complexes

Gst-Cdc28HA/ClnHA/Cks1 (i.e., "ClnHA/Gst-Cdc28HA/Cks1" in the legend for FIG. 2A) and kinase impaired Gst-Cdc28HA(K−)/Cln1HA/Cks1 complexes were prepared as described above, as were cells co-infected with viruses expressing appropriate proteins, and CAK1 expressing virus generated from a cDNA generously provided by C. Mann (See, Thuret et al., Cell 86:565–576 [1996]). The presence of Cks1 and Cak1 resulted in a 5-fold increase in the yield of active Cln/Cdc28 kinase complexes, as purified after insect cell co-infection (determined using histone HI as a substrate). FIG. 2A shows an SDS-PAGE analysis of purified Cdc28HA/Cks1. In this Figure, the asterisk indicates the position of endogenous GST protein.

C. Phosphorylated Sic1 Complexes

Phosphorylated Sic1 complexes were generated by incubating 2.5 μM Sic1/Clb5/Gst-Cdc28HA(K−) with Gst-Cdc28HA/Cln1HA/Cks1 (50 nM) and 1 mM ATP in kinase buffer (50 mM Tris HCl (pH 7.5), 50 mM NaCl, 10 mM MgCl$_2$) for 45 minutes at 25° C. Control unphosphorylated Sic1 complexes were produced in an identical fashion by omitting Cln1 kinase. Cln/Cdc28 autophosphorylation was performed by incubating 200 nM Cln/Cdc28 complexes with 1 mM ATP in kinase buffer at 25° C. for 1 hour. To generate phosphorylated Sic1 free of Cln/Cdc28 kinase, bacterial Sic1 (0.5 μM) was incubated with 2 mM ATP and Cln2/Gst-Cdc28/Cks1 immobilized on GST-Sepharose (Pharmacia) for 60 minutes at 37° C. Forty ng of phosphorylated Sic1 were removed from the beads for use in ubiquitination reactions, at a final concentration of 1 nM. For $^{32}$P-labeling of Sic1 and Cln1 proteins, kinase reactions were performed at 25° C. for 30 minutes, using 50 μM (γ-$^{32}$P ATP (0.3 nCi/pmol) followed by incubation with 1 mM unlabeled ATP for an additional 30 minutes.

FIG. 2B shows the gel results of phosphorylation of Sic1 by Cln1/Cdc28 complexes in vitro. The result for Sic1/Clb5/Gst-Cdc28HA(K−) incubated with ATP are shown in lane 1, while the result for Cln1/Cdc28 and ATP is shown in lane 2. Lane 3 shows the reaction products obtained when Cln1/Cdc28 complexes alone were incubated with γ-$^{32}$P ATP. In lanes 4 and 5, the results from experiments in which smaller amounts of Sic1 phosphorylation reactions with 50 nM of Sic1 were performed in the presence of γ-$^{32}$P ATP.

D. Grr1 Complexes

The Grr1 complexes were prepared by infecting one T-150 flask of insect cells as described above, with baculoviruses expressing Grr1G10, Skp1, and Cdc53$^M$, or variations thereof. Forty hours after infection, the cells were lysed in 3 ml of NETN, and the lysates cleared by centrifugation at 14,000×g for 10 minutes. Ten percent of each lysate was used for immunoprecipitation with 5 μg of anti-gene 10 antibodies (Novagen), and 8 μl of protein A-Sepharose (4° C., for 90 minutes). The immune complexes were washed three times with 1 ml NETN prior to use in binding experiments or ubiquitination reactions.

The complexes were immunoprecipitated with either (A) a Myc tag on Cdc53 (Cdc53$^M$) using anti-Myc antibodies or (B) a Flag tag on Cdc4 (Cdc4$^F$) as described in Example 3. Immune complexes were immunoblotted and probed with anti-Myc to detect Cdc53$^M$, anti-Cdc4, anti-Cdc34, and anti-Skp1 as described in Example 3 (See, FIG. 1).

EXAMPLE 3

In Vitro Binding Assays

Binding reactions were performed at 4° C. for 1 hour, in 100–250 ml mixtures containing appropriate immunopurified complexes prepared as described in Example 2, and affinity purified Sic1 (20 nM) or Cln (2 nM) complexes. Associated proteins were then washed three times with 1 ml of lysis buffer prior to SDS-PAGE and immunoblotting, were performed as described above.

In some experiments, $^{32}$P-labeled Sic1 or Cln complexes were employed at similar concentrations, and detected by autoradiography and phosphoimager analysis. Based on protein staining with Coomassie Blue or silver, the quantities of proteins in anti-Skp1$^F$ immune complex from Skp1$^F$/Cdc53$^M$/Cdc4 expression cells was estimated to be: Skp1$^F$ (1 μg), Cdc53$^M$ (200 ng), and Cdc4 (200 ng). Likewise, the levels of proteins in the anti-Grr1G10 complex were: Grr1G10 (100 ng), Cdc53$^M$ (40 ng), and Skp1 (20 ng).

In additional experiments, insect cells were co-infected with constant quantities of baculovirus expressing Skp1$^F$ and increasing quantities of baculoviruses expressing either Cdc4, or a C-terminal truncated form of Cdc4 lacking the last three WD-40 repeats (i.e., Cdc4ΔWD; lanes 12–17). Lysates were immunoprecipitated with anti-Flag antibodies to precipitate Skp1$^F$ complexes. Binding reactions with phosphorylated Sic1 complexes and detection of bound protein were performed as described above.

FIG. 2C indicates that phosphorylation of Sic1 is required for its association with Cdc34/Cdc53/Skp1/Cdc4 complexes. As shown in this Figure, phosphorylated Sic1 efficiently associates with Cdc53/Skp1/Cdc4 complexes, and this association is dependent upon the presence of Skp1 (See, FIG. 2C, lanes 6 and 8). Typically, 10–20% of the input phosphorylated Sic1 was bound at about 20 nM Sic1. In contrast, the extent of binding of unphosphorylated Sic1 (lane 7) was comparable to that observed in control immune complexes generated from uninfected cells (lane 3) and was <1% of the input Sic1. Consistent with the results in FIG. 1, the level of Cdc4 found in immune complexes lacking Skp1 were >10-fold lower than that found in the presence of Skp1. These data suggest that Cdc4 and/or Skp1 function as binding factors for Sic1 and that association of Sic1 with this complex requires phosphorylation by Cln1/Cdc28.

Figure 2D:
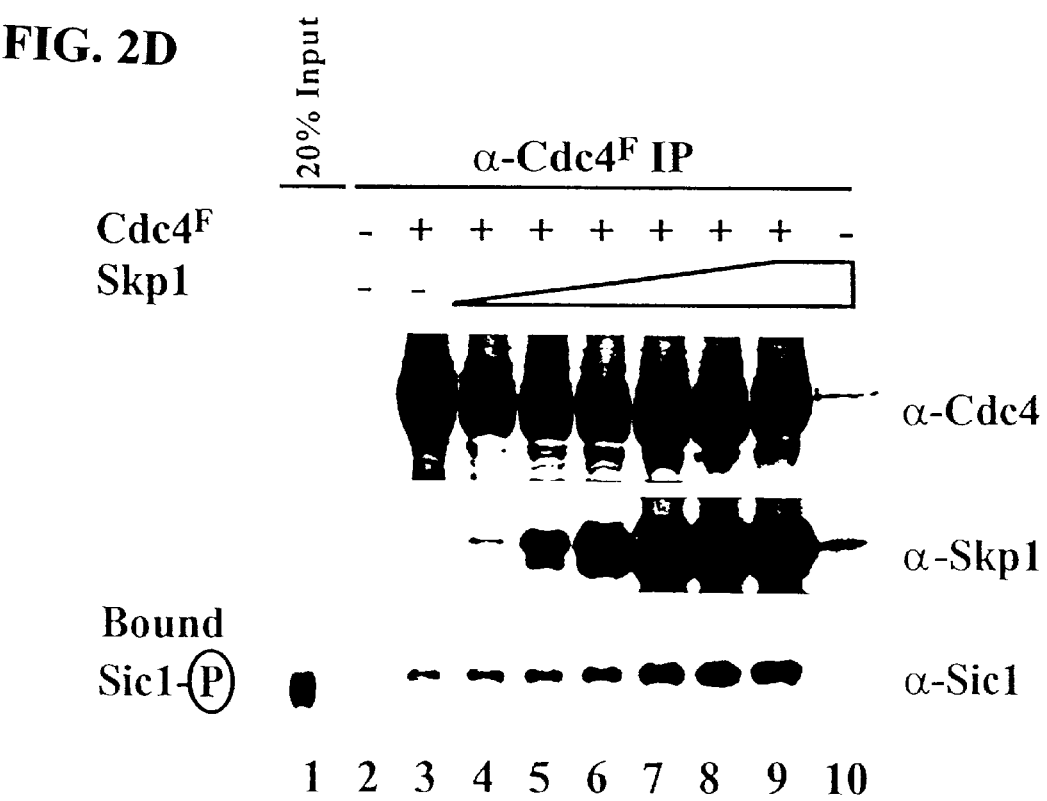
FIG. 2D shows immunoblot results indicating that association of phosphorylated Sic1 with Cdc4 is enhanced by Skp1.

FIG. 2D shows that association of phosphorylated Sic1 with Cdc4 is enhanced by Skp1. In this Figure, lanes 3–9 contain anti-Flag immune complexes derived from cells infected with constant high quantities of a baculovirus expressing Cdc4$^F$, while lanes 4–10 contain increasing quantities of a baculovirus expressing Skp1 in in vitro binding reactions with purified Cln1/Cdc28-phosphorylated Sic1. While Skp1 alone did not interact with Sic1, it stimulated association of Sic1 with Cdc4 by about 5-fold (FIG. 2D). The weak association of Sic1 with Cdc4 alone (FIG. 2D, lane 3) may reflect the participation of an insect cell Skp1 homolog. The results described herein clearly demonstrate a positive contribution of Skp1 in the Cdc4/Sic1 interaction.

Figure 2E:
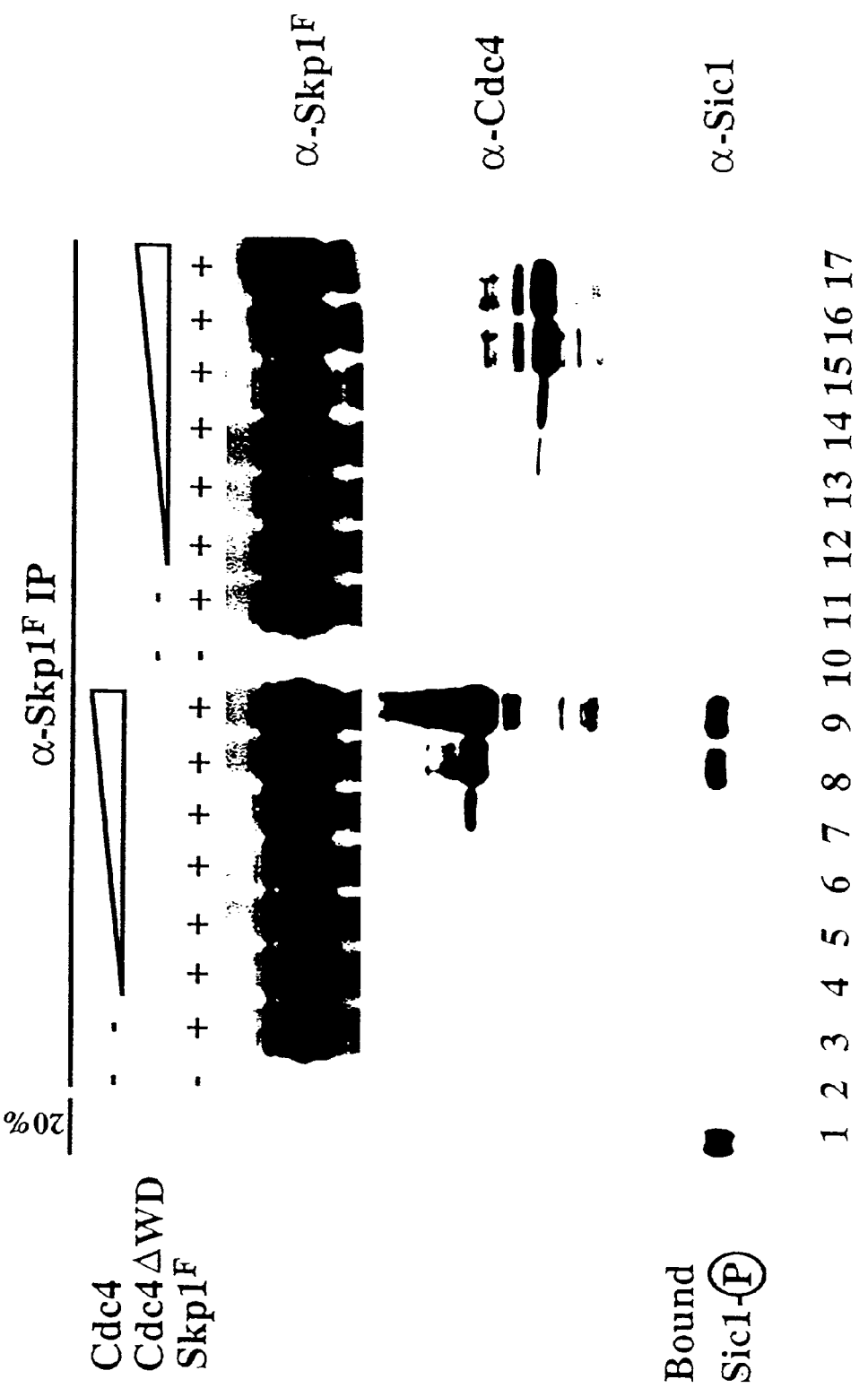
FIG. 2E shows immunoblot results indicating that association of phosphorylated Sic1 with Skp1 requires the WD-40 repeats of Cdc4.

FIG. 2E shows that association of phosphorylated Sic1 with Skp1 requires the WD-40 repeats of Cdc4. In this Figure, lanes 4–9 contain proteins obtained from insect cells co-infected with constant quantities of baculovirus expressing Skp1$^F$, and increasing quantities of baculoviruses expressing Cdc4, while lanes 12–17 contain lysates from cells co-infected with constant quantities of baculovirus expressing Skp1$^F$ and increasing quantities of baculoviruses expressing a C-terminal truncated form of Cdc4 lacking the last three WD-40 repeats (i.e., Cdc4ΔWD). Association of phosphorylated Sic1 with anti-Skp1$^F$ immune complexes was absolutely dependent upon the presence of Cdc4 (See, FIG. 2E, lanes 3 and 9). Moreover, deleting the last three WD-40 repeats from the C-terminus of Cdc4 abolished its ability to associate with phosphorylated Sic1 (FIG. 2E, lanes 10–16). Therefore, Cdc4 functions as the specificity factor for binding of phosphorylated Sic1 and the Cdc4-Sic1 interaction requires an intact WD-40 repeat domain in Cdc4.

EXAMPLE 4

Ubiquitination Assays

In this Example, ubiquitination reactions were conducted. In these experiments, Ni$^{2+}$-NTA resin was used to isolate ubiquitinated proteins from extracts of wild-type cells or sic1 deletion mutants expressing His$_6$-Ub$^{RA}$ or Ub$^{RA}$ (Willems et al., [1996], supra). In addition, once the strategy to generate Cdc4/Skp1/Cdc53 complexes that recognized phosphorylated Sic1 was developed, experiments to determine whether these complexes can catalyze ubiquitination of Sic1 in vitro when supplemented with Cdc34, E1, ATP, and ubiquitin were conducted.

In some experiments, bacterial Sic1 was used and where indicated, was phosphorylated with soluble or immobilized Gst-Cdc28HA/Cln2HA prior to use. Bacterial Sic1 ubiquitination reactions employed 100 nM yeast E1 (a gift from S. Sadis and D. Firley, Department of Cell Biology, Harvard Medical School).

A. Ubiquitination of Sic1 In Vivo

To identify Sic1-ubiquitin conjugates in vivo, 200 ml ($10^7$ cells/ml) of wild-type (MT235), or a sic1 deletion (MT767) cells expressing either pCUP1-UB1$^{RA}$ (<pUB204>) or pCUP1-UBPI$^{HIS-MYC-RA}$ (<pUB223>) were prepared, and lysates were generated in 50 mM Tris-HCl (pH 7.5), 100 mM NaCl, 0.1% NP-40, 1 mM PMSF, 0.6 mM dimethylaminopurine, 1 μg/ml leupeptin, 1 μg/ml pepstatin, 10 μg/ml Tosyl-phenyl chloromethyl ketone and 10 μg/ml soybean trypsin inhibitor as described by Willems et al. (Willems et al., Cell 86:453–463 [1996]). Briefly, 8 μg of yeast protein was incubated with 12 μl of N+$^2$ NTA beads (Qiagen) for 1 hour at 4° C., as described by the manufacturer. The beads were then washed 3 times in lysis buffer, 1 time in high salt buffer (50 mM Tris-HCl, pH 8.0, 0.5 M NaCl), and the proteins were eluted with 10 μl of 100 mM Tris-HCl, pH 6.8, 1% SDS, 100 μM DTT, 100 μM EDTA. Proteins were separated by SDS-PAGE and immunoblotted with anti-Sic1 antibodies, as described above.

FIG. 3 shows that phosphorylated Sic1 is ubiquitinated in vivo and in vitro with purified Cdc34 E2 and Cdc53/Skp1/Cdc4 complexes. In this Figure, the position of Sic1 and Sic1-ubiquitin conjugates are indicated (i.e., "Sic1" and "Sic1-Ub," respectively).

B. Reconstitution of the Sic1 Ubiquitination Pathway Using Recombinant Proteins

Ubiquitination reactions contained immune complexes prepared from 2×10$^6$ cells and equilibrated with ubiquitination buffer (100 mM Tris-HCl (pH 7.5), 5 mM MgCl$_2$, 0.6 mM DTT), 500 nM bacterial Cdc34, 300 nM human E1 (a gift from M. Rolfe, Mitotix), 2 mM ATP, and 7 mM yeast ubiquitin (Sigma) or Gst-UB$^{RA}$ (purified from bacteria expressing GEX-U6$^{RA}$ [provided by M. Tyers, University of Toronto], and the method described in Example 1 for GST-Skp1), and 80 ng of Sic1 complexes in a final volume of 14 μl, excluding bead volume. The human E1 purification was described by Rolfe et al. (Rolfe et al., Proc. Natl. Acad. Sci. USA 92:3264–32637 [1995]). Reactions were allowed to proceed at 25° C. for 1 hour or as indicated, quenched with 2×sample buffer (250 mM Tris (pH 6.8), 4% SDS, 20% glycerol, and 10% 2-mercaptoethanol), and analyzed by SDS-PAGE and immunoblotting with anti-Sic1 antibodies as described above.

The results indicated that in the presence of all reaction components, phosphorylated Sic1 was efficiently converted to higher molecular weight conjugates detectable with anti-Sic1 antibodies (See, FIG. 3B, lane 6; and FIG. 3C, lane 5). In contrast, unphosphorylated Sic1 was not detectably ubiquitinated. Sic1 ubiquitination absolutely required Cdc34, Cdc4, Cdc53, Skp1, E1 and ubiquitin (See e.g, FIG. 3B and FIG. 3C). The pattern of high molecular weight Sic1 conjugates obtained in reactions with ubiquitin was different from that observed when Gst-Ub$^{RA}$ was used as the ubiquitination source as shown in lanes 5 and 11 of FIG. 3C. These results confirm that the high molecular weight forms observed are products of ubiquitination. With Gst-Ub$^{RA}$, the Sic1 reaction products were integrated into a ladder of bands differing by approximately 35 kDa, the size of Gst-Ub$^{RA}$ (See, FIG. 3C, lane 11).

The ubiquitination reaction was time dependent and the reaction efficiency ranged from 10–40% of the input Sic1 protein (FIGS. 3B and 3C). When the reaction was performed with pre-bound Sic1, the efficiency was greater than 50%. In addition, greater than 50% of the Sic1 ubiquitin conjugates formed after 60 minutes were found to have dissociated from the Cdc4/Skp1/Cdc53 complex. In addition, neither Gst-Cdc28, Clb5, Cdc53, Skp1, or Cdc4 formed ubiquitin conjugates under the reaction conditions employed, although Cdc34 was ubiquitinated as previously reported (Haas et al., J. Biol. Chem., 266:5104–5112 [1991]).

C. Ubiquitination of Sic1 in Association with Clb5-Cdc28 Complexes

To test whether Sic1 ubiquitination requires association with Clb5/Cdc28 complexes, ubiquitination reactions using Sic1 produced in bacteria, with or without phosphorylation with Cln2/Cdc28 were performed as described above, with yeast E2 replacing human E1. To verify the absence of Cln2HA/Cdc28HA in the ubiquitination reaction, Sic1 proteins were also irnmunoblotted with anti-HA antibodies.

The results shown in FIG. 3D indicate that ubiquitination of Sic1 does not require that Cln/Cdc28 be present in the ubiquitination reaction, nor that Sic1 be associated with Clb5/Cdc28. In this Figure, lane 1 contains Sic1 purified from bacteria, while lane 2 contains Sic1 treated with soluble Cln2/Gst-Cdc28, and lane 3 contains immobilized Cln2/Gst-Cdc28. Use of phosphorylated Sic1 that was free of Cln2 kinase is indicated by an asterisk (lanes 3 and 9). As in the case of Sic1 assembled in insect cells with Clb5/Cdc28, phosphorylated Sic1 from bacteria was efficiently ubiquitinated, with greater than 90% of the Sic1 forming ubiquitin conjugates (lane 8), and ubiquitination absolutely required Sic1 phosphorylation (lane 4).

Although phosphorylation of Sic1 was required for its recognition by Cdc4 and Skp1, it remained possible that Cln/Cdc28, present in small amounts in the ubiquitination reaction, is also required for additional steps in the ubiquitination process, for instance, to phosphorylate the ubiquitination machinery. To rule out this caveat, bacterial Sic1 was treated with Cln2/Gst-Cdc28 complexes immobilized on Gst-Sepharose beads, removed from the beads prior to use in ubiquitination reactions, and determined to be free of soluble kinase by immunoblotting with anti-HA antibodies. These results are shown in FIG. 3D, lane 3. Sic1 phosphorylated in this manner was also efficiently ubiquitinated (See, FIG. 3D, lane 9). These data indicate that Sic1 phosphorylation constitutes the primary requirement of Cln/Cdc28 kinases in Sic1 ubiquitination in the in vitro reaction.

D. Clb5/Cdc28-phosphorylated Sic1 as a Substrate for Ubiquitination

In these experiments, it was found that Clb5/Cdc28-phosphorylated Sic1 was also a substrate for ubiquitination. In these experiments, constant amounts of Sic1 were treated with increasing amounts of Clb5/Cdc28, until the kinase was in excess as determined by histone kinase assays. Under these conditions, Sic1 electrophoretic mobility was reduced (FIG. 3E, lanes 1–6, top), as determined by immunoblotting.

Aliquots of differentially phosphorylated Sic1 were used in ubiquitination reactions with immunopurified Cdc53$^M$/Cdc4/Skp1 complexes supplemented with Cdc34, E1, ubiquitin, and ATP for 30 minutes, as described above (See, FIG. 3E, lanes 1–6). As a negative control, partially phosphorylated Sic1 corresponding to the Sic1 protein in lane 5 (top) of FIG. 3E, was reacted in the absence of Cdc34 (lane 7) or the Cdc53$^M$/Cdc4/Skp1 complex (FIG. 3E, lane 8). Sic1 ubiquitination was determined by immunoblotting with anti-Sic1 antibodies (FIG. 3E, bottom).

Although Sic1 is an inhibitor of Cdc28/Clb5 complexes, when the kinase complex was in excess of Sic1, Sic1 was phosphorylated as determined both by reduced electrophoretic mobility (See, FIG. 3E) and $^{32}$p incorporation. This result may explain the fact that overexpression of CLB5 can drive S-phase entry in cln-cells, and suggests that active Clb5/Cdc28 formed during Sic1 destruction may collaborate with Cln/Cdc28 to complete the Sic1 ubiquitination process.

E. Sic1 Binding and Ubiquitination with Grr1

In these experiments, the Cdc4 was substituted with another F-box protein (Grr1) in order to determine if this protein could support Sic1 binding and ubiquitination. Grr1 has an F-box near car its N-terminus and can interact simultaneously with Skp1 and Cdc53 when co-expressed in insect cells (See e.g., Figure A).

These experiments were conducted as described above, with the exception being that Grr1 was substituted for Cdc4 (approximately 100 ng). Proteins were separated by SDS-PAGE, and blotted with anti-Skp1 anti-Myc to detect Grr1G10 and Cdc53$^M$, with anti-Skp1 antibodies.

It was found that that Grr1 and Cdc4 with Skp1/Cdc53 are mutually exclusive. In contrast with Cdc4, it was not possible to demonstrate enhancement of the Grr1/Cdc53 interaction in insect cells by co-expression of Skp1, even though Skp1 assembled with these complexes. Importantly, Grr1 assembled with Cdc53/Skp1 complexes was unable to associate with phosphorylated Sic1, and was unable to support ubiquitination of phosphorylated Sic1 complexes in the in vitro system with purified proteins under conditions where Cdc4 readily facilitated Sic1 binding and ubiquitination (See, FIGS. 4B and 4C). Therefore, F-box proteins display selectivity toward particular targets.

FIG. 4A shows that Grr1 can associate with Skp1 and Cdc53, while FIG. 4B shows that phosphorylated Sic1 associates with Cdc4 but not Girl-containing complexes. In this Figure, lanes 2–5 contain anti-Skp1$^F$ immune complexes derived from insect cells infected with the indicated baculovirus combinations were used for binding reactions with $^{32}$P-labeled Sic1 complexes. Ten percent of the input Sic1 complex (lane 1) was included as a control. The presence of Cdc4, Skp1, Cdc53, and Grr1 was verified by immunoblotting.

Figure 4C:
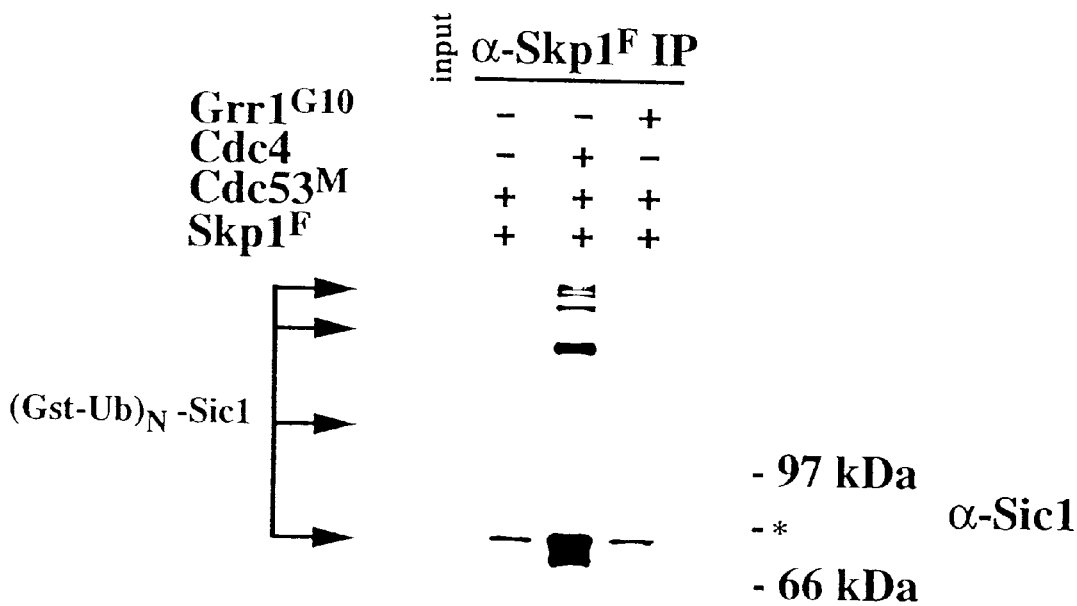
FIG. 4C shows an immunoblot indicating that Cdc4, but not Grr1, supports ubiquitination of Sic1 in vitro.
Figure 4D:
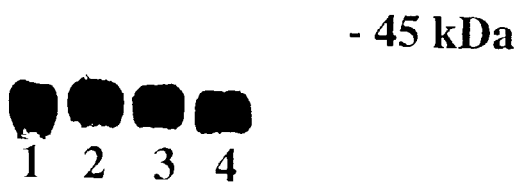
FIG. 4D shows an immunoblot used to verify the presence of reaction components derived from immunoprecipitation (the blot used for ubiquitination assays was reprobed to detect Grr1G10, $Cdc53^m$, and Cdc4).
Figure 4D:
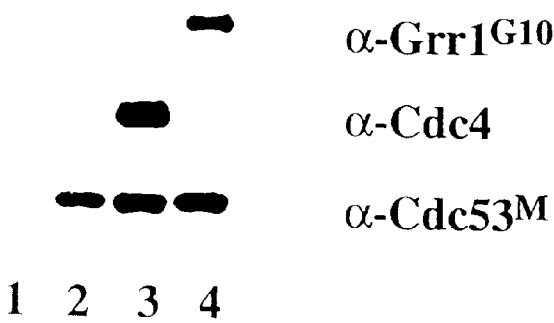

FIG. 4C shows that Cdc4, but not Grr1, supports ubiquitination of Sic1 in vitro. The indicated anti-Skp1$^F$ immune complexes were used in ubiquitination assays as described for FIG. 3 (above) employing Gst-Ub$^{RA}$ as the ubiquitin source. Finally, FIG. 4 shows the results verifying the presence of reaction components derived from immunoprecipitation (in this Figure, the blot used for ubiquitination assays was reprobed to detect Grr1G10, Cdc53$^M$, and Cdc4).

EXAMPLE 4

Binding of Grr1 to Cln1 and Cln2

In this Example, the binding of Grr1 to Cln1 and Cln2 was investigated. In particular, experiments were conducted in order to determine whether Grr1 binds to Cln1 and/or Cln2 in a phosphorylation-dependent manner. Indeed, the finding that Sic1 is recognized by the F-box protein Cdc4, together with a genetic requirement for the F-box protein Grr1 in Cln destruction, led to these experiments to examine whether Grr1 functions in recognition of phosphorylated Clns.

To generate Cln proteins for binding reactions, Cln/Gst-Cdc28/Cks complexes were isolated from insect cells as described in Example 2B. In the presence of ATP, both Cln1 and Cln2 are autophosphorylated, a modification that reduces their electrophoretic mobility (see below). To examine whether Grr1 can associate with phosphorylated Clns and to compare the extent of selectivity of Grr1 and Cdc4 toward Cln binding, anti-Skp1$^F$ immune complexes from cells co-expressing Grr1 or Cdc4 in the presence or absence of Cdc53 prepared as described above, were used in binding reactions with $^{32}$P-labeled Cln1 or Cln2 kinase complexes. $^{32}$P-labeled Sic1 was used as a control for Cdc4 binding.

As shown in FIG. 5A, both Cln1 and Cln2 complexes associated with Grr1/Skp1$^F$/Cdc53 complexes with an efficiency of about 40% of the input Cln1 or Cln2 (FIG. 5A, lanes 5 and 12), and this association did not require Cdc53 (FIG. 5A, lane 16). In contrast, about 6% of the input Cln proteins associated with Cdc4/Skp1$^F$ complexes independent of the presence of Cdc53 (FIG. 5A, lanes 7, 11, and 15), compared with 1% association in the absence of an F-box protein (FIG. 5A, lanes 6, 10, and 14). The extent of selectivity of these F-box proteins for Cln and Sic1 is further reflected by the observation that Cln1 protein present in the phosphorylated Sic1 preparation was selectively enriched in Grr1 complexes (FIG. 5A, lane 4). In this Figure, controls for the extent of binding (indicated by the asterisk) were 20% of input Cln and 10% of input Sic1. The presence of all proteins in the binding reaction was confirmed by immunoblotting (FIG. 5B; in this Figure, complexes used for binding experiments in FIG. 5A were immunoblotted with the indicated antibodies to verify the presence of Cdc4, Grr1G10, Cdc53$^M$, and Skp1$^F$), and the quantities of Cdc4 and Grr1 were found to be comparable, based on Coomassie staining of SDS gels of immune complexes. Thus, Grr1 and Cdc4 display specificity toward physiological substrates.

Next, Grr1 alone or in complexes with Skp1 or Skp1/Cdc53 were immunoprecipitated from insect cell lysates and used in binding assays with phosphorylated or unphosphorylated Cln1 complexes prepared as described above. The results are shown in FIG. 5C. As shown, unphosphorylated Cln1 was produced in insect cells as a complex with kinase deficient Gst-Cdc28(K−), which minimized Cln1 autophosphorylation during expression, and allowed the role of phosphorylation to be tested. FIG. 5C, lane 1 shows that, as isolated, this Cln1 protein migrates as a homogeneous species at approximately 66 kDa. In contrast, phosphorylated Cln1 (FIG. 5C, lane 2) undergoes a dramatic mobility shift to approximately 80 kDa, consistent with in vivo observations. Lanes 4–11 contain anti-Grr1G10 complexes derived from the indicated insect cell infections used in binding reactions with either unphosphorylated CIN1HA complexes generated using kinase impaired Gst-Cdc28(K−) HA (FIG. 5C, lane 1) or phosphorylated Cln1HA/Gst-Cdc28HA complexes (FIG. 5C, lane 2) Anti-HA antibodies were used to detect Cln1HA and Gst-Cdc28HA. Twenty percent of the input Cln1HA complexes were run as controls (FIG. 5C, lanes 1 and 2). Cln1HA isolated from insect cells in complexes with active Cdc28 migrated as a series of modified forms, reflecting partial phosphorylation of Cln in vivo in insect cells (See, FIG. 2A). Incubation of such ClnHA/Cdc28HA complexes with ATP quantitatively shifts Cln1 HA to a single form migrating as an approximately 84 kDa protein. The blot was reprobed to verify the presence of Grr1G10, Cdc53$^M$, and Skp1$^F$.

Phosphorylated Cln1 (and its associated Cdc28 protein) efficiently associated with all Grr1 complexes (FIG. 5C, lanes 6, 8, and 10), but was absent from control binding reactions lacking Grr1 (FIG. 5C, lane 4). In contrast, the levels of unphosphorylated Cln1 associated with Grr1 complexes were comparable to that found in binding reactions lacking Grr1 (FIG. 5C, lanes 3, 5, 7, and 9).

It was also determined that purified Skp1/Cdc53/Grr1 complexes are not sufficient for Cln1 ubiquitination by Cdc34 in vitro. Thus, association of both Cln1 with Grr1 and Sic1 with Cdc4 was found to be greatly enhanced by phosphorylation. Anti-Skp1$^F$ immune complexes were purified from insect cells infected with the indicated baculoviruses and supplemented with E1, Cdc34, Gst-Ub$^{RA}$, ATP, and either $^{32}$-P-labeled Sic1 or Cln1, as described above (e.g., FIG. 3).

As shown in FIG. 5D, although the Grr1/Skp1/Cdc53 complex is capable of binding efficiently to phosphorylated Cln1, it was not competent for Cln1 ubiquitination when supplemented with Cdc34 and E1. Moreover, FIG. 5D shows that Cdc4 complexes that functioned in Sic1 ubiquitination also failed to catalyze ubiquitination of Cln1, despite the fact that Cln1 can associate, albeit weakly, with Cdc4 (See, FIG. 5A). In contrast, identical preparations of phosphorylated Cln1 protein were efficiently ubiquitinated in partially purified yeast lysates in a Cdc34 dependent manner (FIG. 5E), indicating that this preparation of Cln1 is competent for ubiquitination.

EXAMPLE 5

Ubiquitination of Phosphorylated Cln1

In this Example, preparations of phosphorylated Cln1 (as described above), were ubiquitinated in partially purified yeast lysates in a Cdc34-dependent manner.

Figure 5E:
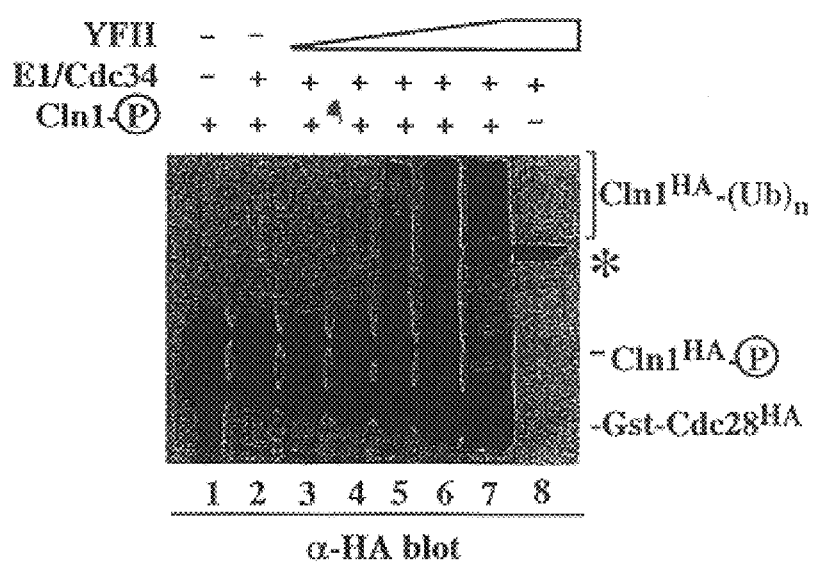
FIG. 5E is an immunoblot showing that phosphorylated Cln1 is ubiquitinated in a fractionated yeast extract system.

In these experiments, 0–100 μg YFII (a 250 mM NaCl eluate from a DEAE-cellulose column prepared exactly as described in Deshaies et al. [1995], supra) was supplemented with 500 nM Cdc34, 100 nM human E1, ubiquitin, and an ATP regenerating system (2 mM ATP, 600 mM creatine phosphate, and 0.15 mg/ml creatine kinase). The ubiquitination reaction was initiated by addition of 20 ng Cln1HA/Gst-Cdc28HA/Cks1. After incubation for 60 minutes at 25° C., the reactions were quenched and immunoblotted with anti-HA antibodies to detect Cln1HA and Gst-Cdc28HA. In FIG. 5E, the protein indicated by an asterisk is a yeast protein in YFII that cross-reacts with the anti-HA antibodies used. As indicated in this Figure, this preparation of Cln1 is competent for ubiquitination.

EXAMPLE 6

Identification of Human F-Box Proteins

In this Example, new human F-box proteins were identified, using a two hybrid system. The SKP1 open reading frame (as an NdeI/BamHI restriction fragment) was subcloned into pAS2 (See, Harper et al., Cell 75:805–816 [1993]). pAS2-SKP1 was transformed into yeast strain Y190, and this strain was then used in a two hybrid screen with a human breast cDNA library generated in λACTII as described by below.

Yeast strain Y190 was deposited with the ATCC and assigned number (96400). Y190 was grown in YPD medium (10 g/l yeast extract, 20 g/l peptone and 20 g/l dextrose) containing 10 mg/ml cycloheximide or on YPD plates (YPD medium containing 20 g/l agar) containing 10 mg/ml cycloheximide. Y190 contains two chromosomally located reporter genes whose expression is regulated by Gal4.

The first reporter gene is the *E. coli* lacZ gene which is under the control of the GAL1 promoter. The second reporter gene is the selectable HIS3 gene which encodes the enzyme imidazole glycerol phosphate (IGP) dehydrogenase. Yeast cells which express the HIS3 gene product can be selected by their ability to grow in medium lacking histidine (i.e., SC-his medium). The λ ACTII phage cloning vector was deposited with the ATCC and assigned number 87006. This λ ACTII phage cloning vector was deposited as a lysogen in JM107 cells which are grown in LB containing 50 μg/ml ampicillin.

Yeast cells (strain Y190) containing specific nutritional markers were grown on SC medium lacking one or more amino acids. SC medium lacking a particular amino acid is referred to as dropout media. SC medium is made using the following components: 10×YNB (67 g yeast nitrogen base without amino acids in 1 liter water, filter-sterilized and stored in the dark).

Dropout mixture components:

| adenine | 800 mg | arginine | 800 mg |
|---|---|---|---|
| aspartic acid | 4000 mg | histidine | 800 mg |
| leucine | 2400 mg | lysine | 1200 mg |
| methionine | 800 mg | phenylalanine | 2000 mg |
| threonine | 8000 mg | tryptophan | 800 mg |
| tyrosine | 1200 mg | uracil | 800 mg |

To make a dropout mixture, the above components are weighed out, leaving out the amino acids to be selected for, combined, and ground into a fine powder using a mortar and pestle.

SC-Trp plates comprise per liter: 870 mg dropout mixture (minus tryptophan), 20 g dextrose, 1 ml 1N NaOH, 20 g agar, water to 900 ml. The mixture is then autoclaved. After autoclaving, 100 ml 10×YNB is added just prior to pouring the plates.

The bacterial strain used was *E. coli* strain BNN132 (ATCC 47059). These cells were grown in LB (10 g/l bacto-tryptone [DIFCO], 5 g/l bacto-yeast extract [DIFCO], 10 g/l NaCl, pH adjusted to 7.0 with NaOH). *E. coli* strain BL21(DE3) (Invitrogen) was grown in LB.

As described in more detail below, the pAS2/Skp1/Y190 strain was transformed with 0.05 mg of plasmid library and 5 mg of carrier total yeast RNA, and transformants were plated on a minimal media lacking histidine, leucine, and tryptophan, but containing 25 mM 3-aminotriazole. After 5 days at 30° C., plasmids were recovered from β-galactosidase positive colonies (See, Harper et at, Cell 75:805–816 [1993]).

Also as described in more detail below, sequencing of cDNA inserts from positive plasmids revealed the presence of one cDNA containing significant sequence identity to Cdc4 in the F-box domain of Cdc4. This cDNA is referred to as "F3 gamma." Other F-box containing cDNAs were identified by searching the EST (expressed sequence tag) database, with the F-box region from F3 gamma. As novel F-box containing proteins were identified these were used to further search the EST database, in order to identify other novel F-box proteins. For some of these, both the human and mouse homologs were identified. It is contemplated that these new F-box proteins act as components of E3 complexes in mammalian cells (i.e., analogous to Cdc4 in budding yeast). Table 2 below lists the protein sequences identified in these experiments, while Table 3 provides the corresponding DNA sequences. FIG. 7 provides the alignments of these F-box proteins, with gaps indicated by dashes. Table 4 provides longer (i.e., more complete) cDNA and amino acid sequences for some of the F-box proteins identified in the preliminary experiments. The sequences included in Table 4 contain at least a large portion of the open reading frames (ORFs), and contain potential target binding domains. Both F1 and F2 contain leucine rich repeats (e.g., similar to Grr1). Thus, the present invention provides numerous sequences suitable for detection and identification of additional F-box proteins, as well as targets for intervention in the proteolysis pathways (e.g., for drugs and other compounds suitable for use to either enhance or reduce the efficiency and/or function of the F-box).

A. Generation of Human Breast Tissue cDNA Library in pACTII

In order to facilitate the isolation of F-box gene sequences using the yeast two-hybrid system, an human breast tissue cDNA expression library was constructed in the λ ACTII phage cloning vector. This cloning vector allows for the construction of cDNA libraries fused to sequences encoding the Gal4 transcriptional activation domain. The phage can be converted to a plasmid form (pACTII) as described below.

An human breast tissue cDNA library was constructed using λ ACTII as follows. Total RNA from breast tissue of an adult female obtained from reductive mammoplasty was provided by Dr. Anne Bowcock (University of Texas Southwestern Medical Center). PolyA+ mRNA was produced using an mRNA isolation system (GIBCO-BRL). cDNA synthesis was accomplished using a directional cDNA synthesis kit from Stratagene as described by the manufacturer.

After the synthesis of the second strand, the cDNA (in a volume of 400 μl) was spermine precipitated by the addition of 22 μl of 100 mM spermine. The mixture was incubated on ice for 30 min and then pelleted by centrifugation in a microcentrifuge (Eppendorf) for 15 min at 4° C. The cDNA pellet was washed three times for 30 min/wash with 1 ml of spermine wash buffer (70% ethanol, 10 mM Mg (Ac)$_2$, 0.3 M NaAc at pH 7) and once with 1 ml of 70% ethanol. The cDNA was then dissolved in 50 μl of TE buffer (10 mM Tris-HCl, pH 8.0, 1 mM EDTA).

The ends of the cDNA were made blunt by treatment with T4 DNA polymerase using conditions recommended by the manufacturer (Stratagene). Following treatment with T4 DNA polymerase, 5 μl of 0.5 M EDTA was added and the mixture was extracted with phenol/chloroform and precipitated with ethanol.

The precipitated cDNA, approximately 4 μg, was resuspended in 7 μl of TE buffer and then ligated to 2 μg of a kinased adapter oligonucleotide in a total volume of 10 μl at 4° C. overnight (12–18 hr). The hybridized oligonucleotide pair contained an EcoRI overhang. For example, the oligonucleotide CGCGCG hybridized with AATTCGCGCG (SEQ ID NO:59) will create a suitable EcoRI linker.

Following the ligation reaction, 170 μl of TE buffer, 20 μl of 1 M KCl and 10 μl of 100 mM spermine were added. The mixture was incubated on ice for 30 min and precipitated and washed as described above. The adapted cDNA was resuspended in 20 μl of TE buffer and digested with XhoI prior to electrophoresis on a 1% LMA gel. cDNA having a length of 600 bp or longer was excised from the gel and purified using standard techniques prior to ligation into λ ACTII arms.

cDNA (0.1 μg) was ligated with 2 μg of λ ACTII plasmid DNA prepared as follows. One hundred micograms of λ ACTII plasmid DNA was digested with XhoI and EcoRI; the digestion products were then precipitated with ethanol, briefly dried and then resuspended in 190 μl of TE buffer. Ten microliters of 10 mM spermine were added to the side of the tube and the contents were mixed by rapid inversion of the tube. An immediate and obvious precipitate formed and was pelleted by centrifugation for 2 sec in a tabletop microcentrifuge. The pellet was then washed with spermine wash buffer followed by a wash with 70% ethanol as described above. The washed pellet was resuspended in 100 µl of TE buffer. This preparation of λ ACTII plasmid DNA was then used for ligation into the cDNA containing adapters (prepared as described above)

The ligation of the adapted cDNA and digested λ ACTII plasmid DNA was performed in a volume of 4 µl at 4° C. overnight. The ligation mixture was packaged using one Gigapack Gold packaging extract (Stratagene) according to the manufacturer's instructions. Approximately $1 \times 10^8$ total recombinants were obtained. The phage library was amplified on the LE392 strain of *E. coli* (Stratagene).

Automatic subcloning conversion of the cDNA library in λ ACTII into plasmid (pACTII) was accomplished by the incubation of $10^9$ phage particles with 2 ml of a fresh overnight culture of *E. coli* strain BNN132 (ATCC 47059) in 10 mM $MgCl_2$ for 30 min at 30° C. without shaking. Two milliliters of LB (10 g/l bacto-tryptone, 5 g/l bacto-yeast extract, 10 g/l NaCl, pH adjusted to 7.0 with NaOH) was then added and the cells were incubated with shaking for 1 hr at 30° C. The cells were then plated on ten 150 mm LB plates (15 g/l bacto-agar in LB) containing 50 µg/ml ampicillin and incubated overnight at 37° C.

Ampicillin-resistant cells were collected by scraping the plates; the cells were then added to 3 liters of terrific broth (12 g/l bacto-tryptone, 24 g/l bacto yeast extract and 100 ml/l of a solution comprising 0.17 M $KH_2PO_4$, 0.72 M $K_2HPO_4$) containing 50 µg/ml ampicillin. The culture was grown to stationary phase and plasmid DNA was isolated using CsCl density gradients by standard methods (J. Sambrook et al., supra, at pp. 1.33–1.48)

B. Isolation of F-Box Sequences

In this portion of the Example, an improved version of the yeast two-hybrid system was employed to identify proteins that bind to Skp1. The two-hybrid system employs genetic selection to allow the isolation of interacting proteins. The use of genetic selection for the detection of interacting proteins allows much larger cDNA libraries to be screened for associating clones than could be accomplished using other techniques (i.e., screening expression libraries, such as λgt11, with labelled proteins).

The improved two-hybrid system employs the yeast strain Y190 as the recipient cell line. The yeast strain Y190 contains two chromosomally located reporter genes whose expression is regulated by Gal4. The first reporter gene is the *E. coli* lacZ gene, which is under the control of the GAL1 promoter. The second reporter gene is the selectable HIS3 gene. The two-hybrid system is improved by the use of an additional assay to eliminate false positives. "False positives" are defined as library clones that activate transcription in cells expressing fusions unrelated to the target protein (i.e., Skp1). To isolate interacting proteins, Y190 cells are first transformed with a first expression plasmid which encodes a fusion protein comprising a hybrid between the DNA-binding domain of the yeast transcription factor Gal4 (amino acids 1–147) and a target protein (i.e., a protein which is used to identify proteins capable of interacting with this target protein). The transformed Y190 cells are next analyzed to determine the effect of the introduction of the first expression plasmid. If the transformation of Y190 cells with the expression plasmid which expresses the target protein does not activate either the HJS3 or lacz reporter genes, this transformed strain can now be used for screening an activation domain cDNA library.

The activation domain library comprises plasmids capable of expressing the second hybrid molecules of the two-hybrid system. The second hybrids comprise fusion proteins containing the sequences encoding the Gal4 activation domain II (amino acids 768–881) fused to a cDNA library generated from human breast tissue (described above). When the Y190 cells transformed with the first expression plasmid are transformed with a second expression vector (from the expression library) capable of expressing a protein or portion of a protein which can bind to the Skp1 hybrid, transcription of the His3 and lacZ genes is activated as the binding of the second hybrid brings the Gal4 activation domain II in close proximity to the DNA binding domain of the Gal4 protein which is bound to the $UAS_G$ upstream of the His3 and lacZ genes on the chromosome.

In this two-hybrid system, Y190 cells were transformed with the expression plasmid pAS2-Skp1 using lithium acetate according to standard techniques (F. M. Ausubel, et al., *Short Protocols in Molecular Biology*, John Wiley & Sons, New York [1992], pp. 13–29–13,30). The expression plasmid, pAS2-Skp1 encodes a fusion protein comprising a hybrid between the DNA-binding domain of the yeast transcription factor Gal4 (amino acids 1–147) and the Skp1 molecule. This first hybrid acts as "bait" for the second hybrid molecule; the Gal4/Skp1 hybrid binds to the upstream activating sequence from GAL1 ($UAS_G$) sequences located upstream of the His3 and lacz genes in the host cell chromosome. Because the GAL4-Skp1 hybrid lacks trans-activating sequences, Y190 cells transformed with pAS1-Skp1 were His⁻ and white.

Y190 cells were transformed with the pAS2-Skp1 plasmid as follows. Y190 cells were grown in 5 ml of YPD medium (10 g/l yeast extract, 20 g/l peptone and 20 g/l dextrose) overnight to saturation at 30° C. The next day, a liter sterile flask containing 300 ml of YPAD medium (YPD containing 30 mg/l adenine hemisulfate) was inoculated with the overnight culture and grown overnight at 30° C. to a density of $1 \times 10^7$ cells/ml. The cells were then collected by centrifugation at 4000×g for 5 min at room temperature. The cell pellet was then washed by resuspending the cells in 10 ml sterile $H_2O$ followed by centrifugation at 5000×g for 5 min at room temperature. The washed cells were resuspended in 1.5 ml of LiAcTE (1 vol 10×TE buffer [100 mM Tris-HCl, 10 mM EDTA], pH 7.5), plus 1 vol of 10×LiAc stock solution (1M lithium acetate, pH 7.5) plus 8 vol sterile $H_2O$. Five micrograms of pAS2-Skp1 DNA and 200 µg carrier DNA (single-stranded, high molecular weight carrier DNA was prepared from salmon sperm DNA using standard protocols; yeast total RNA may also be used as a carrier) were placed in a sterile 1.5 ml microcentrifuge tube in a total volume of 20 µl. Two hundred microliters of the yeast suspension was added to the tube followed by the addition of 1.2 ml of a LiAcPEG solution (8 vol of 50% (w/v) polyethylene glycol, MW 3350 plus 1 vol of 10×TE buffer, pH 7.5 plus 1 vol 10×LiAc stock solution). The cells were then shaken for 30 min at 30° C., followed by a heat shock (15 min at 42° C.). Following the heat shock, the cells were collected by centrifugation for 5 sec at room temperature in a tabletop microcentrifuge. The cell pellet was the resuspended in 1 ml of TE buffer and 200 µl of the suspension were spread onto SC-Trp medium.

The transformed Y190 cells (Y190/pAS2-Skp1) were then transformed with a pACTII-human breast tissue cDNA library as described below. The plasmids contained within this library encode the second hybrids of the two-hybrid system. The second hybrids comprised fusion proteins containing the sequences encoding the Gal4 activation domain II (amino acids 768–881) fused to a cDNA library generated from human breast tissue. When a Y190/pAS2-Skp1 cell is transformed with a pACTII expression vector capable of expressing a protein or portion of a protein which can bind to the Gal4-Skp1 hybrid, transcription of the His3 and LacZ genes is activated as the binding of the second hybrid brings the Gal4 activation domain II in close proximity to the DNA binding domain of the Gal4 protein which is bound to the $UAS_G$ upstream of the His3 and lacZ genes on the chromosome.

Y190/pAS2-Skp1 cells were transformed with the pACTII-human breast cDNA library as follows. Briefly, the recipient strain (Y190/pAS2-Skp1 cells) were grown to mid-log phase ($1 \times 10^7$ cells/ml) in SC-Trp medium (SC medium lacking tryptophane). The $OD_{600}$ of this culture was determined and 1 liter of YPD medium was inoculated with enough of the culture such that in 2 generations the cell density became $1 \times 10^7$ cells/ml. The cells where pelleted by centrifugation and the pellet was resuspended in LiAcTE (the volume is not critical as this is a wash step). The cells were pelleted by centrifugation and the cells were resuspended in 25 ml of LiSORB (100 mM LiAc, 10 mM Tris-HCl (pH 8.0), 1 mM EDTA, 1 M sorbitol). The cells were then incubated for 30 min at 30° C. with shaking. The cells were then pelleted by centrifugation as described above and resuspended in 2.5 ml of LiSORB. After removing 100 μl of cells for a negative control, 50 μg of pACTII library DNA and 5 mg of yeast total RNA carrier was added. The mixture was mixed well and then incubated for 10 min at 30° C. without.shaking. The cells were then transferred to a 250 ml flask and 22.5 ml of LiAcPEG (LiAcTE containing 40% polyethylene glycol, MW 3350) was added and the suspension was well mixed. The flask was then placed in a 42° C. water bath for 12 min to heat shock the cells. Following the heat shock, the transformation mixture was added to 500 ml of SC-Trp, -Leu, -His medium and the culture was allowed to recover at 30° C. for 4 hours; at this point the cells are established as transformants. Next, $4 \times 10^5$ transformants were obtained by transformation of $1 \times 10^{10}$ Y190/pAS2-Skp1 cells with 50 μg of pACTII library DNA.

Transformants were subjected to selection for histidine prototrophy by plating 300 μl of the culture on 15 cm petri dishes containing SC-Trp, -Leu, -His medium containing 50 mM 3 amino-triazole (Sigma), and incubated for 30° C. for 3–5 days.

The rare surviving colonies were screened for their ability to produce β-galactosidase using a filter lift assay (L. Breeden and K. Nasmyth , Cold Spring Harbor Symp. Quant. Biol., 50:643–650 [1985]). Briefly, colonies were transferred onto nitrocellulose filters (Scheicher and Schuell, BA85 45 μm circular filters) by laying the filters onto plates containing the yeast colonies and allowing the filter to wet completely. The filters were lifted off the plates and then submerged in liquid nitrogen for 5–10 sec. The filters were then placed cell side up into a petri dish containing 3MM chromatography paper (Whatman) saturated 0.3 ml/square inch with a solution comprising 100 mM sodium phosphate, pH 7.0, 10 mM KCl, 0.7 mM magnesium sulfate, 10 mM 2-mercaptoethanol and 1 mg/ml X-gal (5-bromo-4-chloro-3-indolyl-β-galactoside). The filters were incubated at 30° C. until blue color developed (30 min to overnight). Positive (i.e., blue) colonies were then patched onto a master plate for further analysis.

Plasmids recovered from 20 His+ blue (i.e., lacZ expressing) colonies were sequenced from their 5' ends using the chain termination method in conjunction with the Sequenase® enzyme (U.S. Biochemicals); sequencing was performed according the manufacturer's instructions. The amino acid sequence was deduced from the nucleotide sequences located within the 20 inserts and were compared to sequences listed in the GenBank. One of these 20 clones were found to be related to the F-box protein met30 from *S. cerevisiae* in the F-box domain. The F-box region of Fgamma was used to search the EST database of Genbank, and identified two novel mammalian F-box-containing cDNAs (F13 Omicron and F14 Pi), in addition to two F-box proteins from *C. elegans* (CO2FS7 and YK18A11). The Genbank accession numbers for these four cDNAs are AA422959, AA462249, R12719, and D35163).

These novel F-box sequences were used to search the EST sequences listed in Genbank. This search yielded F7 Theta (AA008567), F1 alpha (F12916), F4 Delta (AA167804), TRCP (AA478504), F6 Eta (AA027176), F15 Rho (AA538102), F8 Iota (AA295683), MD6 (AA145853), and Skp2 homologs (U33761). These F-box protein sequences were then used in additional EST database searches and yielded sequences for F2 Beta (H58848), F5 Zeta (R17328), F9 Kappa (AA459120), F10 Lambda (AA501293), F11 Mu (AA069757), F12 Nu (AA000239), F16 Sigma (H49462), F17 Tau (AA381895), and F18 Phi (AA309734). cDNA clones in bacterial plasmids including pBluescript (Stratagene) were retrieved from the EST cDNA Image Consortium and subjected to sequence analysis using dideoxy DNA sequencing (See e.g., Sambrook et al., supra) to verify the F-box sequences. For three cDNAs (F1 alpha, F2 beta, and F4 delta, complete sequences of the available cDNA clones were obtained by standard primer walking (See e.g., Sambrook et al., supra).

This approach finds use in identification of other novel F-box containing proteins, either using cDNA libraries from other tissues or by performing additional database searches. The use of cDNA libraries from various tissues allows the identification of F-box proteins that are cell-type specific. Additional alternative approaches, such as expression screening of λgt11-based plaque libraries with Skp1 protein are also contemplated as methods for yielding novel F-box proteins.

TABLE 2

F-Box Sequences Identified

| Name, Source & Genbank # | Amino Acid Sequence | SEQ ID NO: |
|---|---|---|
| TRCP (human) AA478504 | LPARGLDHIAENILSYLDAKSLCAAELVCKEWYRVTS DGMLW | SEQ ID NO:1 |
| F1 (Alpha) (human) | LPKELLLRIFSFLDIVTLCRCAQISKAWNILALDGSNW | SEQ ID NO:3 |

TABLE 2-continued

F-Box Sequences Identified

| Name, Source & Genbank # | Amino Acid Sequence | SEQ ID NO: |
|---|---|---|
| F12916 F2 (Beta) (human) | LPYELIQLILNHLTLPDLCRLAQTCKLLSQHCCDPLQY | SEQ ID NO:5 |
| H58848 F2 (Beta) (mouse) | LPYELIQLILNHLSLPDLCRLAQTCRLLHQHCCDPLQY | SEQ ID NO:7 |
| F3 (Gamma) (human) | LPTDPLLLILSFLDYRDLINCCYVSRRLSQLSSHDPLW | SEQ ID NO:9 |
| AA101399 F3 (Gamma) (mouse) | LPTDPLLLIVSFVDYRDLINCCYVSRSVSQLSTHDPLW | SEQ ID NO:11 |
| F4 (Delta) (human) | LPPEVMLSIFSYLNPQELCRCSQVSMKWSQLTKTGSLW | SEQ ID NO:13 |
| AA167804 F4 (Delta) (mouse) | LPPEVMLSIFSYLNPQELCRCSQVSTKWSQLAKTGSLW | SEQ ID NO:15 |
| F5 (Zeta) (human) | LPLEMLTYILSFLPLSDQKEASLVSWAWYRAAQNALRERLW | SEQ ID NO:17 |
| R17328 F6 (Eta) (human) | LPPELSFTILSYLNAIDLCLASCVWQDLANDELLW | SEQ ID NO:19 |
| AA027176 F6 (Eta) (mouse) | LPPELSFTILSYLNAIDLCLASCVWQDLANDELLW | SEQ ID NO:21 |
| AA213046 F7 (Theta) (mouse) | LPRVLSVYIFSFLDPRSLCRCAQVSWYWKSLAELDQLW | SEQ ID NO:23 |
| AA008567 F8 (Iota) (human) | LPIDVQLYILSFLSPHDLCQLGSTNHYWNETVRHPILW | SEQ ID NO:25 |
| AA295683 F9 (Kappa) (human) | LPLELWRMILAYLHLPDLGRCSLVCRAWYELILSLDSTRW | SEQ ID NO:27 |
| AA459120 F10 (Lambda) (mouse) | LPAEITFKIFSQLDIRSLCRASLTCRSWNDFKS | SEQ ID NO:29 |
| AA501293 F11 (Mu) (mouse) | LPLLQQPLLCSVAHPIASFTMLSYLTGKEAAHLSVELW | SEQ ID NO:31 |
| AA069757 F12 (Nu) (mouse) | LPDSLVYQIFLSLGPADVLAAGLVCRQWQAVSRDEFLW | SEQ ID NO:33 |
| AA000239 F13 (Omicron) (mouse) | LPEEVLALIFRDLPLRDLAVATRVCRAWAAA | SEQ ID NO:35 |
| AA422959 F14 (Pi) (mouse) | LPSVPMMEILSYLDAYSLLQAAQVNKNWNELASSDVLW | SEQ ID NO:37 |
| AA462249 F15 (Rho) (mouse) | MPSEILVKILSYLDAVTLVCIGCVSRRFYHLADDNLIW | SEQ ID NO:39 |
| AA538102 F16 (Sigma) (human) | LPMEVLMYIFRWVVSSDLDLRSLEQLSLVCRGFYICARDPEIW | SEQ ID NO:41 |
| AA49462 F16 (Sigma) (mouse) | LSLVCRGFYICARDPEIW | SEQ ID NO:43 |
| AA410485 F17 (Tau) (human) | LPYELAINIFXYLDRKELGRCAQVSKTWEGD | SEQ ID NO:45 |
| AA381895 F18 (Phi) (human) | LPLELKLRIFRLLDVRSVLSLSAVCRDLFTASNDPLLW | SEQ ID NO:47 |
| AA309734 F18 (Phi) (mouse) | LPLELKLRIFRLLDVHSVLALSAVCHDLLIASNDPLLW | SEQ ID NO:49 |
| W20645 MD6 (human) | LPLELSFYLLKWLDPQTLLTCCLVSKQWNKVISACTEVW | SEQ ID NO:57 |

TABLE 3

F-Box Sequences Identified

| Name and Source | DNA Sequence | SEQ ID NO: |
|---|---|---|
| TRCP (human) | CTGCCAGCTCGGGGATTGGATCATATTGCTGAGAAC ATTCTGTCATACCTGGATGCCAAATCACTATGTGCT GCTGAACTTGTGTGCAAGGAATGGTACCGAGTGACC TCTGATGGCATGCTGTGG | SEQ ID NO:2 |
| F1 (Alpha) (human) | TTACCCAAAGAACTTCTGTTAAGAATATTTTCCTTCT TGGATATAGTAACTTTGTGCCGATGTGCACAGATTT CCAAGGCTTGGAACATCTTAGCCCTGGATGGAAGCA ACTGG | SEQ ID NO:4 |
| F2 (Beta) (human) | CTACCTTATGAGCTTATTCAGCTGATTCTGAATCATC TTACACTACCAGACCTGTGTAGATTAGCACAGAC | SEQ ID NO:6 |
| F2 (Beta) (mouse) | CTACCATATGAGCTCATTCAACTGATTCTGAATCAT CTTTCACTACCAGACCTGTGTAGATTAGCCCAGACT TGCAGGCTTCTCCACCAGCATTGCTGTGATCCTCTG CAATAT | SEQ ID NO:8 |
| F3 (Gamma) (human) | CTGCCCACCGATCCCCTGCTCCTCATCTTATCCTTTT TGGACTATCGGGATCTAATCAACTGTTGTTATGTCA GTCGAAGACTTAGCCAGCTATCAAGTCATGATCCGC TGTGG | SEQ ID NO:10 |
| F3 (Gamma) (mouse) | CTACCCACCGACCCTCTGCTCCTCATAGTATCCTTCG TGGACTACAGGGACCTAATCAATTGTTGCTATGTTA GTCGAAGCGTTAGCCAGCTATCAACTCATGATCCAC TGTGG | SEQ ID NO:12 |
| F4 (Delta) (human) | CTTCCTCCTGAGGTAATGCTGTCAATTTTCAGCTATC TTAATCCTCAAGAGTTATTCGATGCAGTCAAGTAAG CATGAAATGGTCTCAGCTGACAAAAACGGGATCGCT TTGG | SEQ ID NO:14 |
| F4 (Delta) (mouse) | CTTCCTCCTGAGGTAATGCTGTCCATTTTCAGTTACC TTAATCCTCAAGAATTGTGTCGGTGTAGTCAAGTCA GTACTAAGTGGTCTCAGCTGGCAAAAACAGGATCTT TGTGG | SEQ ID NO:16 |
| F5 (Zeta) (human) | CTGCCCCTGGAGATGCTCACATATATTCTGAGCTTC CTGCCTCTGTCAGATCAGAAAGAGGCCTCCCTCGTG AGTTGGGCTTGGTACCGTGCTGCCCAGAATGCCCTT CGGGAGAGGCTGTGG | SEQ ID NO:18 |
| F6 (Eta) (human) | TTGCCTCCTGAGCTAAGCTTTACCATCTTGTCCTACC TGAATGCAACTGACCTTTGCTTGGCTTCATGTGTTTG GCAGGACCTTGCGAATGATGAACTTCTCTGG | SEQ ID NO:20 |
| F6 (Eta) (mouse) | CTGCCTCCTGAGCTGAGCCTCACCATCCTATCCCAC CTGGATGCAACTGACCTTTGCCTAGCTTCCTGTGGTT GGCAAGAACTCGCTAATGATGAACTTCTCTGG | SEQ ID NO:22 |
| F7 (Theta) (mouse) | CTTCCAAGGGTGTTATCTGTCTACATCTTTTCCTTCC TGGATCCCCGGAGTCTTTGCCGTTGTGCACAGGTGA GCTGGTACTGGAAGAGCTTGGCTGAGTTGGACCAGC TCTGG | SEQ ID NO:24 |
| F8 (Iota) (human) | CTGCCGATTGATGTACAGCTATATATTTTGTCCTTTC TTTCACCTCATGATCTGTGTCAGTTGGGAAGTACAA ATCATTATTGGAATGAAACTGTAAGACATCCAATTC TTTGG | SEQ ID NO:26 |
| F9 (Kappa) (human) | CTCCCCTTGGAGCTGTGGCGCATGATCTTAGCCTAC TTGCACCTTCCCGACCTGGGCCGCTGCAGCCTGGTA TGCAGGGCCTGGTATGAACTGATCCTCAGTCTCGAC AGCACCCGCTGG | SEQ ID NO:28 |
| F10 (Lambda) (mouse) | CTGCCTGCAGAAATCACTTTTAAAATTTTCAGTCAG CTGGACATTCGGAGTCTGTGCAGGGCTTCATTGACA TGCAGGAGCTGGAATGAC | SEQ ID NO:30 |
| F11 (Mu) (mouse) | CTGCCATTACTGCAGCAGCCACTTCTGTGTTCTGTG GCTCATCCCATCGCCAGCTTCACCATGCTGTCATAC CTCACGGGAAAGGAGGCCGCTCATCTGTCAGTGGA GTTGTGG | SEQ ID NO:32 |
| F12 (Nu) (mouse) | CTCCCCGACAGCCTTGTCTACCAGATCTTCCTGAGTT TGGGCCCTGCAGATGTGCTGGCTGCTGGGCTGGTAT GCCGCCAATGGCAGGCTGTGTCCCGGGATGAGTTCT TATGG | SEQ ID NO:34 |
| F13 (Omicron) (mouse) | CTGCCAGAGGAAGTGTTGGCGCTCATCTTCCGTGAC CTGCCTCTCAGGGACCTTGCTGTAGCCACCAGAGTC TGCAGGGCCTGGGCGGCGGCT | SEQ ID NO:36 |
| F14 (Pi) (mouse) | TTACCTAGTGTGCCGATGATGGAAATCCTCTCCTAT CTGGATGCCTACAGTTTGCTACAGGCTGCCCAAGTG AACAAGAACTGGAATGAACTTGCAAGCAGTGATGT CCTGTGG | SEQ ID NO:38 |
| F15 (Rho) (mouse) | ATGCCATCGGAAATCTTGGTGAAGATACTTTCTTAC TTGGATGCGGTGACCTTGGTGTGCATTGGATGTGTG AGCAGACGCTTTTATCATTTGGCTGATGACAATCTT ATTTGG | SEQ ID NO:40 |

TABLE 3-continued

F-Box Sequences Identified

| Name and Source | DNA Sequence | SEQ ID NO: |
|---|---|---|
| F16 (Sigma) (human) | CTGCCAATGGAGGTCCTGATGTACATCTTCCGATGG GTGGTGTCTAGTGACTTGGACCTCAGATCATTGGAG CAGTTGTCGCTGGTGTGCAGAGGGTTCTACATCTGT GCCAGAGACCCTGAAATATGG | SEQ ID NO:42 |
| F16 (Sigma) (mouse) | GACTTGGACCTCAGATCGTTAGAGCAGTTGTCACTG GTGTGCAGAGGATTCTATATCTGTGCCAGAGACCCT GAAATCTGG | SEQ ID NO:44 |
| F17 (Tau) (human) | CTGCCTTACGAATTGGCAATCAATATATTTNAGTAT CTGGACAGGAAAGAACTAGGAAGATGTGCACAGGT GAGCAAGACGTGGGAAGGTGATT | SEQ ID NO:46 |
| F18 (Phi) (human) | CTCCCATTGGAACTGAAACTACGGATCTTCCGACTT CTGGATGTTCGTTCCGTCTTGTCTTTGTCTGCGGTTT GTCGTGACCTCTTTACTGCTTCAAATGACCCACTCCT GTGG | SEQ ID NO:48 |
| F18 (Phi) (mouse) | CTTCCACTGGAGCTGAAACTACGCATCTTCCGACTT TTGGATGTTCATTCTGTCCTGGCCCTGTCTGCAGTCT GTCATGACCTCCTCATTGCGTCAAATGACCCACTGC TGTGG | SEQ ID NO:50 |
| MD6 (human) | CTTCCCCTGGAGCTCAGTTTTTATTTGTTAAAATGGC TCGATCCTCAGACTTTACTCACATGCTGCCTCGTCTC TAAACAGTGGAATAAGGTGATAAGTGCCTGTACAG AGGTGTGG | SEQ ID NO:58 |

TABLE 4

Sequences of Some F-Box Proteins

| Name & Source | Sequence | SEQ ID NO: |
|---|---|---|
| F1 Alpha (human) | SAMVFSNNDEGLINKKLPKELLLRIFSFLDIVTLCRCA QISKAWNILALDGSNWQRIDLFNFQIDVEGRVVENISK RCGGFLRKLSLRGCIGVGDSSLKTFAQNCRNIEHLNLN GCTKITDSTCYSLSRFCSKLKHLDLTSCVSITNSSLKGI SEGCRNLEYLNLSWCDQITKDGIEALVRGCRGLKALL LRGCTQLEDEALKHIQNYCHELVSLNLQSCSRITDEGV VQICRGCHRLQALCLSGCSNLTDASLTALGLNCPRLQI LEAARCSHLTDAGFTLLARNCHELEKMDLEECILITDS TLIQLSIHCPKLQALSLSHCELITDDGILHLSNSTCGHE RLRVLELDNCLLITDVALEHLETAEAWSASSCTTASRL PVQASSGCGLSSLMSKSTPTLLPSPHRQQWQEVDSDC AGAVSFSDSSCLGPRGDEASFPLEDLSLPDRLHHHPIC | SEQ ID NO:51 |
| F1 Alpha (human) | TTCGGCCATGGTTTTCTCAAACAATGATGAAGGCCT TATTAACAAAAAGTTACCCAAAGAACTTCTGTTAAG AATATTTTCCTTCTTGGATATAGTAACTTTGTGCCGA TGTGCACAGATTTCCAAGGCTTGGAACATCTTAGCC CTGGATGGAAGCAACTGGCAAAGAATAGATCTTTTT AACTTTCAAATAGATGTAGAGGGTCGAGTGGTGGA AAATATCTCGAAGCGATGCGGTGGATTCCTGAGGA AGCTCAGCTTGCGAGGCTGCATTGGTGTTGGGGATT CCTCCTTGAAGACCTTTGCACAGAACTGCCGAAACA TTGAACATTTGAACCTCAATGGATGCACAAAAATCA CTGACAGCACGTGTTATAGCCTTAGCAGATTCTGTT CCAAGCTGAAACATCTGGATCTGACCTCCTGTGTGT CTATTACAAACAGCTCCTTGAAGGGGATCAGTGAGG GCTGCCGAAACCTGGAGTACCTGAACCTCTCTTGGT GTGATCAGATCACGAAGGATGGCATCGAGGCACTG GTGCGAGGTTGTCGAGGCCTGAAAGCCCTGCTCCTG AGGGGCTGCACACAGTTAGAAGATGAAGCTCTGAA ACACATTCAGAATTACTGCCATGAGCTTGTGAGCCT CAACTTGCAGTCCTGCTCACGTATCACGGATGAAGG TGTGGTGCAGATATGCAGGGGCTGTCACCGGCTACA GGCTCTCTGCCTTTCGGGTTGCAGCAACCTCACAGA TGCCTCTCTTACAGCCCTGGGTTTGAACTGTCCGCG ACTGCAAATTTTGGAGGCTGCCCGATGCTCCCATTT GACTGACGCAGGTTTTACACTTTTAGCTCGGAATTG CCACGAATTGGAGAAGATGGATCTTGAAGAATGCA TCCTGATAACCGACAGCACACTCATCCAGCTCTCCA TTCACTGTCCTAAACTGCAAGCCCTGAGCCTGTCCC ACTGTGAACTCATCACAGATGATGGGATCCTGCACC TGAGCAACAGTACCTGTGGCCATGAGAGGCTGCGG | SEQ ID NO:52 |

TABLE 4-continued

Sequences of Some F-Box Proteins

| Name & Source | Sequence | SEQ ID NO: |
|---|---|---|
| | GTACTGGAGTTGGACAACTGCCTCCTCATCACTGAT GTGGCCCTGGAACACCTAGAAACTGCCGAGGCCTG GAGCGCCTCGAGCTGTACGACTGCCAGCAGGTTACC CGTGCAGGCATCAAGCGGATGCGGGCTCAGCTCCCT CATGTCAAAGTCCACGCCTACTTTGCTCCCGTCACC CCACCGACAGCA | |
| F2 Beta (human) | RPRFGTSDIEDDAYAEKDGCGMDSLNKKFSSAVLGEG PNNGYFDKLPYELIQLILNHLTLPDLCRLAQTCKLLSQ HCCDPLQYIHLNLQPYWAKLDDTSLEFLQSRCTLVQW LNLSWTGNRGFISVAGFSRFLKVCGSELVRLELSCSHF LNETCLEVISEMCPNLQALNLSSCDKLPPQAFNHIAKL CSLKRLVLYRTKVEQTALLSILNFCSELQHLSLGSCVM IEDYDVIASMIGAKCKKLRTLDLWRCKNITENGIAELA SGCPLLEELDLGWCPTLQSSTGCFTRLAHQLPNLQKLF LTANRSVCDTDIDELACNCTRLQQLDILGKVTIYKFVL NVCFLDRKANLRLFVRKKKIFGYNKNFILIRWLGLIGN AR | SEQ ID NO:53 |
| F2 Beta (human) | AGGCCAAGATTCGGCACGAGTGATATAGAAGATGA TGCCTATGCAGAAAAGGATGGTTGTGGAATGGACA GTCTTAACAAAAAGTTTAGCAGTGCTGTCCTCGGGG AAGGGGCCAAATAATGGGTATTTTGATAAACTACCTT ATGAGCTTATTCAGCTGATTCTGAATCATCTTACAC TACCAGACCTGTGTAGATTAGCACAGACTTGCAAAC TACTGAGCCAGCATTGCTGTGATCCTCTGCAATACA TCCACCTCAATCTGCAACCATACTGGGCAAAACTAG ATGACACTTCTCTGGAATTTCTACAGTCTCGCTGCA CTCTTGTCCAGTGGCTTAATTTATCTTGGACTGGCA ATAGAGGCTTCATCTCTGTTGCAGGATTTAGCAGGT TTCTGAAGGTTTGTGGATCCGAATTAGTACGCCTTG AATTGTCTTGCAGCCACTTTCTTAATGAAACTTGCTT AGAAGTTATTTCTGAGATGTGTCCAAATCTACAGGC CTTAAATCTCTCCTCCTGTGATAAGCTACCACCTCA AGCTTTCAACCACATTGCCAAGTTATGCAGCCTTAA ACGACTTGTTCTCTATCGAACAAAAGTAGAGCAAAC AGCACTGCTCAGCATTTTGAACTTCTGTTCAGAGCT TCAGCACCTCAGTTTAGGCAGTTGTGTCATGATTGA AGACTATGATGTGATAGCTAGCATGATAGGAGCCA AGTGTAAAAAACTCCGGACCCTGGATCTGTGGAGAT GTAAGAATATTACTGAGAATGGAATAGCAGAACTG GCTTCTGGGTGTCCACTACTGGAGGAGCTTGACCTT GGCTGGTGCCCAACTCTGCAGAGCAGCACCGGGTGC TTCACCAGACTGGCACACCAGCTCCCAAACTTGCAA AAACTCTTTCTTACAGCTAATAGATCTGTGTGTGAC ACAGACATTGATGAATTGGCATGTAATTGTACCAGG TTACAGCAGCTGGACATATTAGGTAAGGTTACAATA TATAAATTTGTTTTAAATGTCTGTTTCCTTGACAGAA AAGCCAATCTCAGACTTTTTGTTAGGAAAAAGAAAA TTTTTGGATACAATAAAAATTTTATCCTGATAAGAT GGCTTGGTTTGATAGGAAATGCCAGATAGATCAGTT AATATAGGGAATAATTATATATGTACTTTAATAAAA TAGTGAGGACAATAACAATTTTATAGTTGAACTGTA AAAAACTATAACCATTAATTCTTGGTCTACTTGTAA GAGTGAGAATTTACATGAGCTGCGCTCTCTATTTTT ATTAAGGAGAGAAGAAATTAATTCATTTGTATAATG AATTCAAGCTAGTTTTTTTTAAGTTTCTTA | SEQ ID NO:54 |
| F4 Delta (human) | MVIMLZERQKFFKYSVDEKSDKEAEVSEHSTGITHLPP EVMLSIFSYLNPQELCRCSQVSMKWSQLTKTGSLWKH LYPVHWARGDWYSGPATELDTEPDDEWVKNRKDES RAFHEWDEDADIDESEESAEESIAISIAQMEKRLLHGLI HNVLPYVGTSVKTLVLAYSSAVSSKMVRQILELCPNL EHLDLTQTDISDSAFDSWSWLGCCQSLRHLDLSGCEKI TDVALEKISRALGILTSHQSGFLKTSTSKITSTAWKNK DITMQSTKQYACLHDLTNKGIGEEIDNEHPWTKPVSS ENFTSPYVWMLDAEDLADIEDTVEWRHRNVESLCVM ETASNFSCSTSGCFSKDIVGLRTSVCWQQHCASPAFAY CGHSFCCTGTALRTMSSLPESSAMCRKAARTRLPRGK DLIYFGSEKSDQETGRVLLFLSLSGCYQITDHGLRVLT LGGGLPYLEHLNLSGCLTITGAGLQDLVSACPSLNDE YFYYCDNINGPHADTASGCQNLQCGFRACCRSGE | SEQ ID NO:55 |
| F4 Delta (human) | ATGGTAATCATGCTGTAAGAGCGACAGAAATTTTTT AAATATTCCGTGGATGAAAAGTCAGATAAAGAAGC AGAAGTGTCAGAACACTCCACAGGTATAACCCATCT TCCTCCTGAGGGTAATGCTGTCAATTTTCAGCTATCTT AATCCTCAAGAGTTATGTCGATGCAGTCAAGTAAGC | SEQ ID NO:56 |

TABLE 4-continued

Sequences of Some F-Box Proteins

| Name & Source | Sequence | SEQ ID NO: |
|---|---|---|
| | ATGAAATGGTCTCAGCTGACAAAAACGGGATCGCTT<br>TGGAAACATCTTTACCCTGTTCATTGGGCCAGAGGT<br>GACTGGTATAGTGGTCCCGCAACTGAACTTGATACT<br>GAACCTGATGATGAATGGGTGAAAAATAGGAAAGA<br>TGAAAGTCGTGCTTTTCATGAGTGGGATGAAGATGC<br>TGACATTGATGAATCTGAAGAGTCTGCGGAGGAATC<br>AATTGCTATCAGCATTGCACAAATGGAAAAACGTTT<br>ACTCCATGGCTTAATTCATAACGTTCTACCATATGTT<br>GGTACTTCTGTAAAAACCTTAGTATTAGCATACAGC<br>TCTGCAGTTTCCAGCAAAATGGTTAGGCAGATTTTA<br>GAGCTTTGTCCTAACCTGGAGCATCTGGATCTTACC<br>CAGACTGACATTTCAGATTCTGCATTTGACAGTTGG<br>TCTTGGCTTGGTTGCTGCCAGAGTCTTCGGCATCTTG<br>ATCTGTCTGGTTGTGAGAAAATCACAGATGTGGCCC<br>TAGAGAAGATTTCCAGAGCTCTTGGAATTCTGACAT<br>CTCATCAAAGTGGCTTTTTGAAAACATCTACAAGCA<br>AAATTACTTCAACTGCGTGGAAAAATAAAGACATTA<br>CCATGCAGTCCACCAAGCAGTATGCCTGTTTGCACG<br>ATTTAACTAACAAGGGCATTGGAGAAGAAATAGAT<br>AATGAACACCCCTGGACTAAGCCTGTTTCTTCTGAG<br>AATTTCACTTCTCCTTATGTGTGGATGTTAGATGCTG<br>AAGATTTGGCTGATATTGAAGATACTGTGGAATGGA<br>GACATAGAAATGTTGAAAGTCTTTGTGTAATGGAAA<br>CAGCATCCAACTTTAGTTGTTCCACCTCTGGTTGTTT<br>TAGTAAGGACATTGTTGGACTAAGGACTAGTGTCTG<br>TTGGCAGCAGCATTGTGCTTCTCCAGCCTTTGCGTA<br>TTGTGGTCACTCATTTTGTTGTACAGGAACAGCTTT<br>AAGAACTATGTCATCACTCCCAGAATCTTCTGCAAT<br>GTGTAGAAAAGCAGCAAGGACTAGATTGCCTAGGG<br>GAAAAGACTTAATTTACTTTGGGAGTGAAAAATCTG<br>ATCAAGAGACTGGACGTGTACTTCTGTTTCTCAGTT<br>TATCTGGATGTTATCAGATCACAGACCATGGTCTCA<br>GGGTTTTGACTCTGGGAGGAGGGCTGC | 35 |

It is clear from the above that the present invention provides F-box proteins and other compositions and methods for the development of compositions capable of affecting proteolysis, as well as methods and compositions for the investigation and identification of additional F-box proteins.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated nucleic acid segment comprising a nucleic acid sequence encoding a protein comprising at least one functionally active F-Box domain sequence, wherein said isolated nucleic acid segment is selected from the group consisting of SEQ ID NOS 2 and 52.

2. The isolated nucleic acid segment of claim 1, wherein the nucleic acid sequence comprises mammalian nucleic acid.

3. The isolated nucleic acid segment of claim 1, wherein the sequence is capable of amplification by polymerase chain reaction.

4. The isolated nucleic acid segment of claim 1, wherein the at least one functionally active F-Box domain forms a complex with F-Box domain targets selected from the group consisting of cyclins, cyclin dependent kinases, and IkB.

5. The isolated nucleic acid segment of claim 4, wherein the complex comprises a target for ubiquitination.

6. The isolated nucleic acid segment of claim 1, wherein the at least one functionally active F-Box domain forms a complex with Skp1.

7. The isolated nucleic acid segment of claim 6, wherein the complex comprises a target for ubiquitination.

8. A vector comprising the isolated nucleic acid segment of claim 1.

9. The vector of claim 8, wherein the vector is an expression vector.

10. The vector of claim 9, wherein the expression vector is a baculovirus expression vector.

11. The vector of claim 8, wherein the vector is transfected into eukaryotic cells.

12. The vector of claim 8, wherein the vector is transfected into insect cells.

13. The vector of claim 8, wherein the vector is a plasmid.

14. The vector of claim 8, wherein the vector is transfected into procaryotic cells.

15. The vector of claim 8, wherein the vector is transfected into bacteria.

16. A host cell transformed with the vector of claim 8.

17. The host cell of claim 16, wherein the host cell is an eukaryotic cell.

18. The host cell of claim 16, wherein the host cell is a mammalian cell.

19. The host cell of claim 16, wherein the host cell is a prokaryotic cell.

20. The host cell of claim 16, wherein the host cell is an insect cell.

21. An isolated nucleic acid segment consisting essentially of a nucleic acid sequence encoding a protein comprising at least one functionally active F-Box domain sequence, wherein said isolated nucleic acid segment is selected from the group consisting of SEQ ID NOS: 2 and 52.

22. A vector comprising the isolated nucleic acid segment of claim 21.

23. The vector of claim 22, wherein the vector is an expression vector.

* * * * *